United States Patent
Arnault De La Menardiere et al.

(10) Patent No.: US 8,128,680 B2
(45) Date of Patent: Mar. 6, 2012

(54) APPARATUS AND METHOD FOR DEPLOYING AN IMPLANTABLE DEVICE WITHIN THE BODY

(75) Inventors: Brice Maxime Arnault De La Menardiere, Santa Cruz, CA (US); Frederich Albert Lim Alavar, San Jose, CA (US); Robert C. Laduca, Santa Cruz, CA (US); Paul A. Laduca, Buffalo, NY (US)

(73) Assignee: Taheri LaDuca LLC, Santa Cruz, CA (US)

(*) Notice: Subject to any disclaimer, the term of this patent is extended or adjusted under 35 U.S.C. 154(b) by 200 days.

(21) Appl. No.: 11/539,478

(22) Filed: Oct. 6, 2006

(65) Prior Publication Data
US 2007/0167955 A1    Jul. 19, 2007

Related U.S. Application Data

(63) Continuation-in-part of application No. PCT/US2006/000756, filed on Jan. 9, 2006, and a continuation-in-part of application No. 11/329,384, filed on Jan. 9, 2006, which is a continuation-in-part of application No. 11/241,242, filed on Sep. 30, 2005, which is a continuation-in-part of application No. 11/033,479, filed on Jan. 10, 2005.

(60) Provisional application No. 60/752,128, filed on Dec. 19, 2005, provisional application No. 60/756,445, filed on Jan. 4, 2006.

(51) Int. Cl.
*A61F 2/06* (2006.01)

(52) U.S. Cl. .................................. 623/1.23; 623/1.35
(58) Field of Classification Search ................... 623/1.1, 623/1.11, 1.23, 1.16, 1.35
See application file for complete search history.

(56) References Cited

U.S. PATENT DOCUMENTS

| | | | |
|---|---|---|---|
| 4,501,263 A | 2/1985 | Harbuck | |
| 4,830,003 A | 5/1989 | Wolff et al. | |
| 4,872,874 A | 10/1989 | Taheri | |
| 4,902,508 A | 2/1990 | Badylak et al. | |
| 4,913,141 A | 4/1990 | Hillstead | |
| 4,956,178 A | 9/1990 | Badylak et al. | |
| 5,026,377 A | 6/1991 | Burton et al. | |
| 5,042,707 A | 8/1991 | Taheri | |
| 5,042,976 A | 8/1991 | Ishitsu et al. | |
| 5,275,826 A | 1/1994 | Badylak et al. | |

(Continued)

FOREIGN PATENT DOCUMENTS
WO    WO 03/007823    1/2003

OTHER PUBLICATIONS

Kasyanov, V. et al., "Tannic acid mimicking dendrimers as small intestine submucosa stabilizing nanomordants," *Biomaterials*, 27:745-751, 2005, Elsevier Ltd.

*Primary Examiner* — William H. Matthews
(74) *Attorney, Agent, or Firm* — Levine Bagade Han LLP

(57) ABSTRACT

The present invention provides systems and methods for deploying implantable devices within the body. The delivery and deployment systems include at least one catheter or an assembly of catheters for selectively positioning the lumens of the implant to within target vessels. Various deployment and attachment mechanisms are provided for selectively deploying the implants.

33 Claims, 40 Drawing Sheets

U.S. PATENT DOCUMENTS

| | | |
|---|---|---|
| 5,415,664 A | 5/1995 | Pinchuk |
| 5,464,449 A | 11/1995 | Ryan et al. |
| 5,554,389 A | 9/1996 | Badylak et al. |
| 5,591,228 A | 1/1997 | Edoga |
| 5,617,878 A | 4/1997 | Taheri |
| 5,653,743 A | 8/1997 | Martin |
| 5,669,924 A | 9/1997 | Shaknovich |
| 5,676,696 A | 10/1997 | Marcade |
| 5,676,697 A | 10/1997 | McDonald |
| 5,693,083 A | 12/1997 | Baker et al. |
| 5,700,269 A | 12/1997 | Pinchuk et al. |
| 5,723,004 A | 3/1998 | Dereume et al. |
| 5,741,325 A | 4/1998 | Chaikof et al. |
| 5,755,735 A | 5/1998 | Richter et al. |
| 5,800,507 A | 9/1998 | Schwartz |
| 5,824,064 A | 10/1998 | Taheri |
| 5,843,167 A | 12/1998 | Dwyer et al. |
| 5,843,169 A | 12/1998 | Taheri |
| 5,948,017 A | 9/1999 | Taheri |
| 5,984,955 A | 11/1999 | Wisselink |
| 5,993,481 A | 11/1999 | Marcade et al. |
| 6,017,363 A | 1/2000 | Hojeibane |
| 6,030,414 A | 2/2000 | Taheri |
| 6,033,434 A | 3/2000 | Borghi |
| 6,059,824 A | 5/2000 | Taheri |
| 6,074,398 A | 6/2000 | Leschinsky |
| 6,077,297 A | 6/2000 | Robinson et al. |
| 6,099,548 A | 8/2000 | Taheri |
| 6,106,549 A | 8/2000 | Taheri |
| 6,129,738 A | 10/2000 | Lashinski et al. |
| 6,183,504 B1 | 2/2001 | Inoue |
| 6,183,509 B1 | 2/2001 | Dibie |
| 6,187,033 B1 | 2/2001 | Schmitt et al. |
| 6,210,429 B1 | 4/2001 | Vardi et al. |
| 6,224,609 B1 | 5/2001 | Ressemann et al. |
| 6,228,052 B1 | 5/2001 | Pohndorf |
| 6,238,432 B1 | 5/2001 | Parodi |
| 6,280,465 B1 | 8/2001 | Cryer |
| 6,306,145 B1 | 10/2001 | Leschinsky |
| 6,325,826 B1 | 12/2001 | Vardi et al. |
| 6,383,213 B2 | 5/2002 | Wilson et al. |
| 6,409,750 B1 | 6/2002 | Hyodoh et al. |
| 6,440,161 B1 | 8/2002 | Madrid et al. |
| 6,471,722 B1 | 10/2002 | Inoue |
| 6,478,817 B2 | 11/2002 | Schmitt et al. |
| 6,508,835 B1 | 1/2003 | Shaolian et al. |
| 6,520,988 B1 | 2/2003 | Colombo et al. |
| 6,533,811 B1 | 3/2003 | Ryan et al. |
| 6,551,350 B1 | 4/2003 | Thornton et al. |
| 6,599,302 B2 | 7/2003 | Houser et al. |
| 6,613,072 B2 | 9/2003 | Lau et al. |
| 6,641,606 B2 | 11/2003 | Ouriel et al. |
| 6,673,107 B1 | 1/2004 | Brandt et al. |
| 6,682,536 B2 | 1/2004 | Vardi et al. |
| 6,695,877 B2 | 2/2004 | Brucker et al. |
| 6,723,116 B2 | 4/2004 | Taheri |
| 6,732,116 B2 | 5/2004 | Banerjee et al. |
| 6,733,522 B2 | 5/2004 | Schmitt et al. |
| 6,749,628 B1 | 6/2004 | Callol et al. |
| 6,761,733 B2 * | 7/2004 | Chobotov et al. ............ 623/1.12 |
| 6,761,734 B2 | 7/2004 | Suhr |
| 6,770,090 B2 | 8/2004 | Gantt et al. |
| 6,814,752 B1 | 11/2004 | Chuter |
| 6,824,558 B2 | 11/2004 | Parodi |
| 6,849,087 B1 | 2/2005 | Chuter |
| 6,918,925 B2 | 7/2005 | Tehrani |
| 6,945,990 B2 | 9/2005 | Greenan |
| 6,984,244 B2 * | 1/2006 | Perez et al. ................... 623/1.23 |
| 7,014,653 B2 | 3/2006 | Ouriel et al. |
| 7,074,235 B1 | 7/2006 | Roy |
| 7,105,020 B2 | 9/2006 | Greenberg et al. |
| 7,122,052 B2 | 10/2006 | Greenhalgh |
| 7,144,421 B2 | 12/2006 | Carpenter et al. |
| 7,189,257 B2 | 3/2007 | Schmitt et al. |
| 7,294,147 B2 * | 11/2007 | Hartley ........................ 623/1.13 |
| 7,306,623 B2 | 12/2007 | Watson |
| 2001/0003161 A1 | 6/2001 | Vardi et al. |
| 2001/0027338 A1 | 10/2001 | Greenberg |
| 2002/0156518 A1 | 10/2002 | Tehrani |
| 2003/0097170 A1 | 5/2003 | Friedrich et al. |
| 2003/0220680 A1 | 11/2003 | Kashyap |
| 2003/0229389 A1 | 12/2003 | Escano |
| 2004/0117003 A1 | 6/2004 | Ouriel et al. |
| 2004/0172121 A1 | 9/2004 | Eidenschink et al. |
| 2004/0215338 A1 | 10/2004 | Elkins et al. |
| 2004/0230287 A1 | 11/2004 | Hartley et al. |
| 2004/0243221 A1 * | 12/2004 | Fawzi et al. ................... 623/1.23 |
| 2005/0010277 A1 | 1/2005 | Chuter |
| 2005/0033406 A1 | 2/2005 | Barnhart et al. |
| 2005/0049667 A1 | 3/2005 | Arbefeuille et al. |
| 2005/0049674 A1 | 3/2005 | Berra et al. |
| 2005/0102018 A1 | 5/2005 | Carpenter et al. |
| 2006/0129224 A1 | 6/2006 | Arbefeuille et al. |
| 2006/0155363 A1 | 7/2006 | LaDuca et al. |
| 2007/0055350 A1 | 3/2007 | Erickson et al. |
| 2007/0150051 A1 | 6/2007 | Arnault De La Menardiere et al. |
| 2007/0179592 A1 | 8/2007 | Schaeffer |
| 2008/0097404 A1 | 4/2008 | Yribarren et al. |
| 2009/0043373 A1 | 2/2009 | Arnault De La Menardiere et al. |
| 2009/0182405 A1 | 7/2009 | Arnault De La Menardiere et al. |

* cited by examiner

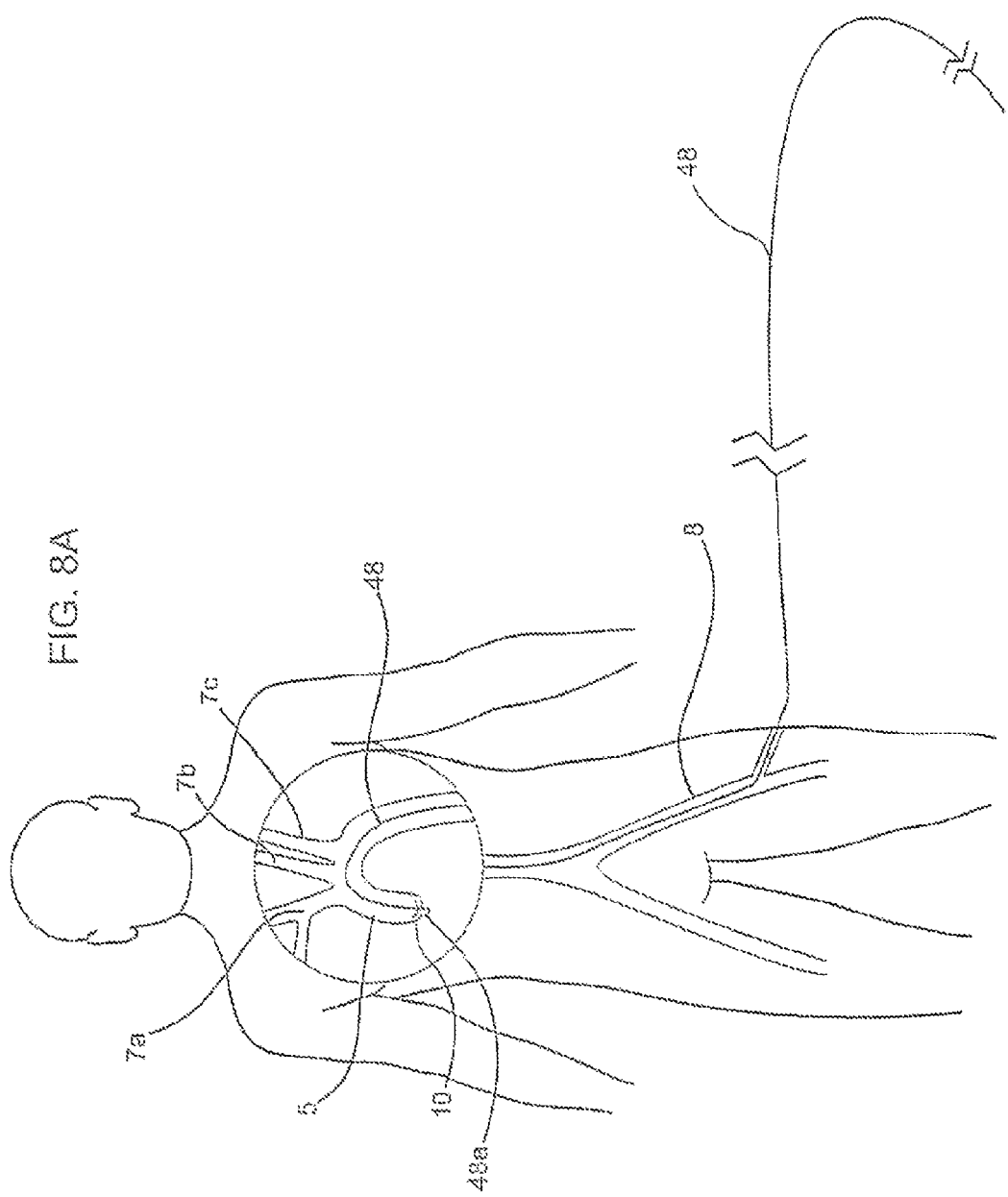

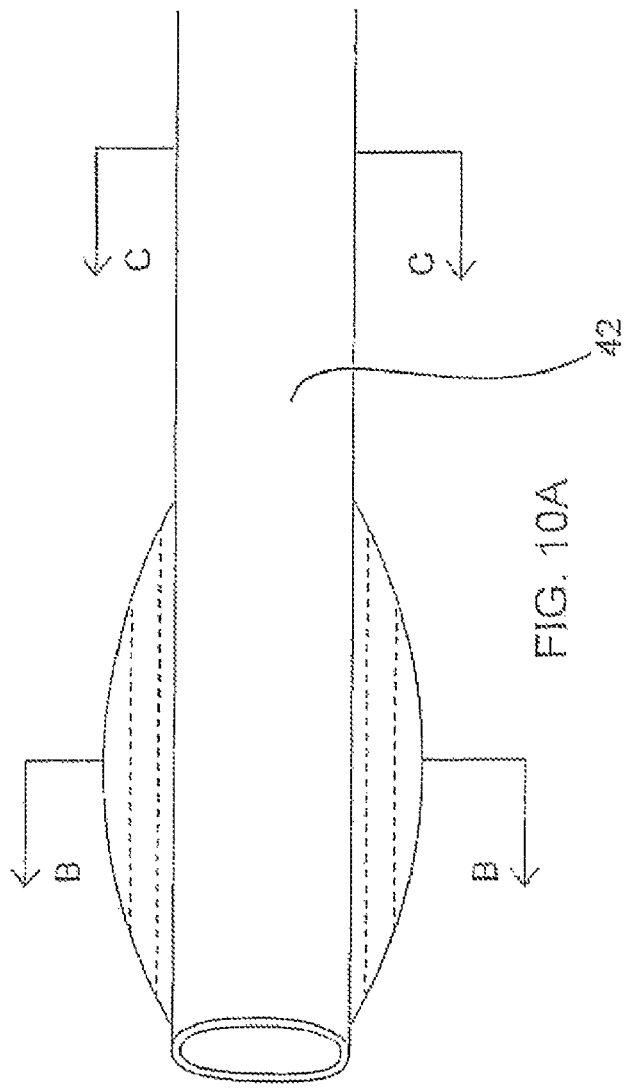
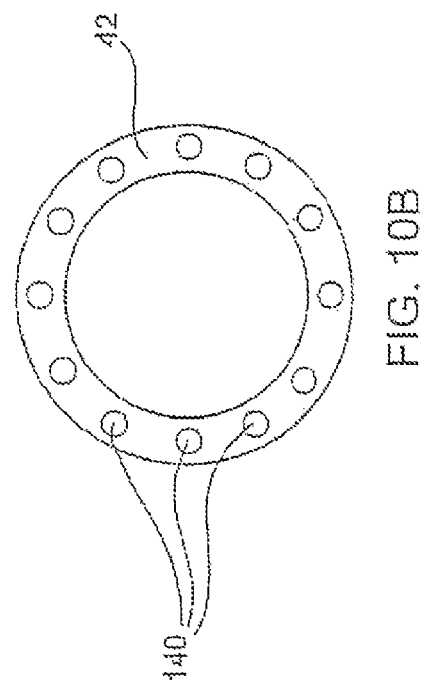
FIG. 10A
FIG. 10B
FIG. 10C

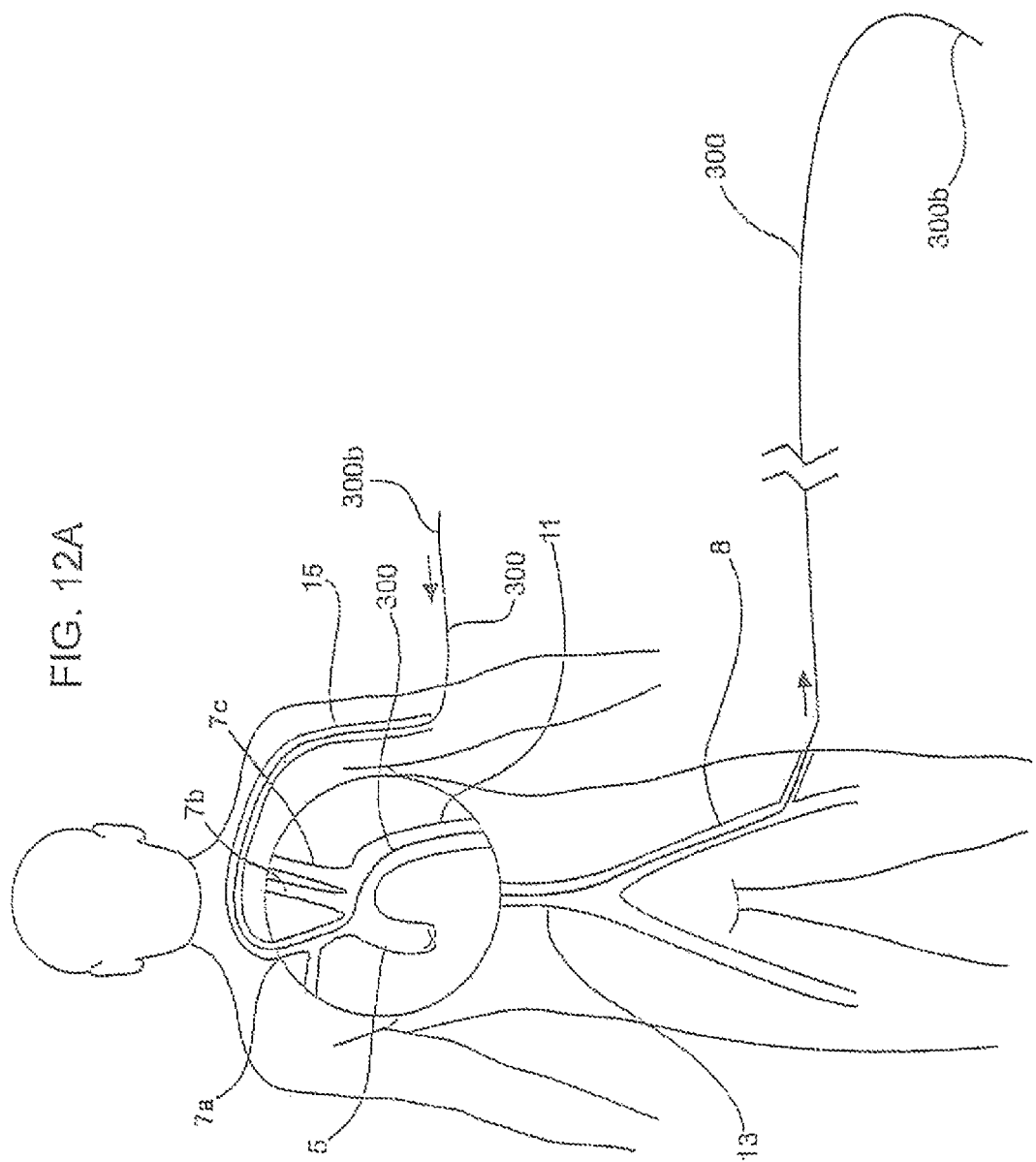

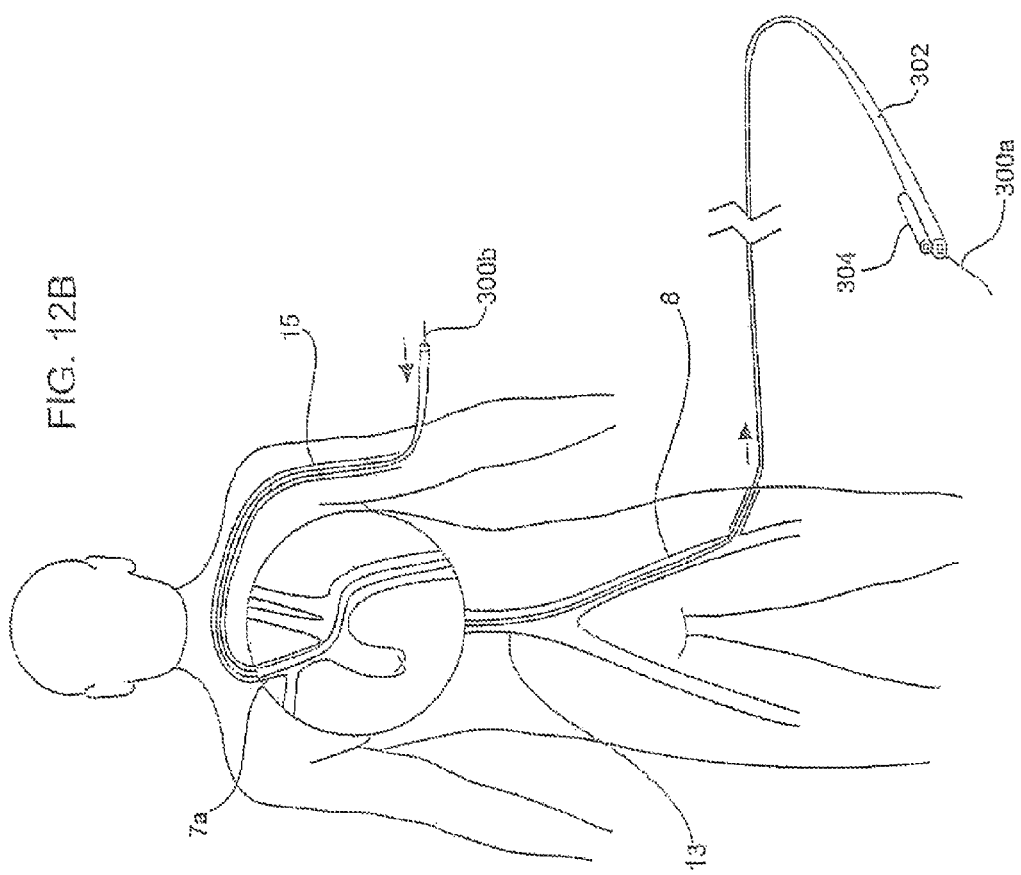

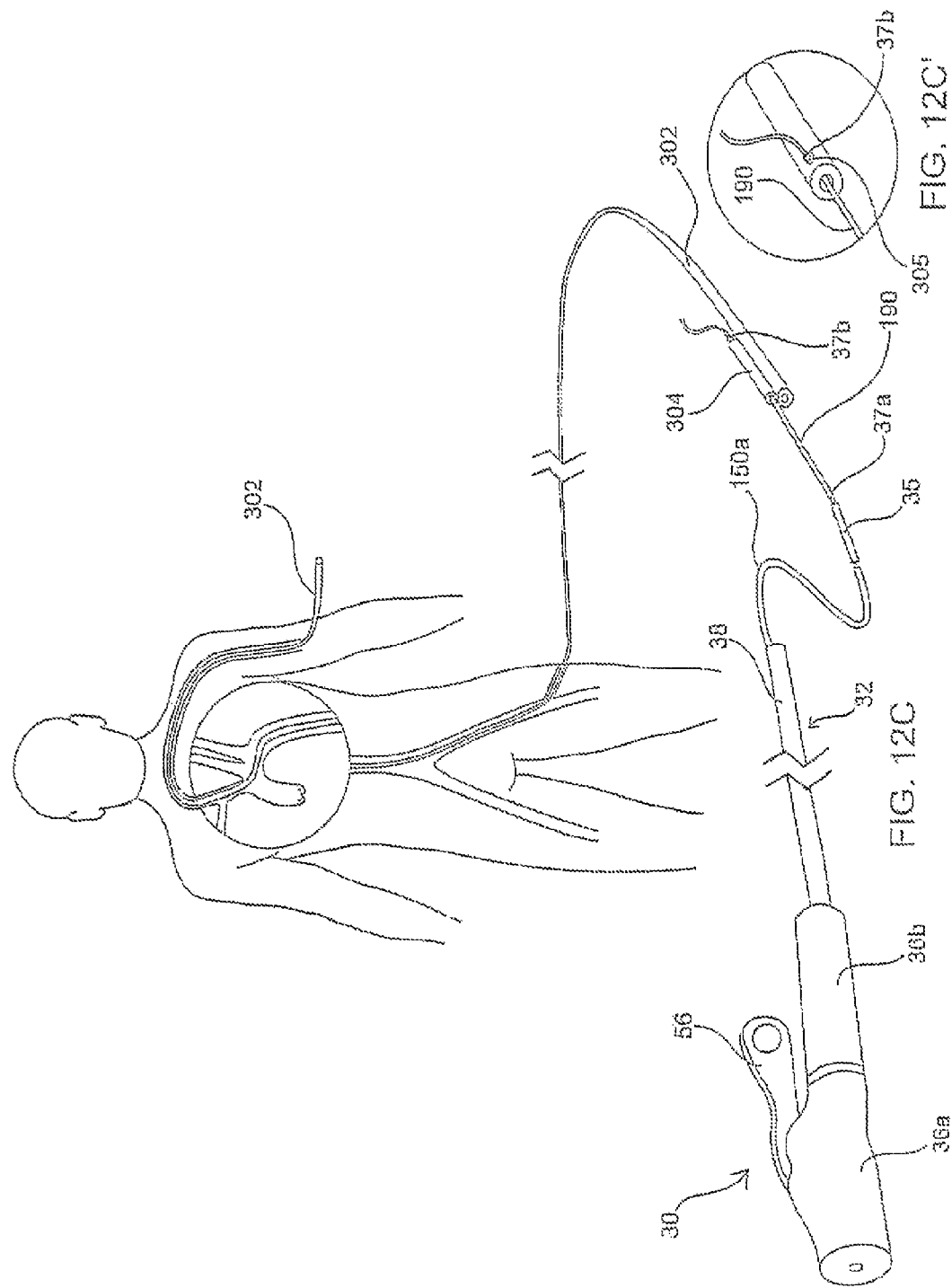

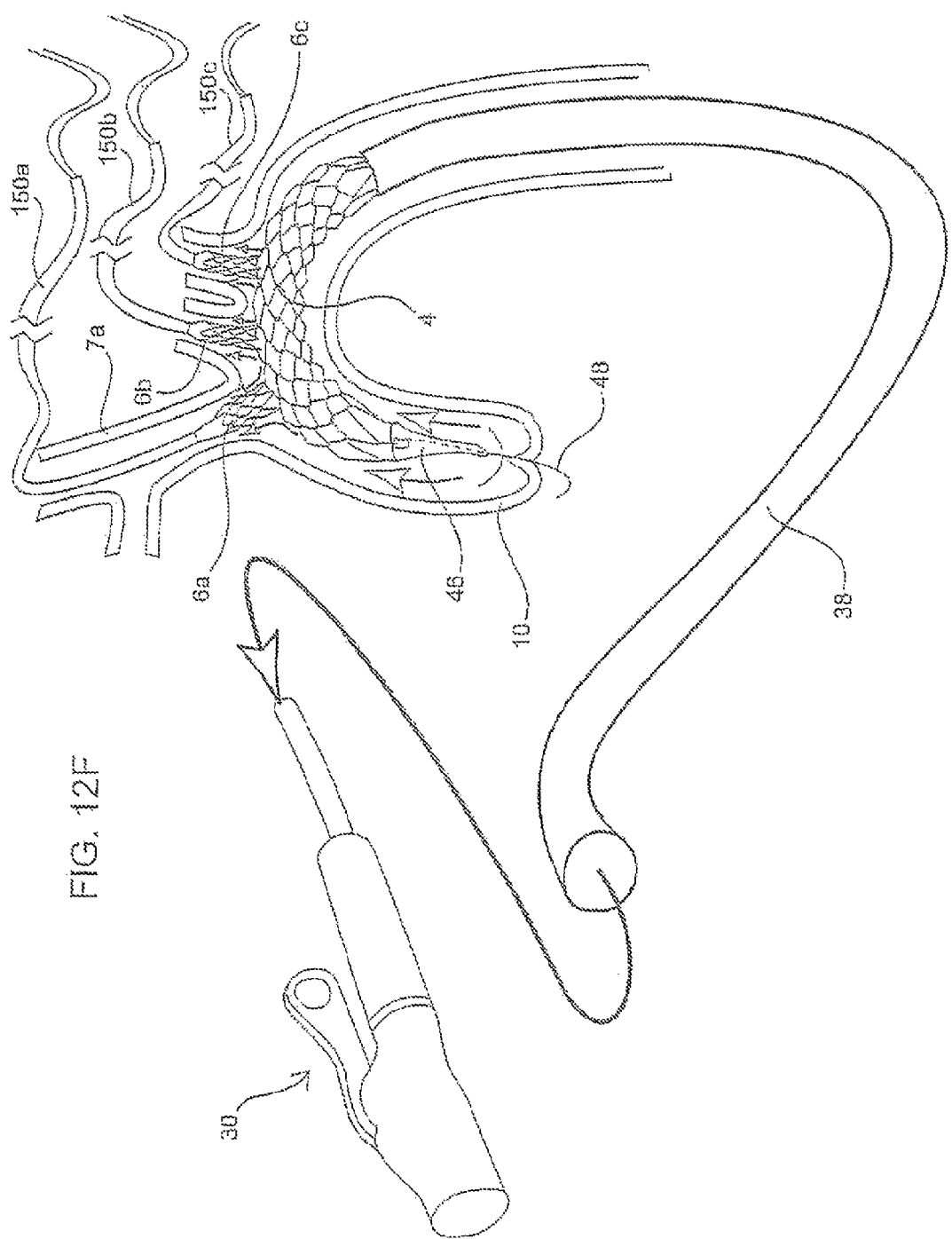

APPARATUS AND METHOD FOR DEPLOYING AN IMPLANTABLE DEVICE WITHIN THE BODY

CROSS REFERENCES TO RELATED APPLICATIONS

This application claims the benefit of U.S. Provisional Application No. 60/756,445, filed Jan. 4, 2006 and of U.S. Provisional Application No. 60/752,128, filed Dec. 19, 2005; this application is also a continuation-in-part of International Application No. PCT/US2006/000756, filed Jan. 9, 2006, and of U.S. patent application Ser. No. 11/329,384, filed Jan. 9, 2006, which is a continuation-in-part application of U.S. patent application Ser. No. 11/241,242, filed Sep. 30, 2005, which is a continuation-in-part of U.S. patent application Ser. No. 11/033,479, filed Jan. 10, 2005, which are incorporated herein by reference in their entirety noting that the current application controls to the extent there is any contradiction with any earlier applications and to which applications we claim priority under 35 USC §120.

FIELD OF THE INVENTION

The present invention relates to the treatment of vascular disease, including for example aneurysms, ruptures, psuedoaneurysms, dissections, exclusion of vulnerable plaque and treatment of occlusive conditions, and more particularly, the invention is related to an apparatus and method for delivering and deploying an implantable device within the body to treat such conditions. The present invention is particularly suitable for implanting stents, grafts and stent grafts within arteries or other vessels at sites involving two or more intersecting vessels.

BACKGROUND OF THE INVENTION

It is well known in the prior art to treat vascular disease with implantable stents and grafts. For example, it is well known in the art to interpose within a stenotic or occluded portion of an artery a stent capable of self-expanding or being balloon-expandable. Similarly, it is also well known in the prior art to use a graft or a stent graft to repair highly damaged or vulnerable portions of a vessel, particularly the aorta, thereby ensuring blood flow and reducing the risk of an aneurysm or rupture.

A more challenging situation occurs when it is desirable to use a stent, a graft or a stent graft at or around the intersection between a major artery (e.g., the abdominal aorta) and one or more intersecting arteries (e.g., the renal arteries). Use of single axial stents or grafts may effectively seal or block-off the blood flow to collateral organs such as the kidneys. U.S. Pat. No. 6,030,414 addresses such a situation, disclosing use of a stent graft having lateral openings for alignment with collateral blood flow passages extending from the primary vessel into which the stent graft is positioned. The lateral openings are pre-positioned within the stent based on identification of the relative positioning of the lateral vessels with which they are to be aligned. U.S. Pat. No. 6,099,548 discloses a multi-branch graft and a system for deploying it. Implantation of the graft is quite involved, requiring a discrete, balloon-deployable stent for securing each side branch of the graft within a designated branch artery. Additionally, a plurality of stylets is necessary to deliver the graft, occupying space within the vasculature and thereby making the system less adaptable for implantation into smaller vessels. Further, delivery of the graft and the stents requires access and exposure to each of the branch vessels into which the graft is to be placed by way of a secondary arteriotomy. These techniques, while effective, may be cumbersome and somewhat difficult to employ and execute, particularly where the implant site involves two or more vessels intersecting the primary vessel, all of which require engrafting.

The use of bifurcated stents for treating abdominal aortic aneurysms (AAA) is well known in the art. These stents have been developed specifically to address the problems that arise in the treatment of vascular defects and or disease at or near the site of a bifurcation. The bifurcated stent is typically configured in a "pant" design which comprises a tubular body or trunk and two tubular legs. Examples of bifurcated stents are provided in U.S. Pat. Nos. 5,723,004 and 5,755,735. Bifurcated stents may have either unitary or modular configurations in which the components of the stent are interconnected in situ. In particular, one or both of the leg extensions are attachable to a main tubular body. Although the delivery of modular systems is less difficult due to the smaller sizes of the components, it is difficult to align and interconnect the legs with the body lumen with enough precision to avoid any leakage. On the other hand, while unitary stents reduce the probability of leakage, their larger structure is often difficult to deliver to a treatment site having a constrained geometry.

The highly curved anatomy of the aortic arch requires a stent that can accommodate various radii of curvature. More particularly, the stent wall is required to be adaptable to the tighter radius of curvature of the underside of the aortic arch without kinking while being able to extend or stretch to accommodate the longer topside of the arch without stretching the stent cells/wire matrix beyond its elastic capabilities.

Additionally, the variability of the anatomy of the aortic arch from person to person makes it a difficult location in which to place a stent graft. While the number of branch vessels originating from the arch is most commonly three, namely, the left subclavian artery, the left common carotid artery and the innominate artery, in some patients the number of branch vessels may be one, more commonly two and in some cases four, five or even six. Moreover, the spacing and angular orientation between the tributary vessels are variable from person to person.

Still yet, placing stents/grafts within the aortic arch presents additional challenges. The arch region of the aorta is subject to very high blood flow and pressures which make it difficult to position a stent graft without stopping the heart and placing the patient on cardiopulmonary bypass. Moreover, even if the stent graft is able to be properly placed, it must be secured in a manner to endure the constant high blood flow, pressures, and shear forces it is subjected to over time in order to prevent it from migrating or leaking. Additionally, the aorta undergoes relatively significant changes (of about 7%) in its diameter due to vasodilation and vasorestriction. As such, if an aortic arch graft is not able to expand and contract to accommodate such changes, there may be an insufficient seal between the graft and the aortic wall, subjecting it to a risk of migration and/or leakage.

In order to achieve alignment of a side branch stent or a lateral opening of the main stent with a branch vessel, a custom stent designed and manufactured according to each patient's unique geometrical constraints would be required. The measurements required to create a custom manufactured stent to fit the patient's unique vascular anatomy could be obtained using spiral tomography, computed tomography (CT), fluoroscopy, or other vascular imaging system. However, while such measurements and the associated manufacture of such a custom stent could be accomplished, it would be time consuming and expensive. Furthermore, for those patients who require immediate intervention involving the use of a stent, such a customized stent is impractical. In these situations it would be highly desirable to have a stent which is capable of adjustability in situ while being placed. It would likewise be highly desirable to have the degree of adjustability sufficient to allow for a discrete number of stents to be manufactured in advance and available to accommodate the required range of sizes and configurations encountered.

Another disadvantage of conventional stents and stent grafts is the limitations in adjusting the position of or subsequently retrieving the stent or stent-graft once it has been deployed. Often, while the stent is being deployed, the final location of the delivered stent is determined not to be optimal for achieving the desired therapeutic effect. During deployment of self-expanding stents, the mode of deployment is either to push the stent out of a delivery catheter, or more commonly to retract an outer sheath while holding the stent in a fixed location relative to the vasculature. In either case the distal end of the stent is not attached to the catheter and, as such, is able to freely expand to its maximum diameter and seal with the surrounding artery wall. While this self-expanding capability is advantageous in deploying the stent, it presents the user with a disadvantage when desiring to remove or reposition the stent. Some designs utilize a trigger wire(s) to retain the distal end of the stent selectively until such time as full deployment is desired and accomplished by releasing the "trigger" wire or tether wire(s). The limitation of this design is the lack of ability to reduce the diameter of the entire length of stent by stretching the stent which is pursed down on the distal end by the trigger wire. The significance of reducing the diameter of the stent while positioning and determining if it should be released from the tether wire is that the blood flow is occluded by the fully expanded main body of the stent even while the distal end is held from opening by the tether wire.

Another disadvantage of conventional stent-grafts is the temporary disruption in blood flow through the vessel. In the case of balloon deployable stents and stent-grafts, expansion of the balloon itself while deploying the stent or stent-graft causes disruption of blood flow through the vessel. Moreover, in certain applications, a separate balloon is used at a location distal to the distal end of the stent delivery catheter to actively block blood flow while the stent is being placed. In the case of self-expanding stent-grafts, the misplacement of a stent graft may be due to disruption of the arterial flow during deployment, requiring the placement of an additional stent-graft in an overlapping fashion to complete the repair of the vessel. Even without disruptions in flow, the strong momentum of the arterial blood flow can cause a partially opened stent-graft to be pushed downstream by the high-pressure pulsatile impact force of the blood entering the partially deployed stent graft.

Attempts have been made to address some of the above-described disadvantages of conventional stents and stent grafts. For example, U.S. Pat. No. 6,099,548 discloses the use of strings passed through and attached to the distal end of the stent which is inserted through a first opening in the vasculature. The string ends are then passed through a second opening in the vasculature such that they can be pulled, thereby moving the stent within the vasculature. While the use of attached strings provides some additional control of the stent's placement, one skilled in the art can appreciate that passing strings from within the vasculature through a second opening presents procedural difficulties. Moreover, it is advantageous to the welfare of the patient to minimize the number of surgical openings when performing any procedure.

With the limitations of current stent grafts and stent graft placement technologies, there is clearly a need for an improved means and method for implanting a stent or graft and for treating vascular disease and conditions affecting interconnecting vessels (i.e., vascular trees) which address the drawbacks of the prior art.

SUMMARY OF THE INVENTION

The present invention provides implantable devices, and systems and methods for deploying the implantable devices within the body.

The implant sites addressable by the subject devices may be any tubular or hollow tissue lumen or organ; however, the most typical implant sites are vascular structures, particularly the aorta. Thus, devices of the invention are constructed such that they can address implant sites involving two or more intersecting tubular structures and, as such, are particularly suitable in the context of treating vascular trees such as the aortic arch and the infrarenal aorta. As such, the implantable devices generally include a tubular member or lumen, most typically in the form of a stent, a graft or a stent graft, where the devices may further include one or more branching or transverse tubular members or lumens laterally extending from the main or primary tubular member.

The devices and their lumens are formed by interconnected cells where the cells are defined by struts which are preferably made of an elastic or superelastic material such that changes and adjustments can be made to various dimensions, orientations and shapes of the device lumens. As such, another feature of the present invention involves the reduction or expansion of a dimension, e.g., diameter and length, of one or more the device lumens. Typically, a change in one dimension is dependent upon or results in an opposite change in another dimension, i.e., when the diameter of the stent lumen is reduced, the length of the stent increases, and visa versa. The material construct of the devices further enables the one or more side branch lumens of the devices to be positioned at any appropriate location along the length of the main lumen and at any angle with respect to the longitudinal axis of the main lumen. Where there are two or more side branch lumens, the lumens may be spaced axially and circumferentially angled relative to each other to accommodate the target vasculature into which the implant is to be placed.

The systems of the present invention are particularly suitable for delivering and deploying the subject stent, graft or stent graft devices within a vessel or tubular structure within the body, particularly where the implant site involves two or more interconnecting vessels. In general, the delivery and deployment systems of the present invention enables independent control of each lumenal end of an implantable device, where "control" may involve one or more acts of delivering, positioning, placing, lengthening, foreshortening, expanding, and reducing a dimension of the device. The systems further include means for partially and/or fully deploying the implantable devices as well as repositioning the devices subsequent to at least partial deployment within the vasculature.

Such independent control and deployment capabilities are provided by the utilization of at least one element or member associated with the delivery system and releasably attached to each lumenal end. Each member is independently manipulatable relative to the other releasably attached members. As such, each lumenal end of the implantable device may be individually and independently deployed as desired, where some or all of the lumenal ends may be simultaneously deployed or they may be serially deployed in any order that best facilitates the implantation procedure.

In one variation, the elements include a collection of elongated members used to deploy the implantable devices where the elongated elements may take any suitable form including but not limited to strings, lines, filaments, fibers, wires, stranded cables, tubings, etc. where at least one elongated member is releasably attached to one, some or all of the lumenal ends of the implantable device. In one particular embodiment, a collection of strings is employed where a single string is provided for and used to control each of the proximal and distal ends of the main lumen and for each side branch lumen of the implantable device. In another embodiment, a set of strings is used for each lumenal end, where each set includes one string per apex of the device ends. The subject delivery systems include means for selectively tensioning or pulling each of the single or plurality of attachment strings or elongate members whereby the implantable device is selectively deployable by releasing the tension on the attachment strings.

In still other embodiments, something other than a string(s) or elongated member(s) is used to control and retain at least one of the lumenal ends. In one particular embodiment, the retention mechanism comprises a set of extensions, such as pins or hooks, extending from the distal end of a catheter or guidewire be associated with the delivery system. The extensions are used to engage the apices of a lumenal end in a releasable fashion to retain that lumenal end in an undeployed state. The extension members may be used in conjunction with a receptacle or the like which receives the ends of the members when the apices are "captured" by the retention.

There may be other means equally suitable for selective deployment of the implantable devices beyond the use of detachable strings. For example, similar to the use of detachable coils used in aneurysm repair, a current may be used to erode by electrolysis the connection point to the stent ends to facilitate a controlled release and deployment of the stent. Other means of releasable attachment which may be employed with the delivery systems to deploy the subject devices include but are not limited to thermal energy, magnetic means, chemical means, mechanical means or any other controllable detachment means. Irrespective of the type of deployment techniques used, selective deployment allows the implantable device to be partially deployable or deployable in increments or sections, where the implant may be entirely or partially exposed from the delivery system without being fully released/deployed at the implant site.

The implant delivery and deployment system in one embodiment includes a series of guidewires, a distal catheter portion and a proximal handle portion where the implantable device is loaded within the catheter portion prior to delivery to the target site. At least the catheter portion of the system is tracked over the one or more guidewires which direct and position the stent or stent-graft and each of its branches within their respective targeted vessels selected for implantation. Various controls are provided for the selective tensioning and release of the implant's luminal ends, where the controls may be located on the handle portion, the catheter portion or both. In a preferred embodiment, the catheter portion and/or the delivery guidewires are articulatable at their distal ends to facilitate navigation through the vasculature.

One embodiment of the system includes an articulating delivery guidewire or guiding catheter. The articulating guidewire may have one or more articulation points to allow an operator to change the shape of the distal portion of the guidewire by manipulation of the proximal portion of the guidewire. The guidewire can be preconfigured to change from a straight configuration into a range of various preselected shapes brought about by controlling individual articulation points during manipulation of the proximal portion of the guidewire. In this way, a guidewire may be produced to unique specifications for access to distinct areas of the vasculature. For example, this may be of particular importance in locating the implant within a region that requires an "S" shaped path from entry point to implant target site. Introduction of a guidewire through a femoral artery access point leading to an implant target in the innominate artery exemplifies one instance of a potentially difficult "S" shaped navigation pathway where such an articulating guidewire may be advantageous.

The methods of the present invention involve deploying the implantable device where certain of the methods involve the use of the subject systems. Methods for manufacturing the implantable devices are also provided.

Another objective of the invention is to provide a method of stent deployment which does not cause temporary occlusion of the vessel into which stent is to be placed.

Another objective of the invention is to provide a method of stent deployment using guidewires and an associated delivery system which enter the vasculature from a single access location.

An advantage of the stent delivery system of the present invention is that it does not require the use of space-occupying stylets and balloon catheters.

Another advantage of the subject system is that it allows for adjustment of the position or placement, as well as removal, of a stent during and after deployment thereof.

The present invention is additionally advantageous in that it provides a user with the ability to deploy a stent, to evaluate the suitability of the resulting deployment using standard imaging, such as by use of radiographic dye and fluoroscopy or any other imaging system, to check for endoleak between the covered stent wall and the surrounding arterial wall and to detach the stent from the delivery system upon adequate stent deployment or, in the case of an inadequate deployment, to either relocate the stent to a new location and obtain a satisfactory result by controlling the delivery and detachment of the stent in a repeatable manner, or to remove the stent entirely.

The present invention is additionally advantageous in that it secures the stent from migration within the vasculature by integrating the cells of the side branch lumen into the cells of the main body lumen such that, when the side branch lumens are deployed within their branch vessels, the main body lumen is constrained from migration by a "lock and key" mechanism. More specifically, the interconnection of the side branch lumen to the main body lumen is accomplished by forming the side branch lumen and the main body lumen from the same single wire where a specific wire wrap pattern is used to form a linking mesh to integrate the side branch lumen with the main lumen. Thus, when the side branch is deployed within and held in place by the side branch artery, the main body of the stent cannot migrate. Moreover, such a "passive" anchoring mechanism is atraumatic, as opposed to an active anchoring means, such as barbs or hooks, which may damage the cellular structures of the implant site leading to smooth muscle proliferation, restenosis, and other vascular complications.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Also for purposes of clarity, certain features of the invention may not be depicted in some of the drawings. Included in the drawings are the following figures:

FIGS. 8A-8H illustrate various steps of a method of the present invention for delivering a stent of the present invention using an implantation system of the present invention.

FIG. 10A illustrates a side view of an embodiment of an inner member of the catheter portion of the delivery and deployment system of the present invention. FIG. 10B illustrates a cross-sectional view of the inner member of FIG. 10A taken along the line B-B of FIG. 10A. FIG. 10C illustrates a cross-sectional view of the inner member of FIG. 10 taken along the line C-C of FIG. 10A.

FIGS. 12A-12F illustrate various steps of another method of the present invention for delivering a stent of the present invention using an implantation system of the present invention.

DETAILED DESCRIPTION OF THE INVENTION

Before the devices, systems and methods of the present invention are described, it is to be understood that this invention is not limited to particular therapeutic applications and implant sites described, as such may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The terms "proximal" and "distal" when used to refer to the delivery and deployment systems of the present invention are to be understood to indicate positions or locations relative to the user where proximal refers to a position or location closer to the user and distal refers to a position or location farther away from the user. When used with reference to the implantable devices of the present invention, these terms are to be understood to indicate positions or locations relative to a delivery and deployment system when the implantable devices is operatively positioned within the system. As such, proximal refers to a position or location closer to the proximal end of the delivery and deployment system and distal refers to a position or location closer to the distal end of the delivery and deployment system. The term "implant" or "implantable device" as used herein includes but is not limited to a device comprising a stent, a graft, a stent-graft or the like.

The present invention will now be described in greater detail by way of the following description of exemplary embodiments and variations of the devices, systems and methods of the present invention. The invention generally includes an implantable device which includes a tubular member in the form of a stent, a graft or a stent graft, where the device may further include one or more branching or transverse tubular members laterally extending from the main or primary tubular member. The invention farther includes a system for the percutaneous, endovascular delivery and deployment of the implantable device at a target implant site within the body. The implant site may be any tubular or hollow tissue lumen or organ; however, the most typical implant sites are vascular structures, particularly the aorta. A feature of the invention is that it addresses applications involving two or more intersecting tubular structures and, as such, is particularly suitable in the context of treating vascular trees such as the aortic arch and the infrarenal aorta.

Implantable Devices of the Present Invention

Figure 1A:
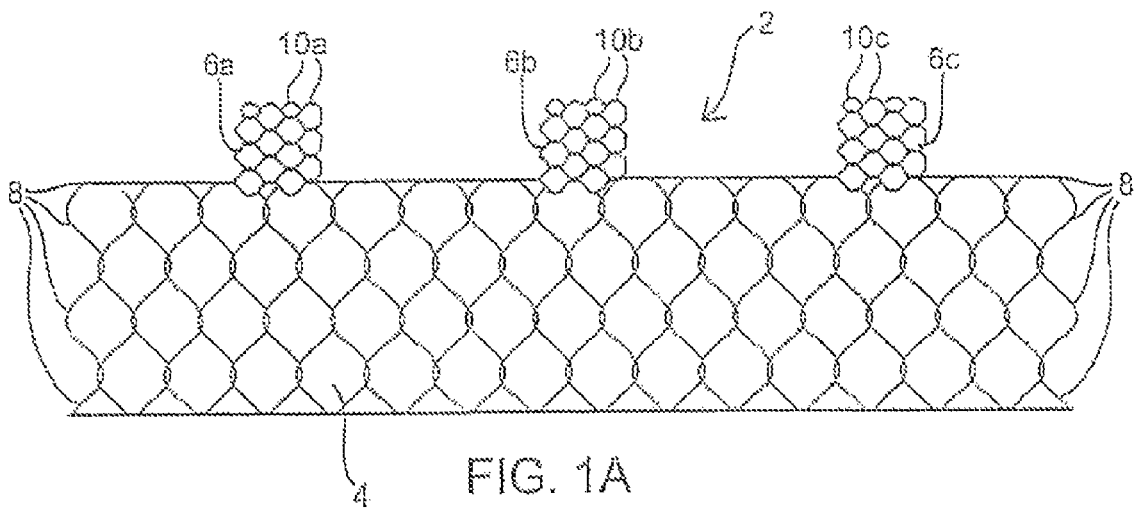
FIG. 1A illustrates an embodiment of an implant of the present invention in a natural, deployed state.
Figure 1B:
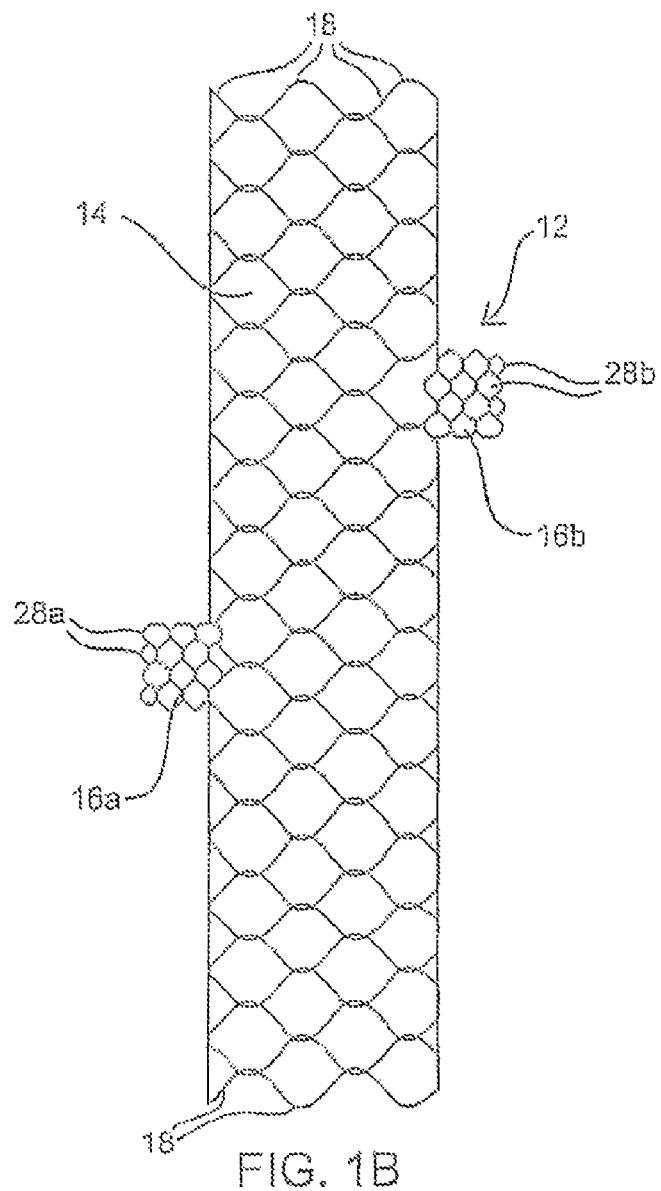
FIG. 1B illustrates another embodiment of an implant of the present invention in a natural, deployed state.

Referring now to the figures and to FIGS. 1A and 1B in particular, there are illustrated exemplary embodiments of implantable devices of the present invention. Each of the devices has a primary or main tubular member and at least one laterally extending tubular branch, however, the implantable devices of the present invention need not have side branches.

FIG. 1A illustrates one variation of an implantable device 2 having a primary tubular portion, body or member 4 and laterally extending side branches 6a, 6b and 6c, interconnected and in fluid communication with main body 4 by way of lateral openings within the body. The proximal and distal ends of the main tubular member 4 terminate in crowns or apexes 8, the number of which may vary. The distal ends of the side branches 6a, 6b and 6c terminate in crowns or apexes 10a, 10b and 10c, respectively, the number of which may also vary. Device 2 is particularly configured for implantation in the aortic arch where primary tubular member 4 is positionable within the arch walls and tubular branches 6a, 6b and 6c are positionable within the innominate artery, the left common carotid artery and the left subclavian artery, respectively.

As will be described in greater detail below, the deployment or attachment members of the subject delivery and deployment systems, are looped through the apexes 10a, 10b and 10c, or through eyelets (not shown) extending from the distal ends of the apexes of the device 2. The attachment members of the present invention may be any elongated member including but not limited any strings, filaments, fibers, wires, stranded cables, tubings or other elongated member which are releasably attachable to the distal ends of the various lumens of the stent. Means of releasable attachment include but are not limited to electrolytic erosion, thermal energy, magnetic means, chemical means, mechanical means or any other controllable detachment means.

FIG. 1B illustrates another variation of a device 12 having a primary tubular portion or member 14 and laterally extending branches 16a and 16b, interconnected and in fluid communication with main body 14 by way of lateral openings within the body. The proximal and distal ends of the main tubular member 14 terminate in crowns or apexes 18 which are employed as described above with respect to FIG. 1A while the distal ends of the side branches 16a and 16b terminate in crowns or apexes 18a and 18b, respectively. Device 12 is particularly configured for implantation in the infra-renal aorta where primary tubular member 14 is positionable within the walls of the aorta and tubular branches 16a and 16b are positioned within the right and left renal arteries, respectively.

Those skilled in the art will recognize that the subject implants may have any number and configuration of lumens (e.g., a single main lumen without side branch lumens, a main lumen and one or more side branch lumens) where the one or more side branch lumens may be positioned at any appropriate location along the length of the main lumen and at any angle with respect to the longitudinal axis of the main lumen, and where the there are two or more side branch lumens, the lumens may be spaced axially and circumferentially angled relative to each other to accommodate the target vasculature into which the implant is to be placed. Additionally, the length, diameter and shape (e.g., radius of curvature) of each of the implant's lumens may vary as needed to accommodate the vessel into which it is positioned. . In certain applications, particularly where treating a vascular aneurysm having a relatively large neck section located near a juncture between the main vessel and a tributary vessel, it may be preferential to provide a branched stent where the side branch lumens are relatively longer than average. The lengthier stent branches can bridge the neck opening while maintaining sufficient length at their distal ends to extend a distance into a vascular side branch sufficient to anchor the stent.

Typically, the subject devices for most vascular applications will have a main branch lumen having an unconstrained length in the range from about 1 cm to about 25 cm and an unconstrained diameter in the range from about 2 mm to about 42 mm; and side branch lumens having an unconstrained length in the range from about 0.5 cm to about 8 cm and an unconstrained diameter in the range from about 2 mm to about 14 mm. For aortic applications, the unconstrained length of the main lumen is typically from about 8 cm to about 25 cm and the unconstrained diameter is in the range from about 15 mm to about 42 mm; and the side branch lumens will have an unconstrained length in the range from about 2 cm to about 8 cm and an unconstrained diameter in the range from about 5 mm to about 14 mm. Where the dimension is the diameter of the main lumen of the stent, the reduced diameter is more likely to be closer to one tenth of the unreduced diameter. For renal applications, the main branch lumen will have an unconstrained length in the range from about 2 cm to about 20 cm and an unconstrained diameter in the range from about 12 mm to about 25 mm; and the side branch lumens will have an unconstrained length in the range from about 0.5 cm to about 5 cm and an unconstrained diameter in the range from about 4 mm to about 12 mm. For coronary applications, the main branch lumen will have an unconstrained length in the range from about 1 cm to about 3 cm and an unconstrained diameter from about 2 mm to about 5 mm; and the side branch lumens will have an unconstrained length in the range from about 0.5 cm to about 3 cm and an unconstrained diameter in the range from about 2 mm to about 5 mm. For applications in smaller vessels, such as the neurovasculature, these dimensions will of course be smaller. In certain applications, particularly where treating a vascular aneurysm having a relatively large neck section located near a juncture between the main vessel and a tributary vessel, it may be preferential to provide a branched stent where the side branch lumens are relatively longer than average. The lengthier stent branches can bridge the neck opening while maintaining sufficient length at their distal ends to extend a distance into a vascular side branch sufficient to anchor the stent.

It is also contemplated that therapeutic or diagnostic components or devices may be integrated with the subject implants. Such devices may include but are not limited to prosthetic valves, such as cardiac valves (e.g., an aortic or pulmonary valve) and venous valves, sensors to measure flow, pressure, oxygen concentration, glucose concentration, etc., electrical pacing leads, etc. For example, as illustrated in FIG. 1E, an implant 210 for treating the aortic root is provide which includes a mechanical or biological prosthetic valve 216 employed at a distal end of the main lumen 212. Device 210 further includes two smaller, generally opposing side branch lumens 214a and 214b adjustably aligned for placement within the right and left coronary ostia, respectively. The length of the stent graft may be selected to extend to a selected distance where it terminates at any location prior to, within or subsequent to the aortic arch, e.g., it may extend into the descending aorta. Any number of additional side branches may be provided for accommodating the aortic arch branch vessels.

Those skilled in the art will appreciate that any suitable stent or graft configuration may be provided to treat other applications at other vascular locations at or near the intersection of two or more vessels (e.g., bifurcated, trifurcated, quadrificated, etc.) including, but not limited to, the aorto-illiac junction, the femoral-popiteal junction, the brachycephalic arteries, the posterior spinal arteries, coronary bifurcations, the carotid arteries, the superior and inferior mesenteric arteries, general bowel and stomach arteries, cranial arteries and neurovascular bifurcations.

The stents and grafts of the present invention may be made of any suitable materials known in the art. Preferably, the stent is constructed of wire, although any suitable material may be substituted. The wire stent should be elastically compliant, for example, the stent may be made of stainless steel, elgiloy, tungsten, platinum or nitinol but any other suitable materials may be used instead of or in addition to these commonly used materials.

The stents may have any suitable wire form pattern or may be cut from a tube or flat sheet. In one embodiment, the entire stent structure is fabricated from a single wire woven into a pattern of interconnected cells forming, for example, a closed chain link configuration. The structure may have a straight cylindrical configuration, a curved tubular configuration, a tapered hollow configuration, have asymmetrical cell sizes, e.g., cell size may vary along the length or about the circumference of the stent. In certain stent embodiments, the cell size of the side branches lumens is gradually reduced in the distal direction. This further facilitates the ability to selectively stretch the distal most portion of the side branch lumens and, thus, making it easier for a physician to guide the distal end of the side branch into a designated vessel. The ends of the main stent lumen and/or the end of one or more side branch stent lumens may be flared. The struts of the stent (i.e., the elemental portions that form a cell) may vary in diameter (in wire embodiments) or thickness or width (in sheet and cut tube embodiments).

In one particular embodiment, the stent is configured from a single-wire. The single-wire stent configuration is advantageous in that through selective interlacing of the connection points along the length of the stent, it provides for adjustability in the angular orientation of the side branch stents relative to each other and relative to the main stent lumen within a selected range that can accommodate any possible variation in the anatomy being treated. Such angular orientation of the side branch lumens may be axial, circumferential or both.

Figure 1C:
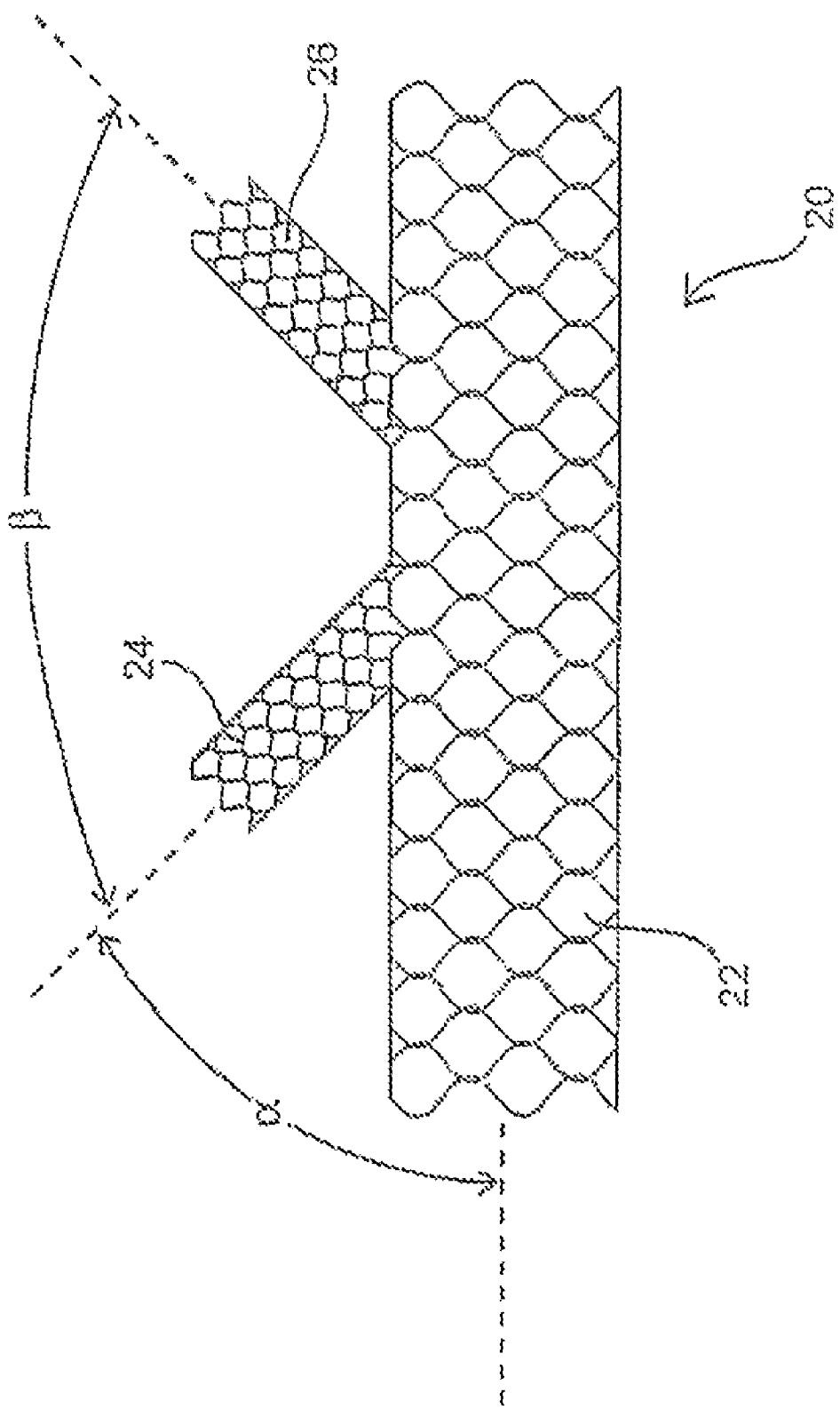
FIG. 1C illustrates another embodiment of an implant in which the side branch lumens are angled.
Figure 1D:
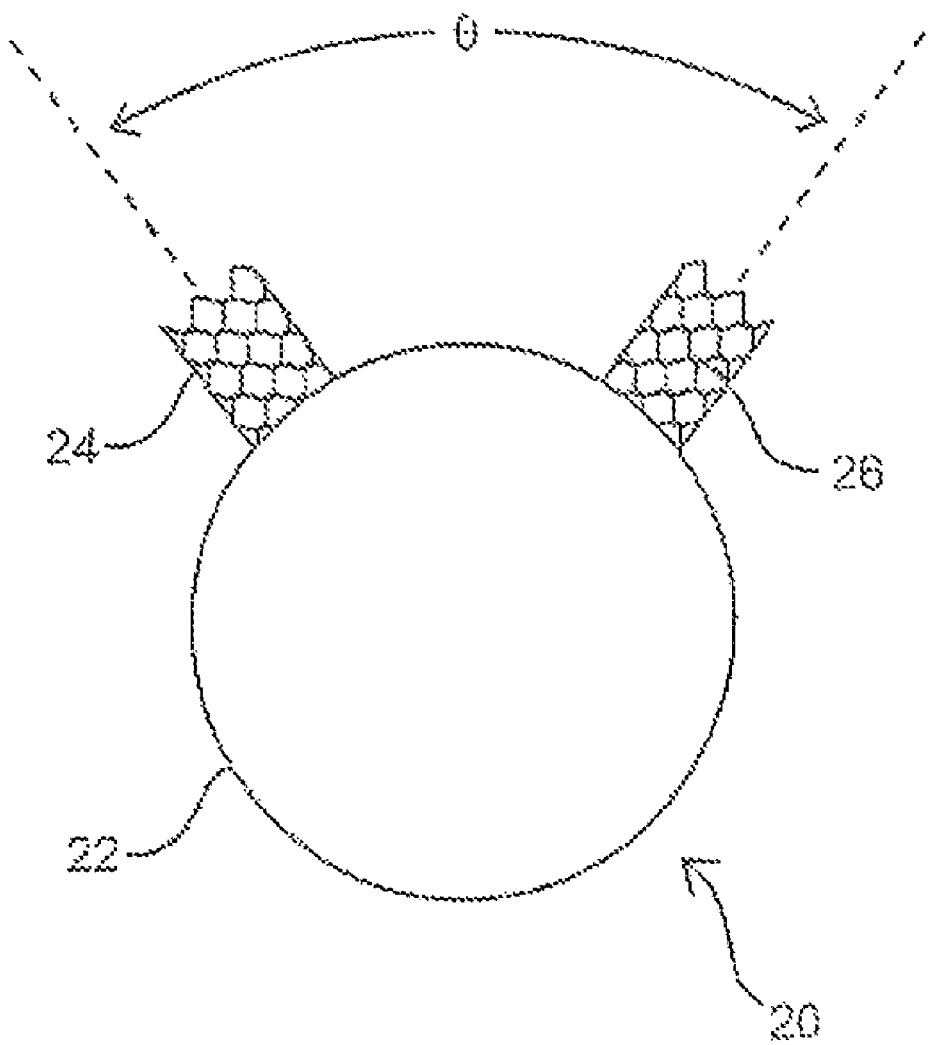
FIG. 1D illustrates an end view of the implant of FIG. 1C.
Figure 1E:
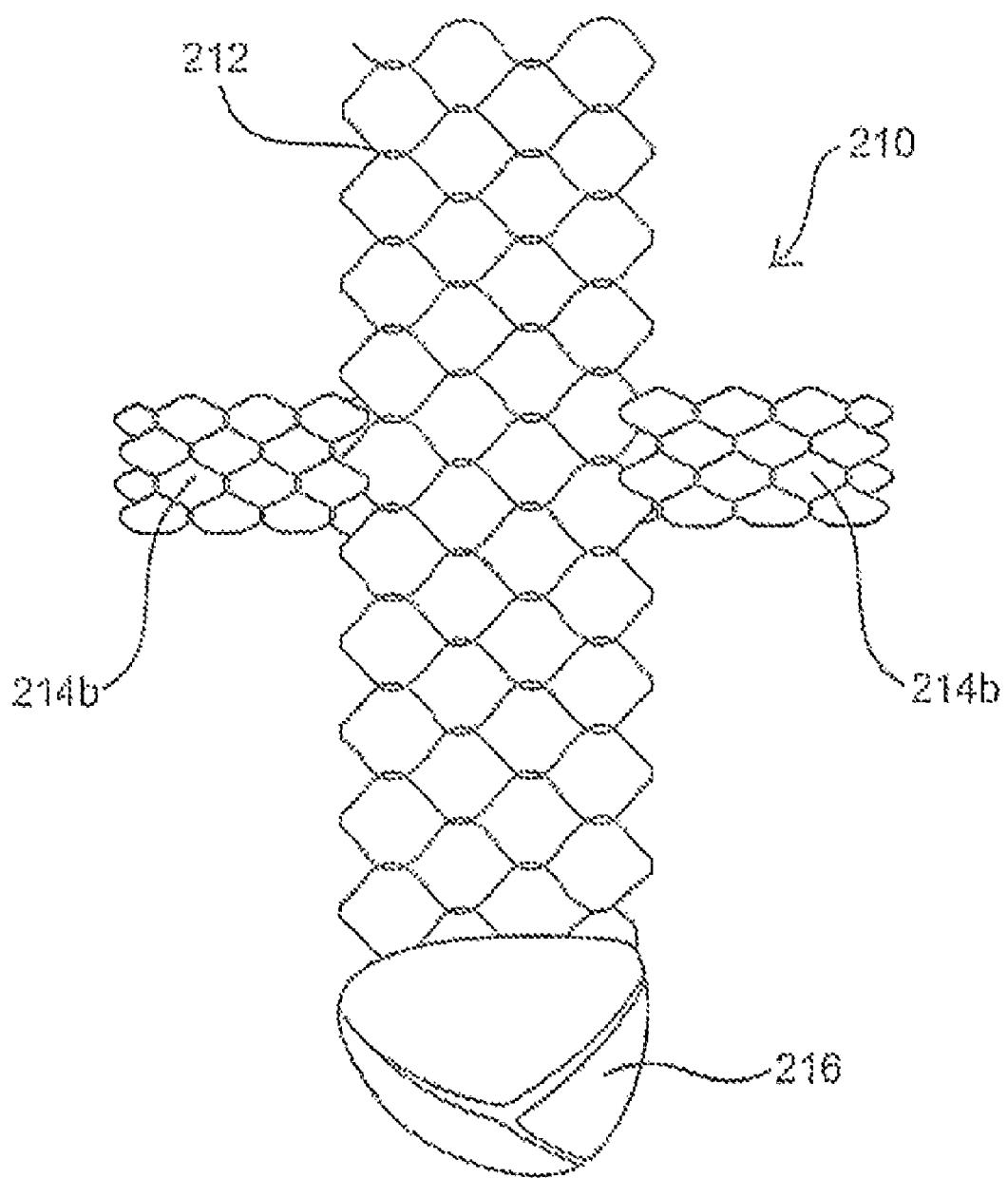
FIG. 1E illustrates another embodiment of an implant of the present invention having a cardiac valve operatively coupled to it.

FIG. 1C illustrates an implant device 20 in which side branch lumens 24 and 26 each has an angular orientation, defined by angle α, with respect to main lumen 22, and have an angular orientation, defined by angle β, with respect to each other. FIG. 1D is an end view of implant device 20 which illustrates the circumferential orientation, defined by angle θ, between side branch lumens 22 and 24. Typical ranges of the various angles are as follows: from about 10° to about 170° for angle α, from 0° to about 170° for angle β, and from 0° to 360° for angle θ. These orientations may be provided by the fabrication process resulting in a stent which has naturally biased orientations in an unconstrained, pre-deployed condition, i.e., the neutral state. One or more of these orientations may be selectively adjusted within the angle ranges provided above upon delivery and placement of the branch lumens within the respective vessel lumens. This design also allows for adjustability in the linear spacing between the side branch stents by stretching and/or foreshortening of the main lumen of the stent. Further, the side branch portions can be elongated to allow for placement of an oversized stent in a smaller branch vessel thereby providing adequate apposition between the stent and the vessel wall. It should be noted that the adjustability of the stent does not compromise the radial force needed to fixate or anchor and prevent migration and endoleak of the device.

The subject devices may also be fabricated such that their lumens may have constant or variable stiffness/flexibility along their lengths as well as about their circumferences. Greater flexibility can better accommodate curvaceous vasculature encountered during delivery and at the implant site. Such a feature is highly beneficial in aortic arch stenting applications due to the relatively "tight" curve of the arch. Enhanced stiffness, on the other hand, particularly at the end portions of a lumen, imparts a greater radial force thereby resisting migration of the device within the vasculature after placement. Variable flexibility/stiffness may be implemented in a variety of ways.

The gauge or thickness of the strut or struts (i.e., the elemental portions that form a stent cell) used to fabricate the devices may vary where thicker gauges impart greater stiffness and thinner gauges impart greater flexibility. The struts of a stent may vary in diameter (in wire embodiments) or thickness or width (in sheet and cut tube embodiments). In one variation, a single wire or filament may be used where the gauge selectively varies along its length. The thicker gauge portions are used to form at least the end portions of the stent lumen(s) to increase their radial force thereby reducing the risk of stent migration. Conversely, the narrower gauge portion(s) of the wire form at least a central portion of the main stent lumen (and portions of the side branch lumens) which may be relatively more flexible than the end portions to facilitate delivery of the stent within tortuous or curving vasculature or enabling the device to be compact into the delivery sheath more easily. For aortic stenting applications, this may be accomplished by a wire having one to two centimeter portions at each of its ends having a larger diameter than the remaining central portion. Another example of selectively reducing the wire cross sectional diameter is to make the struts of the side branch stents smaller in diameter.

In other embodiments, more than one wire is used where the wires each have constant gauges along their respective lengths but differ from wire to wire. Larger gauge wire(s) may be used to form the stent ends or other areas where increased stiffness is required while narrower gauge wire(s) may be used to form other portions, e.g., the central portions of the stent lumens, where increased flexibility is required. Additionally or alternatively, the larger gauge wire can be selectively doubled-over or wrapped with the narrow gauge wire at selected points or locations about the stent to bolster the stiffness at those particular sites.

In one variation, two or more wires may be employed to form the device whereby the wire ends, i.e., four wire ends in the case of a device made from two wires, are joined together. The location(s) about the lumen s at which the wires cross-each and/or at which their ends are joined about is/are selected to minimize stiffness in certain areas along or about the lumen and/or to enhance stiffness in one or more other areas of the device, i.e., to provide relative stiffness and flexibility between portions of the stent. For example, in aortic arch applications, the portion of the main lumen of the stent intended to be aligned along the inferior wall of the arch is preferentially relatively more flexible and/or less stiff than the portion of the stent intended to be aligned along the superior wall of the arch, as the inferior wall has a tighter radius of curvature. Accordingly, it may be desirable to minimize the joinder and/or intersection points of the wires along this portion of the stent.

It may also be desirable to provide greater stiffness at the juncture between the main lumen and side branch lumens. Aortic aneurysms, and particularly aneurysms located at the intersection of the aortic arch and one or more of its tributary vessels, can result in relatively large volumes of not-so-defined perimeters, i.e., "sacks", within the vasculature. Without a vessel wall against which to buttress itself, a stent juncture may be more susceptible to kinking. Stiffening the stent's juncture points can prevent such kinking.

Co-pending U.S. patent application entitled Vascular Implants and Methods of Fabricating the Same filed Oct. 6, 2006 and incorporated herein by reference, discloses stent devices having many of the features for selectively enhancing the stiffness and flexibility properties described above.

As mentioned above, the implantable devices of the present invention may include a stent or a graft or a combination of the two, referred to as a stent graft, a stented graft or a grafted stent. The graft portion of a stent graft may be made from a textile, polymer, latex, silicone latex, polyetraflouroethylene, polyethylene, Dacron polyesters, polyurethane or other or suitable material such as biological tissue. The graft material must be flexible and durable in order to withstand the effects of installation and usage. One of skill in the art would realize that grafts of the subject invention may be formulated by many different well known methods such as for example, by weaving or formed by dipping a substrate in the desired material.

Biological tissues that may be used to form the graft material (as well as the stent) include, but are not limited to, extracellular matrices (ECMs), acellularized uterine wall, decellularized sinus cavity liner or membrane, acellular ureture membrane, umbilical cord tissue, decelluarized pericardium and collagen. Suitable ECM materials are derived from mammalian hosts sources and include but are not limited to small intestine submucosa, liver basement membrane, urinary bladder submucosa, stomach submucosa, the dermis, etc. Extracellular matrices suitable for use with the present invention include mammalian small intestine submucosa (SIS), stomach submucosa, urinary bladder submucosa (UBS), dermis, or liver basement membranes derived from sheep, bovine, porcine or any suitable mammal.

Submucosal tissues (ECMs) of warm-blooded vertebrates are useful in tissue grafting materials. Submucosal tissue graft compositions derived from small intestine have been described in U.S. Pat. No. 4,902,508 (hereinafter the '508 patent) and U.S. Pat. No. 4,956,178 (hereinafter the '178 patent), and submucosal tissue graft compositions derived from urinary bladder have been described in U.S. Pat. No. 5,554,389 (hereinafter the '389 patent). All of these (ECMs) compositions are generally comprised of the same tissue layers and are prepared by the same method, the difference being that the starting material is small intestine on the one hand and urinary bladder on the other. The procedure detailed in the '508 patent, incorporated by reference in the '389 patent and the procedure detailed in the '178 patent, includes mechanical abrading steps to remove the inner layers of the tissue, including at least the lumenal portion of the tunica mucosa of the intestine or bladder, i.e., the lamina epithelialis mucosa (epithelium) and lamina propria, as detailed in the '178 patent. Abrasion, peeling, or scraping the mucosa delaminates the epithelial cells and their associated basement membrane, and most of the lamina propria, at least to the level of a layer of organized dense connective tissue, the stratum compactum. Thus, the tissue graft material (ECMs) previously recognized as soft tissue replacement material is devoid of epithelial basement membrane and consists of the submucosa and stratum compactum.

Examples of a typical epithelium having a basement membrane include, but are not limited to the following: the epithelium of the skin, intestine, urinary bladder, esophagus, stomach, cornea, and liver. The epithelial basement membrane may be in the form of a thin sheet of extracellular material contiguous with the basilar aspect of epithelial cells. Sheets of aggregated epithelial cells of similar type form an epithelium. Epithelial cells and their associated epithelial basement membrane may be positioned on the lumenal portion of the tunica mucosa and constitute the internal surface of tubular and hollow organs and tissues of the body. Connective tissues and the submucosa, for example, are positioned on the abluminal or deep side of the basement membrane. Examples of connective tissues used to form the ECMs that are positioned on the abluminal side of the epithelial basement membrane include the submucosa of the intestine and urinary bladder (UBS), and the dermis and subcutaneous tissues of the skin. The submucosa tissue may have a thickness of about 80 micrometers, and consists primarily (greater than 98%) of a cellular, eosinophilic staining (H&E stain) extracellular matrix material. Occasional blood vessels and spindle cells consistent with fibrocytes may be scattered randomly throughout the tissue. Typically the material is rinsed with saline and optionally stored in a frozen hydrated state until used.

Fluidized UBS, for example, can be prepared in a manner similar to the preparation of fluidized intestinal submucosa, as described in U.S. Pat. No. 5,275,826 the disclosure of which is expressly incorporated herein by reference. The UBS is comminuted by tearing, cutting, grinding, shearing or the like. Grinding the UBS in a frozen or freeze-dried state is preferred although good results can be obtained as well by subjecting a suspension of submucosa pieces to treatment in a high speed (high shear) blender and dewatering, if necessary, by centrifuging and decanting excess water. Additionally, the comminuted fluidized tissue can be solubilized by enzymatic digestion of the bladder submucosa with a protease, such as trypsin or pepsin, or other appropriate enzymes for a period of time sufficient to solubilize said tissue and form a substantially homogeneous solution.

The coating for the stent may be powder forms of UBS. In one embodiment a powder form of UBS is prepared by pulverizing urinary bladder submucosa tissue under liquid nitrogen to produce particles ranging in size from 0.1 to 1 mm$^2$. The particulate composition is then lyophilized overnight and sterilized to form a solid substantially anhydrous particulate composite. Alternatively, a powder form of UBS can be formed from fluidized UBS by drying the suspensions or solutions of comminuted UBS.

Other examples of ECM material suitable for use with the present invention include but are not limited to fibronectin, fibrin, fibrinogen, collagen, including fibrillar and non-fibrillar collagen, adhesive glycoproteins, proteoglycans, hyaluronan, secreted protein acidic and rich in cysteine (SPARC), thrombospondins, tenacin, and cell adhesion molecules, and matrix metalloproteinase inhibitors.

The stent may be processed in such a way as to adhere an ECM covering (or other material) to only the wire, and not extend between wire segments or within the stent cells. For instance, one could apply energy in the form of a laser beam, current or heat to the wire stent structure while the ECM has been put in contact with the underlying structure. Just as when cooking meat on a hot pan leaves tissue, the ECM could be applied to the stent in such a manner.

Subsequent to implant of the subject devices, the ECM portion of the implant is eventually resorbed by the surrounding tissue, taking on the cellular characteristics of the tissue, e.g., endothelium, smooth muscle, adventicia, into which it has been resorbed. Still yet, an ECM scaffolding having a selected configuration may be operatively attached to a stent or stent graft of the present invention at a selected location whereby the ECM material undergoes subsequent remodeling to native tissue structures at the selected location. For example, the ECM scaffolding may be positioned at the annulus of a previously removed natural aortic valve configured in such a way as to create the structural characteristics of aortic valve leaflets and whereby the implant provides valve function.

The subject stents, grafts and/or stent grafts may be coated in order to provide for local delivery of a therapeutic or pharmaceutical agent to the disease site. Local delivery requires smaller dosages of therapeutic or pharmaceutical agent delivered to a concentrated area; in contrast to systemic dosages which require multiple administrations and loss of material before reaching the targeted disease site. Any therapeutic material, composition or drug, may be used including but not limited to, dexamethasone, tocopherol, dexamethasone phosphate, aspirin, heparin, coumadin, urokinase, streptokinase and TPA, or any other suitable thrombolytic substance to prevent thrombosis at the implant site. Further therapeutic and pharmacological agents include but are not limited to tannic acid mimicking dendrimers used as submucosa stabilizing nanomordants to increase resistance to proteolytic degradation as a means to prevent post-implantational aneurysm development in decellularized natural vascular scaffolds, cell adhesion peptides, collagen mimetic peptides, hepatocyte growth factor, proliverative/antimitotic agents, paclitaxel, epipidophyllotoxins, antibiotics, anthracyclines, mitoxantrone, bleomycins, plicamycin, and mitomycin, enzymes, antiplatelet agents, non-steroidal agents, heteroaryl acetic acids, gold compounds, immunosuppressives, angiogenic agents, nitric oxide donors, antisense oligonucleotides, cell cycle inhibitors, and protease inhibitors.

For purposes of agent delivery, the subject stents, grafts and/or stent grafts are coated with a primer layer onto a surface. The primer layer formulates a reservoir for containing the therapeutic/pharmaceutical agent. The overlapping region between the primer layer and active ingredient may be modified to increase the permeability of the primer layer to the active ingredient. For example, by applying a common solvent, the active ingredient and the surface layer mix together and the active ingredient gets absorbed into the primer layer. In addition, the primer layer may also be treated to produce an uneven or roughened surface. This rough area entraps the active ingredient and enhances the diffusion rate of the ingredient when the stent is inserted into the patient's body. As such, the implant has the ability to diffuse drugs or other agents at a controllable rate. Furthermore, one of skill in the art would understand that the subject invention may provide a combination of multiple coatings, such as the primer layer may be divided into multiple regions, each containing a different active ingredient.

The subject implants may also be seeded with cells of any type including stem cells, to promote angiogenesis between the implant and the arterial walls. Methods have included applying a porous coating to the device which allows tissue growth into the interstices of the implant surface. Other efforts at improving host tissue ingrowth capability and adhesion of the implant to the host tissue have involved including an electrically charged or ionic material in the tissue-contacting surface of the device.

The stent, graft, or stent graft of the present invention may also include a sensor or sensors to monitor pressure, flow, velocity, turbidity, and other physiological parameters as well as the concentration of a chemical species such as for example, glucose levels, pH, sugar, blood oxygen, glucose, moisture, radiation, chemical, ionic, enzymatic, and oxygen. The sensor should be designed to minimize the risk of thrombosis and embolization. Therefore, slowing or stoppage of blood flow at any point within the lumen must be minimized. The sensor may be directly attached to the outer surface or may be included within a packet or secured within the material of the stent, graft, or stent graft of the present invention. The biosensor may further employ a wireless means to deliver information from the implantation site to an instrument external to the body.

The stent, graft or stent graft may be made of visualization materials or be configured to include marking elements, which provide an indication of the orientation of the device to facilitate proper alignment of the stent at the implant site. Any suitable material capable of imparting radio-opacity may be used, including, but not limited to, barium sulfate, bismuth trioxide, iodine, iodide, titanium oxide, zirconium oxide, metals such as gold, platinum, silver, tantalum, niobium, stainless steel, and combinations thereof. The entire stent or any portion thereof may be made of or marked with a radiopaque material, i.e., the crowns of the stent.

Device Fabrication Methods

Figure 13A:
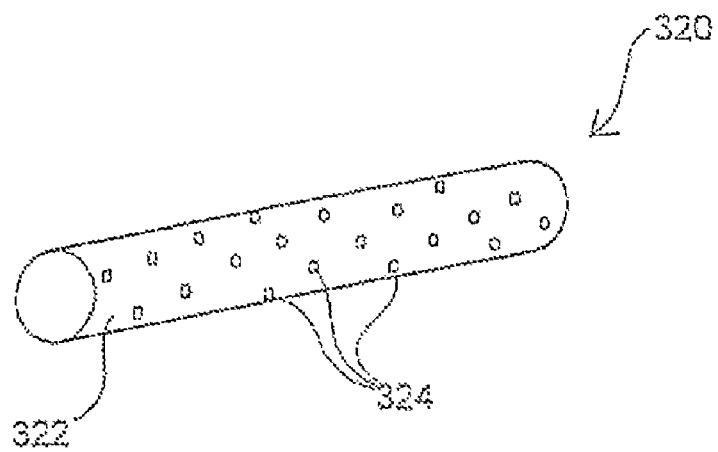
FIGS. 13A-13C illustrate various exemplary mandrel designs for fabricating the stents and stent grafts of the present invention.
Figure 13B:
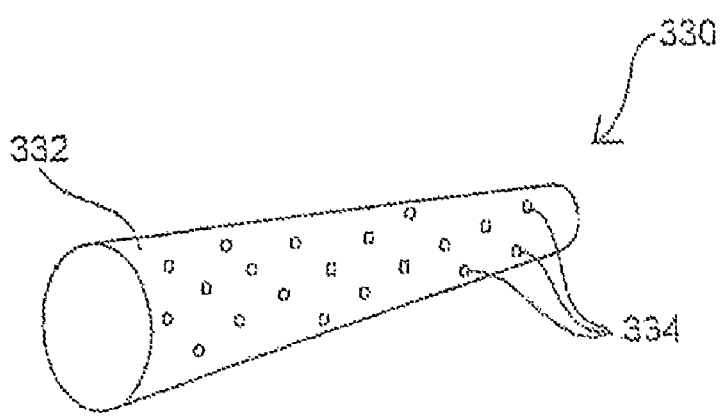
Figure 13C:
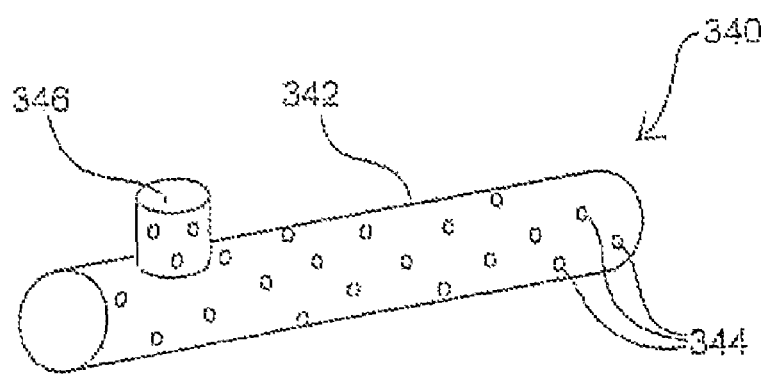

The stent of the present invention may be fabricated in many ways. One method of making the stent is by use of a mandrel device such as the mandrel devices 320, 330 and 340 illustrated in FIGS. 13A-13C, respectively. Each of the devices has at least a main mandrel component 322, 332 and 342, respectively, with a plurality of selectively positioned pinholes 324, 334 and 344, respectively, within which a plurality of pins (not shown) are selectively positioned, or from which a plurality of pins is caused to extend. As is described in more detail below, the stent structure is formed by selectively wrapping a wire around the pins. Where the stent is to have one or more side branch lumens, the mandrel device, such as device 340, may be provided with at least one side mandrel 346 extending substantially transverse to the main mandrel 342, where the number of side mandrels preferably corresponds to the number of stent side branches to be formed. The mandrel devices may be modular where side branch mandrels of varying diameters and lengths can be detachably assembled to the main mandrel. The configuration of the main mandrel as well as the side branch mandrel(s) may have any suitable shape, size, length, diameter, etc. to form the desired stent configuration. Commonly, the mandrel components have a straight cylindrical configuration (see FIGS. 13A and 13C) having a uniform cross-section, but may be conical with varying diameters along a length dimension (see FIG. 13B), frustum conical, have an oval cross-section, a curved shape, etc.

The pins may be retractable within the mandrel components or are themselves removable from and selectively positionable within holes formed in the mandrel components. Still yet, the mandrel device may be configured to selectively extend and retract the pins. The number of pins and the distance and spacing between them may be varied to provide a customized pin configuration. This customization enables the fabrication of stents having varying sizes, lengths, cell sizes, etc. using a limited number of mandrel components. For example, in one variation, the pins are arranged about the mandrel components in an alternating pattern such as for example, where four out of eight pin holes per row will be filled with pins. Alternatively, a selection of mandrels may be provided, each having a unique pinhole pattern which in turn defines a unique stent cell pattern.

To form the stent, a shape memory wire, such as a NITINOL wire, having a selected length and diameter are provided. Typically, the length of the wire ranges from about 9 to about 12 feet long, but may be longer if needed or shorter if more practical. The wire's diameter is typically in the range from about 0.001 to about 0.020 inch. After providing a mandrel device having winding pins at the desired points or locations on the mandrel components, the wire is wound about the pins in a selected direction and in a selected over-and-under lapping pattern, e.g., a zigzag pattern, to form a series of interconnected undulated rings resulting in a desired cell pattern.

Figure 14:
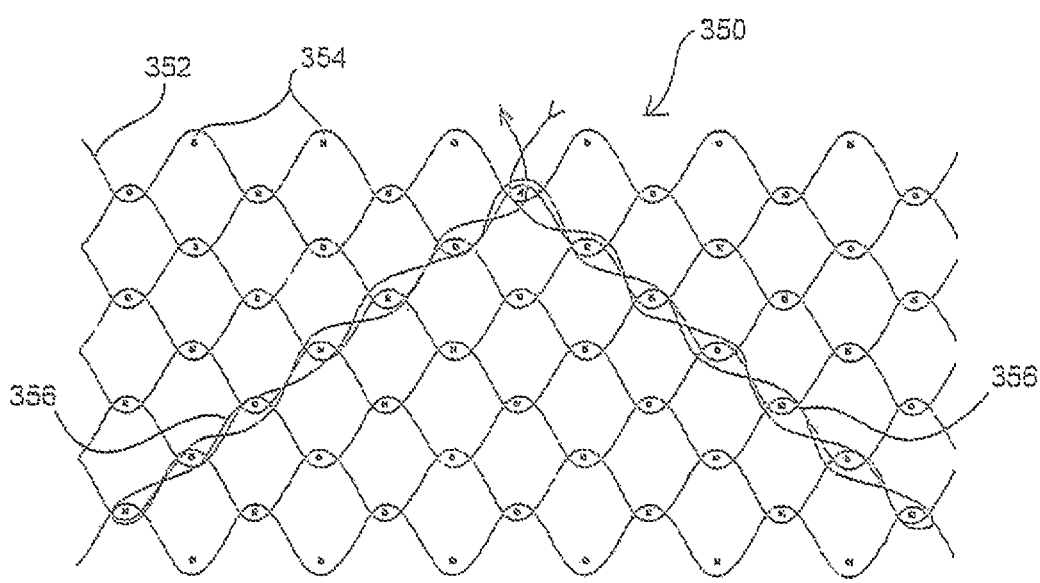
FIG. 14 illustrates an exemplary wire winding pattern to form a stent of the present invention.
Figure 15:
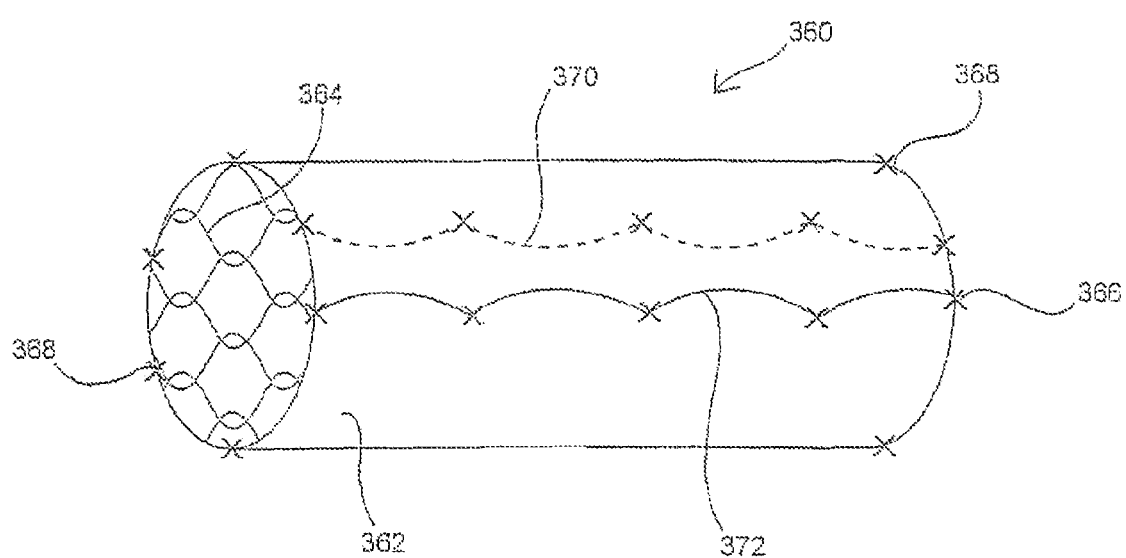
FIG. 15 illustrates one manner in grafting a stent of the present invention.

An exemplary wire winding pattern 350 is illustrated in FIG. 14. Starting from one end of the main mandrel, the wire 352 is wound around the pins 354 in a zigzag pattern back and forth from one end of the main mandrel to the other until the cells of the main lumen of the stent have been formed. Next, the same wire, still attached to the mandrel device, is used to form the side branch lumen(s) where the wire is wrapped in a zigzag fashion from the base of the side branch mandrel to the distally extending end and back again until all of the cells of the side branch have been created. Then the wire is wound about the main mandrel along a path that is at an angle to longitudinal axis of the main mandrel where the wire is doubled over itself along certain cell segments 356. It should be noted that any lumen of the stent may be fabricated first, followed by the others, or the winding pattern may be such that portions of the various lumens are formed intermittently.

The mandrel device with the formed wire stent pattern are then heated to a temperature in the range from about 480° C. to about 520° C. and typically to about 490° C. for approximately 20 minutes, however, this time may be reduced by using a salt bath. The duration of the heat-setting step is dependent upon the time necessary to shift the wire material from a Martensitic to an Austenitic phase. The assembly is then air cooled or placed into a water bath to quench for 30 seconds or more and then allowed to air dry. Once the stent is sufficiently dried, the pins are either pulled from the mandrel device or retracted into the hollow center of the mandrel by an actuation of an inner piece which projects the pins out their respective holes in the outer surface of the mandrel. The stent with its interconnected lumens can then be removed from the mandrel device. Alternatively, with the mandrel components detached from one another, one of the lumens, e.g., the main stent lumen, may be formed first followed by formation of a side branch lumen after attachment of a side mandrel to the main mandrel.

Optionally, selected regions of the main body or the portions of the wire forming the side branch lumen cells may be selectively reduced in diameter by etching or e-polishing so as to exert less radial force than that wire portion of the stent that has not been reduced in wire diameter. One example of a selective reduction of wire diameter in the main body of the stent is to leave a one to two centimeter circumferential portion on each of the proximal and distal ends to allow high radial force at those regions to secure the stent from migration while the center portion between those high radial force regions can be reduced in cross sectional wire diameter in order to facilitate stretching the stent more easily during placement or allowing it to compact into the delivery sheath more easily over a long length. Another example of selectively reducing the wire cross sectional diameter is to make the struts of the side branch smaller in diameter. This can be done by selective immersion of the side branch in an acid during manufacture to reduce the amount of metal in a particular region of the stent. Another method to accomplish the desired result of preferentially reducing side branch longitudinal stiffness and/or outward radial force of the side branch component is to use an electropolishing apparatus. By placing the woven solid wire stent into an electrolyte bath and applying a voltage potential across an anode-cathode gap, where the stent itself is the anode, metal ions are dissolved into the electrolytic solution. Alternatively, or subsequently, the process may be reversed wherein the stent becomes the cathode and the side branch or other selected region of the stent may be electroplated with a similar or different metal in ionic solution, for instance gold or platinum, in order to either change the mechanical properties or to enhance the radiopacity of the selected region. Those skilled in the art of electroplating and electropolishing will recognize that there are techniques using a "strike" layer of a similar material to the substrate in order to enhance the bonding of a dissimilar material to the substrate. An example would be the use of a pure nickel strike layer on top of a nickel titanium (NITINOL) substrate in order to subsequently bond a gold or platinum coating to the substrate.

Another method of making the stent is to cut a thin-walled tubular member, such as stainless steel tubing, to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum.

In accordance with the invention, one of skill in the art would know that several different methods may be employed to make the subject stents such as using different types of lasers; chemical etching; electric discharge machining; laser cutting a flat sheet and rolling it into a cylinder; all of which are well known in the art at this time.

Where a stent graft 360 is to be formed by the addition of a graft material 362, such as an ECM, to the subject stent 364, any manner of attaching the graft material to the wire form may be used. In one variation, the graft material is attached by way of a suture 366. As such, one edge 370 of the graft material is stitched lengthwise to the stent frame along the stents length, where at least one knot 368 is tied at each apex of the stent to secure an end of the graft to the stent. Then the graft material is stretch around the surface of the stent and the opposite edge 372 of the graft is overlapped with the already attached edge 370 and independently stitched to the stent frame to provide a leak free surface against which blood cannot escape. The graft material is stretched to an extent to match the compliance of the stent so that it does not drape when the stent is in the expanded state. Upon complete attachment of the graft material to the stent, the graft is dehydrated so that it snuggly shrinks onto the stent frame similar to heat shrink tubing would when heated.

Delivery and Deployment Systems of the Present Invention

Figure 2A:
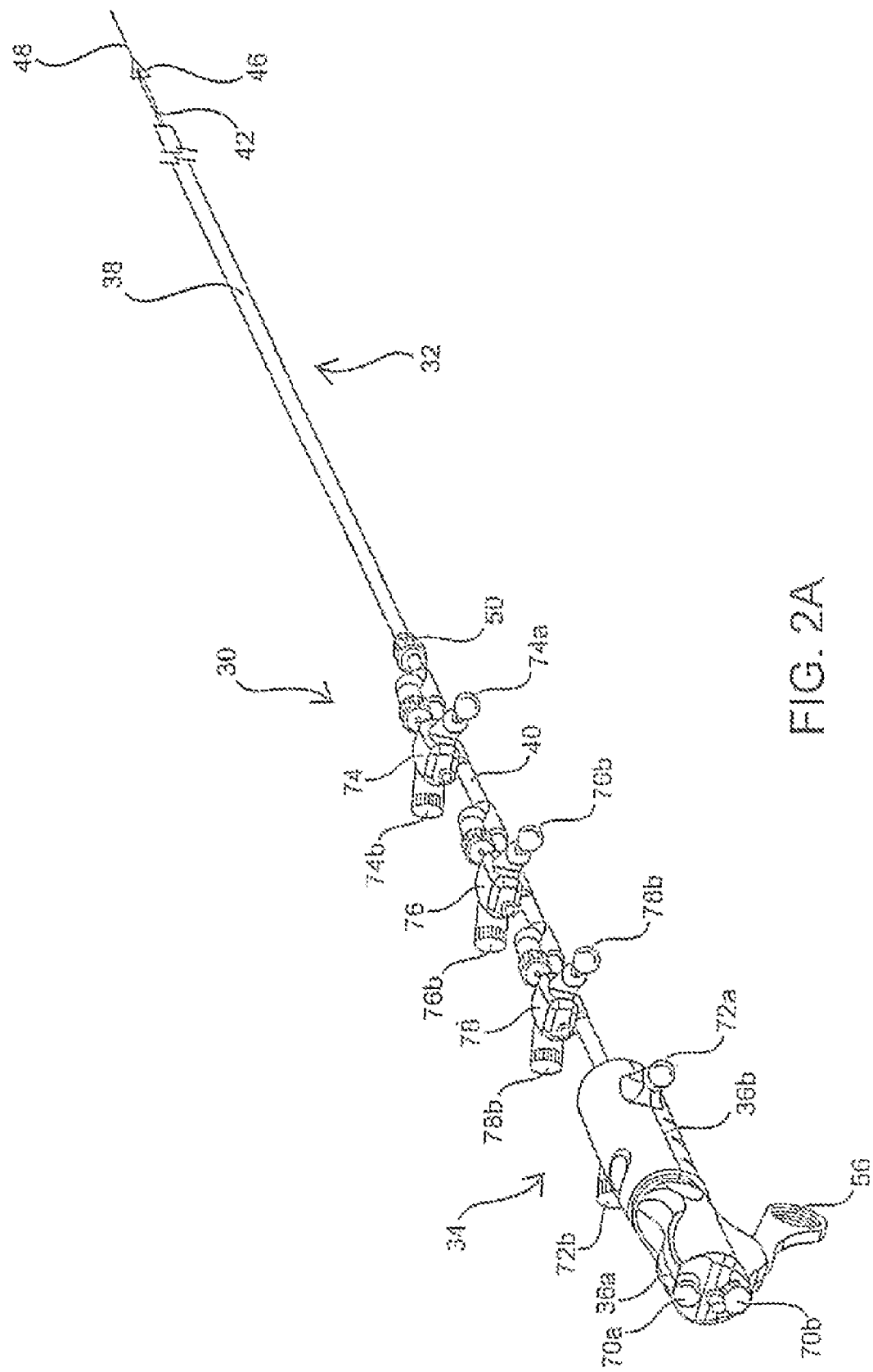
FIG. 2A is a perspective view of a system of the present invention for delivering and deploying the implants of the present invention within a tubular tissue structure within the body.
Figure 2B:
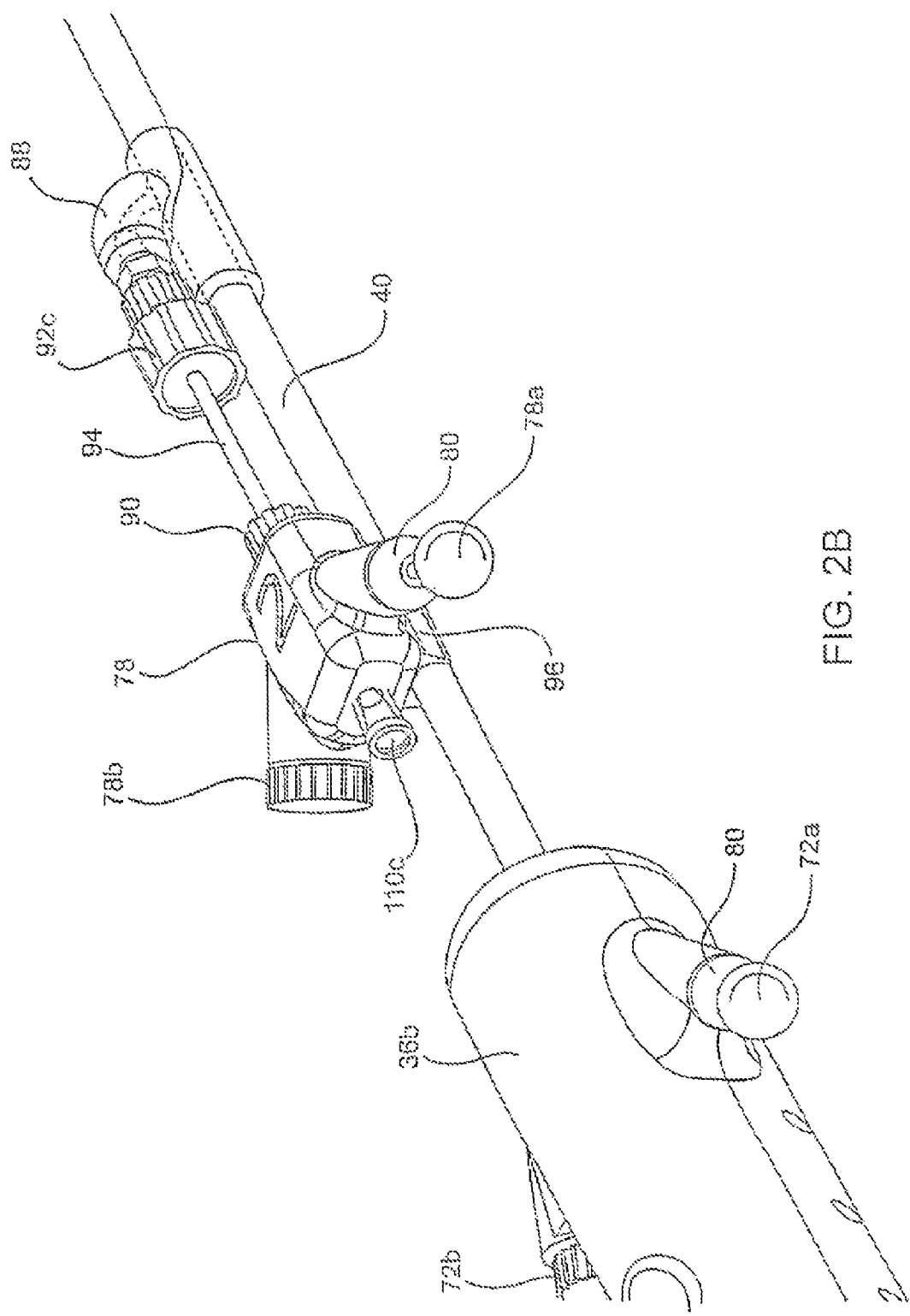
FIG. 2B is an enlarged perspective view of the portion of the system of FIG. 2A including a side branch control and catheter hubs.

Referring now to FIGS. 2A and 2B, there is shown a system 30 of the present invention for implanting the devices of the present invention. System 30 includes a distal catheter portion 32 and a proximal or handle portion 34. Catheter portion 32 is configured for positioning within the vasculature or other pathway leading to the implant site, and includes various elongated members having a plurality of lumens, many of them multi-functional, for guide wire, pull-wire, and fluid passage from one end of the device to the other. Catheter portion 32 includes a translatable outer sheath 38 having a lumen within which an intermediate member 40 is received. The proximal end of outer sheath 38 is configured with a fitting 50 for coupling to a distal hub 52 of intermediate portion 40. Fitting 50 is configured with an internal valve mechanism which fluidly seals the luminal space between the walls of outer member 38 and intermediate member 40, thereby preventing leakage of blood therefrom. Fitting 50 may further include a flush port (not shown) for evacuation of any residual air as is common in catheter preparation. An inner member 42 is received and translatable within a lumen 138 (see FIG. 6A) of intermediate member 40 and defines a main body guide wire lumen 44 for translation of a guide wire 48 therethrough. Inner member 42 terminates at a conical distal tip 46 which facilitates forward translation of the device through tortuous vasculature. The outer member, intermediate member and inner member tubings (as well as any catheter components discussed below) may be made from materials used to construct conventional intravascular sheaths and catheters, including but not limited to biocompatible plastics reinforced with braided materials or any other biocompatible materials which are substantially flexible.

The proximal portion 34 of delivery and deployment system 30 includes proximal and distal handle portions 36a, 36b which translate axially with respect to each other. Inner member 42 is fixed to proximal portion 36a of the handle and intermediate member 40 is fixed to distal portion 36b of the handle such that axial separation and extension of the two handle portions relative to each other controls the amount of extension and foreshortening undergone by a stent operatively loaded within the delivery system, as will be explained in greater detail below.

As mentioned above, in one variation of the present invention, delivery and deployment of an implant is accomplished by the use of a plurality of designated attachment lines, strings, wires or filaments. More particularly, a single string or a set or plurality of strings is provided for controlling and releasably attaching each free end of the implant to the delivery system. Two separate strings or sets of strings are employed to control the main tubular portion of an implantable device—one string or set of strings for controlling the distal end and the other for controlling the proximal end of the device. For each lateral branch of the implant, an additional string or set of strings is provided. The number of strings in each set correlates to the number of crowns or connecting points provided at the respective ends (i.e., at the proximal and distal ends of the main stent portion and at the distal ends of the branch portions) of the device. Each string is interlooped with a designated crown with both of its ends positioned and controlled at the handle of the device, where one end of each attachment string is permanently affixed to the delivery and deployment system 30 and the other end is releasably attachable to the delivery and deployment system 30. When operatively loaded within system 30, the luminal ends of the implant are releasably attached to various portions of system 30. For example, the distal end of the main lumen of the stent is releasably attached to inner member 42, the proximal end of the main lumen of the stent is releasably attached to intermediate member 40, and the distal end of each side branch stent is releasably attached to a designated side branch catheter 150 (see FIG. 6A).

Each attachment string or set of attachment strings is controlled, i.e., able to be fixed, released, tensioned, pulled, tightened, etc., by a designated control mechanism. Accordingly, the number of control mechanisms provided on the illustrated embodiment of the subject system corresponds to the number of attachment string sets; however, control of the string sets may be consolidated into a fewer number of control mechanisms. The various control mechanisms may have any suitable configuration and be mounted at any suitable location on system 30 where one exemplary configuration and location of the control mechanisms is illustrated in FIG. 2A. In particular, each control mechanism includes a pair of controls in the form of knobs, dials, switches or buttons, for example, where one control is for linearly translating, i.e., pulling, the strings by their fixed ends through the deployment system 30 when deploying the implant, and the other control is for selectively releasing and fixing the free ends of the strings prior to deployment of the implant.

Controls 70a, 70b and 72a, 72b, for controlling the distal and proximal luminal ends, respectively, of the implant, are provided on handle portions 36a and 36b, respectively. An additional pair of controls for each set of attachment strings associated with each of the implant's side or lateral branch lumens is provided on a hub releasably mounted to intermediate member 40 where the collective hubs are serially arranged between the proximal end 50 of outer sheath 38 and the distal end of distal handle portion 36b. For example, for use with implant 2 of FIG1 having three branch lumens 6a, 6b and 6c, three hubs 74, 76 and 78 and associated pairs of controls, respectively, are provided where the most distal pair of controls 74a, 74b controls the attachment strings for the most distal of the stent branch lumens 6a, the second or middle pair of controls 76a, 76b controls the attachment strings for the middle stent branch lumen 6b, and the most proximal pair of controls 78a, 78b controls the attachment strings for the most proximal of the stent branch lumens 6c.

Each pair of controls includes a fixed-end member 70a, 72a, 74a, 76a and 78a, here in the form of a knob, to which one set, the fixed set, of ends of the attachment strings is permanently anchored but which itself is removable from the respective handle portion or hub in order to manually pull the strings therethrough. This control maintains a constant tension on the attachment strings and keeping the implant restrained within the delivery system while the delivery system is being articulated through the vasculature. As best illustrated in FIG. 2B, each knob is positioned within a hemostatic valve 80 for preventing the back flow of fluid, e.g., blood, out of the handle or hub before and after the knob is removed therefrom. Each pair of controls also includes a releasable end member or clamp 70b, 72b, 74b, 76b and 78b, here in the form of a dial or drive screw, by which the free ends of the string set are releasably anchored to the respective handle portion or hub. When ready to deploy a respective luminal end of the implant, the drive screw is selectively loosened to allow for release of the tension on the respective string set. Those skilled in the art will appreciate that the relative positioning and arrangement of the various control mechanisms may vary with the intent of providing an organized, ergonomically designed profile.

Figure 3A:
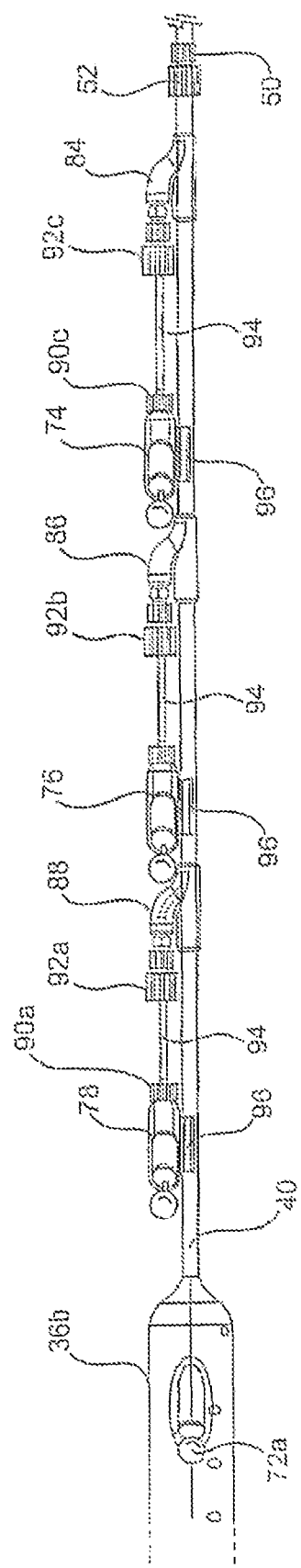
FIGS. 3A and 3B are side views of the side branch control and catheter hubs of the system of FIGS. 2A and 2B in open and closed configurations, respectively.
Figure 3B:
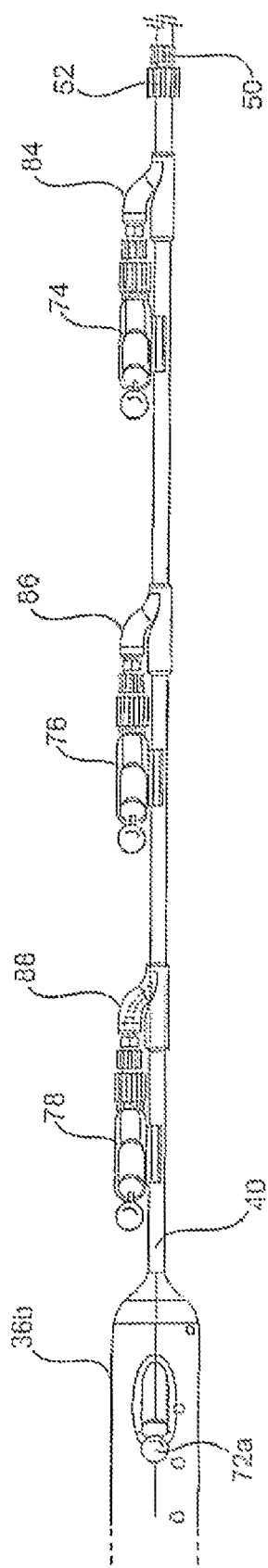

Referring now to FIGS. 2B, 3A and 3B, each side branch control hub 74, 76 and 78 is associated with a distally positioned side branch catheter hub 84, 86 and 88, respectively (only the most proximally positioned hubs 78 and 88 are illustrated in FIG. 2B). Extending between each pair of hubs is a proximal portion 94a, 94b, 94c of side branch catheters 150a, 150b, 150c, respectively (see FIG. 6A), which extends from a sealable port 110a, 110b, 110c (see FIG. 2B) at the back end of each control hub 74, 76 and 78 to a distal end and through respective side branch catheter lumens 148 within intermediate member 40 (see FIG. 6A). Within each side branch catheter 150a, 150b, 150c is a side branch guide wire lumen 152a, 152b, 152c (see FIG. 6A). Port 110a, 110b, 110c allows for the entry and passage of a side branch guide wire 154a, 154b, 154c (see FIG. 6A) through a respective side branch guide wire lumen 152. One or both of the side branch catheter and side branch guidewire may be deflectable. Each of the control hubs 74, 76 and 78 are slidably engaged with intermediate member 40. The undersides of the control hubs have cuff 96, a partial ring configuration or the like, such that hubs are fully releasable from intermediate member 40 as well as slidable thereon. As mentioned above, each of the side branch stent lumens is releasably coupled to the distal end of side branch catheter 150a, 150b, 150c by way of a designated attachment string or set of attachment strings. Regardless of the relative position between the side branch control hubs 74, 76, 78 and the associated side branch catheter hubs 84, 86, 88, the attachment string sets are held in complete tension in both configurations illustrated in FIGS. 3A and 3B until they are released by their respective control knobs 74b, 76b, and 78b. When the control hubs are in a distal or close position relative to the catheter hubs, as illustrated in FIGS. 2A and 3B, where the proximal portion 94a, 94b, 94c of side branch catheter 150a, 150b, 150c is fully received within the associated catheter hub, the side branch stents are held in a partially deployed state. In the partially deployed state, the side branch stents are held stretched, with tension being applied by the distal end of the respective extended side branch catheter 94a, 94b, 94c removably attached to the distal end of the stretched side branch stent apices or connection points by the side branch catheters' respective string or string set. The tension being applied to the distal end of each side branch stent is transferred through the side branch stent thereby elongating its length while simultaneously reducing the diameter. This allows for the positioning of a larger stent diameter within a smaller diameter side branch vessel. This partially deployed state, i.e., where the side branch stent diameter is smaller than the side branch vessel into which it is being placed, also allows for the flow of blood around the implant as well as through it thereby allowing perfusion of downstream vessels and organs during placement. It is preferential to have blood continue to flow through intersecting side branch vessels during the procedure in order to avoid ischemia to the effected downstream organs. The side branch stent is stretched by the extension of the side branch catheter which is releasably attached to the crowns of the distal end of the side branch stent. The stretching of the side branch stent enables its subsequent placement within an undersized, targeted side branch vessel. Typically, the diameter of a side branch stent in its natural, unconstrained state is about 5% to about 50% greater than the diameter of the side branch vessel into which it is to be placed. Conversely, when the control hubs are in a proximal or retracted position, as illustrated in FIGS. 2B and 3A, each side branch stent is held in a deployed or unstretched condition.

The side branch catheters 150a, 150b, 150c sidably extend at their proximal ends 94a, 94b, 94c through respective side branch catheter hubs 84, 86, 88 and a hemostatic valve 92a, 92b, 92c positioned at the back end of the catheter hub. Each side branch control hub 74, 76, 78 has a luer fitting 110a, 110b, 110c (where only 110c is shown) which allows a hemostatic valve (not shown) to be applied. The hemostatic valve may be a Y arm adapter or a Toughy-Borst adapter which allows the sealed introduction of a guidewire. The Y arm luer fitting allows for clearing the guidewire lumen of air by flushing the catheter with saline prior to inserting the catheter into the body. At subsequent stages of the procedure, this lumen may be used to introduce radiographic dye in order to visualize blood flow through the side branch arteries.

Figure 4:
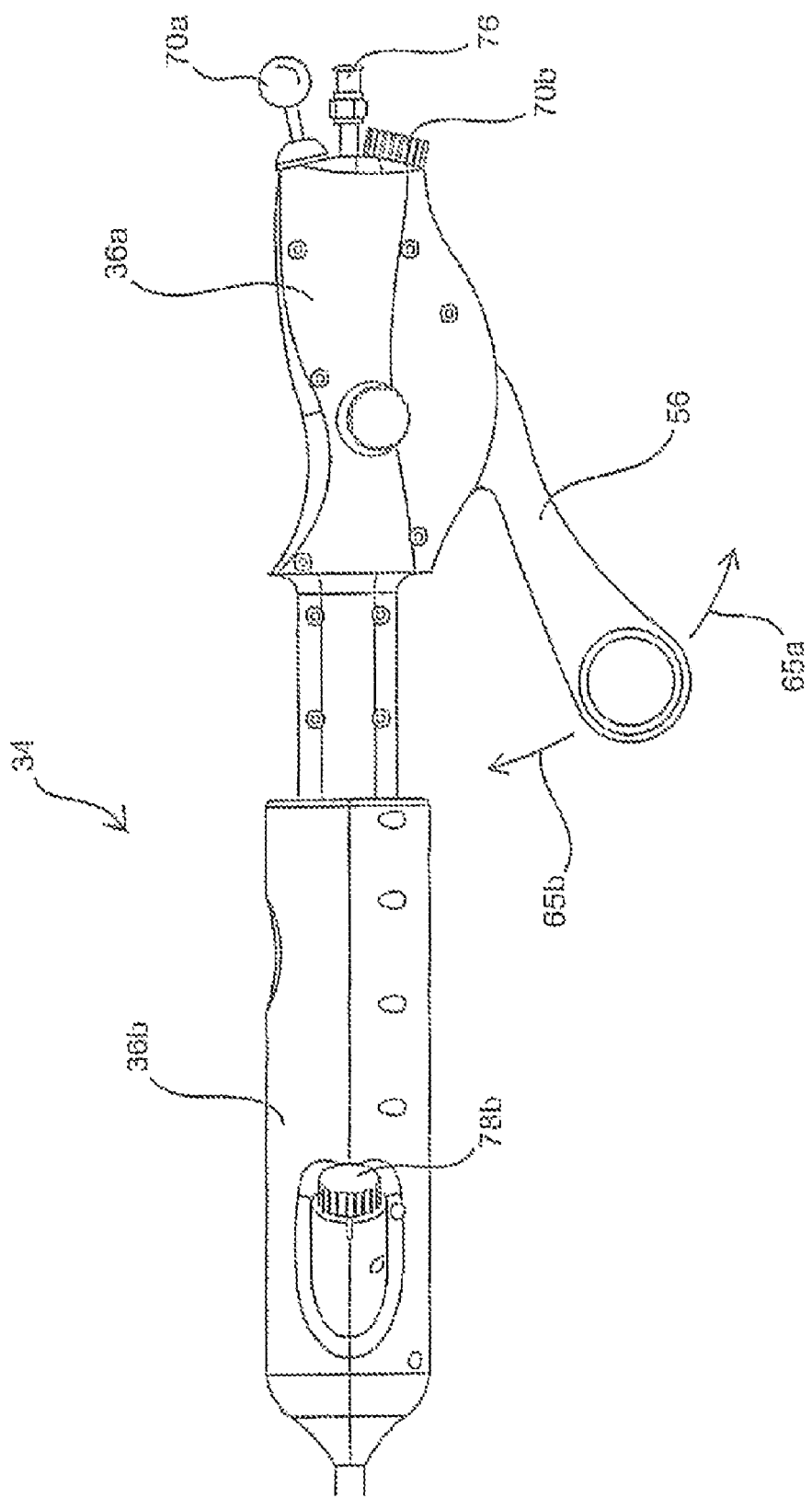
FIG. 4 is a side view of the handle portions of the system of FIG. 2A.

A main body port 76, as illustrated in FIG. 4, located on the back end of proximal handle portion 36a is in fluid communication with a guide wire lumen 44 which extends through a central lumen 138 (see FIGS. 6A and 6B) within intermediate member 40. Guide wire lumen 44 provides for the passage and translation of a primary guide wire 48 which is used to direct and guide distal portion 32 of the system to a target implant site within the vasculature as well as to facilitate the positioning and implantation of the distal end of the primary lumen of the implantable device. The main body port 76 has a leur fitting similar to leur fitting 110 described above with respect to the side branch catheter control hubs.

Figure 9:
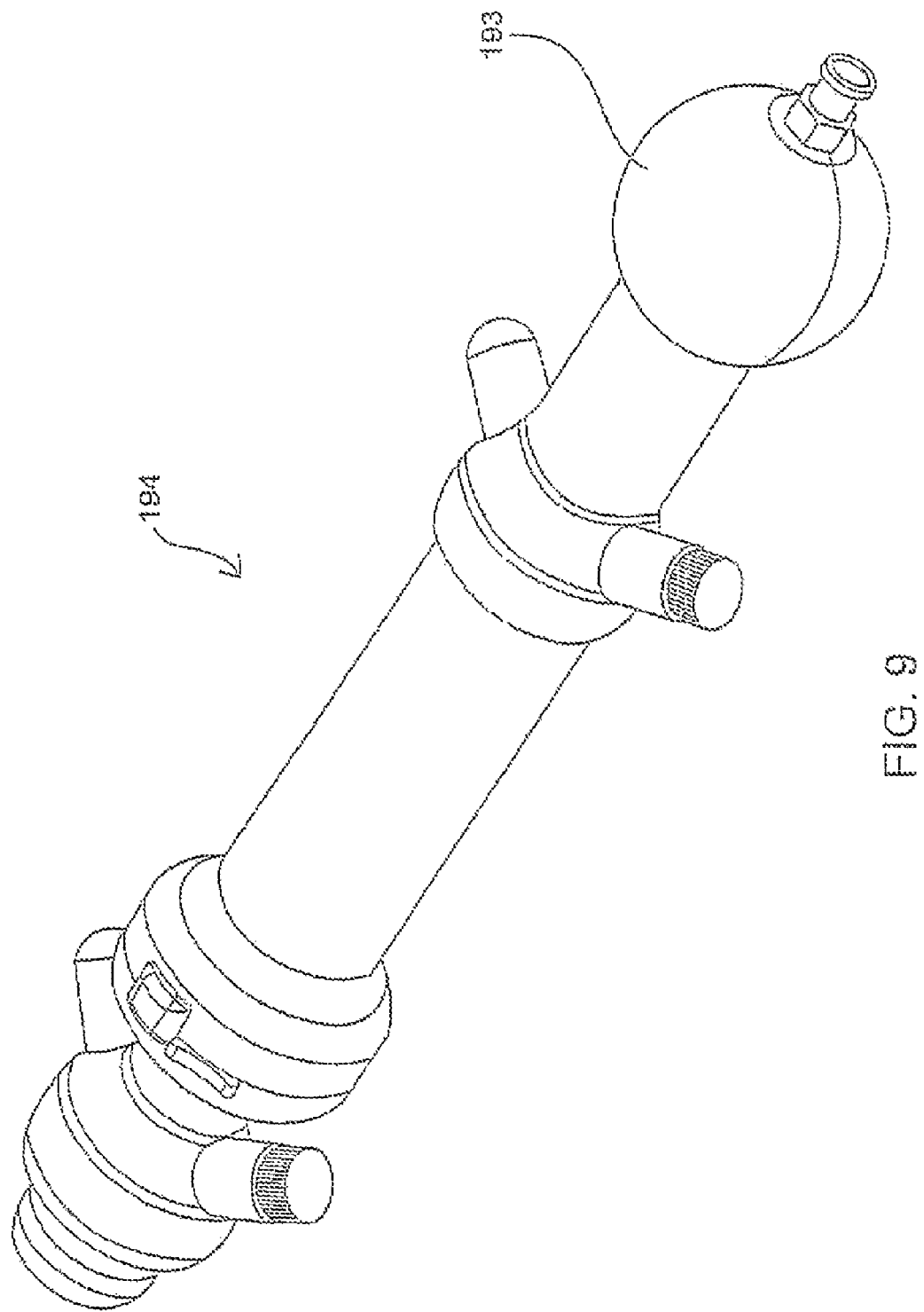
FIG. 9 illustrates another embodiment of handle portion of the delivery and deployment system of the present invention.

As is further illustrated in FIG. 4, a lever mechanism 56 extending distally and downwardly from proximal handle portion 36a is provided for steering distal catheter portion 32 of device 30 through the vasculature into which it is positioned. This lever may be replaced by a rotating control knob 193 in another handle embodiment 194 shown in FIG. 9A. A steering pull-wire, string or filament (not shown) is fixed to the proximal end of lever 56 and extends through catheter portion 32 where its distal end terminates and is attached within nose cone 46 of inner member 42. Lever 56 is pivotally coupled within handle portion 36a such that when rotated in a downward direction (indicated by arrow 65a of FIG. 4), the steering pull-wire is caused to be in a relaxed or slacken state. Conversely, when lever 56 is rotated upward (indicated by arrow 65b), the steering pull-wire is pulled or tensioned thereby causing the distal tip of inner member 42, and thus the distal end of device 30, to bend. Any number of steering pull-wires may be employed and selectively tensioned to selectively articulate the distal end of device 30 in multiple directions orthogonal to the longitudinal axis of the implantation system. Typically, the subject delivery and deployment system will have at least one, and often two to four distal points of articulation. These articulation points may be at one or more distances from the distal end of the catheter 32 in order to create compound curves of the distal end of the catheter.

Figure 5A:
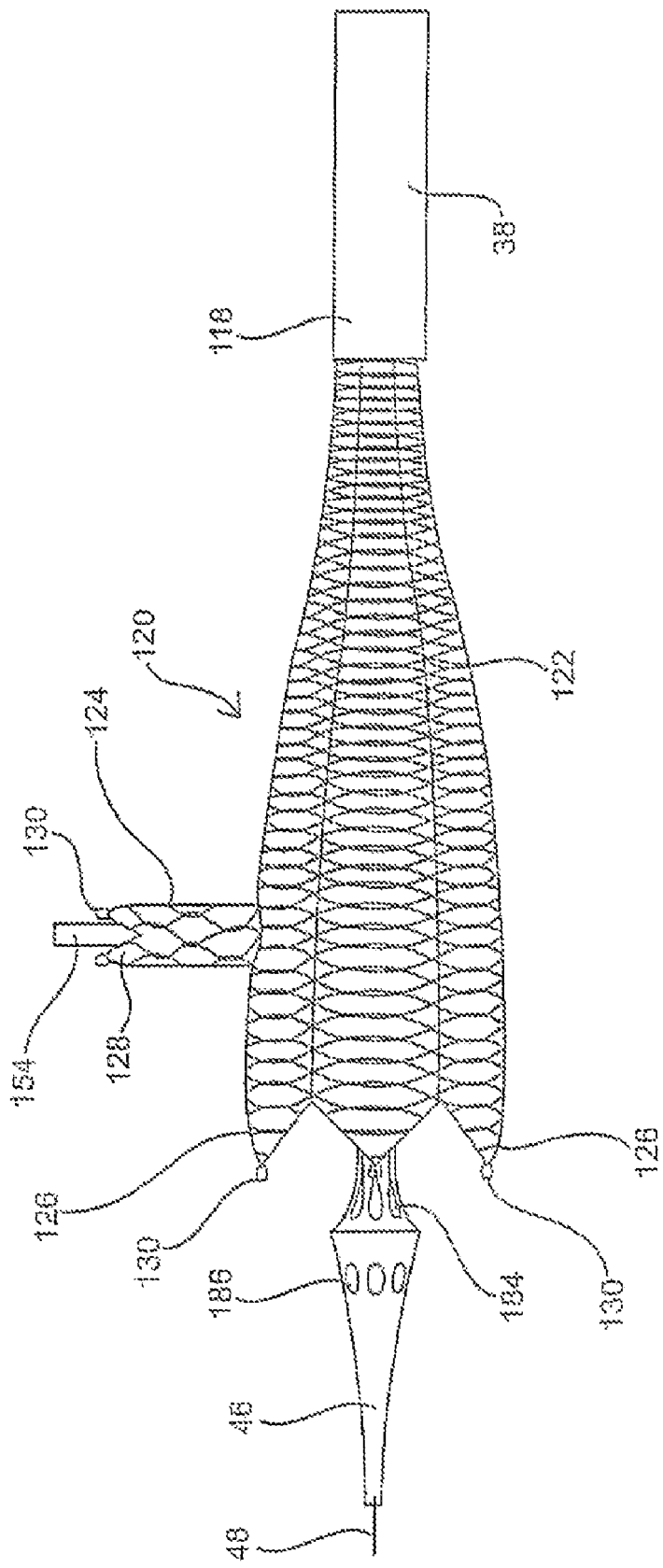
FIG. 5A is a side view of the distal end of the delivery and deployment system of the present invention with an implantable device of the present invention shown partially deployed from the implantation system.
Figure 5B:
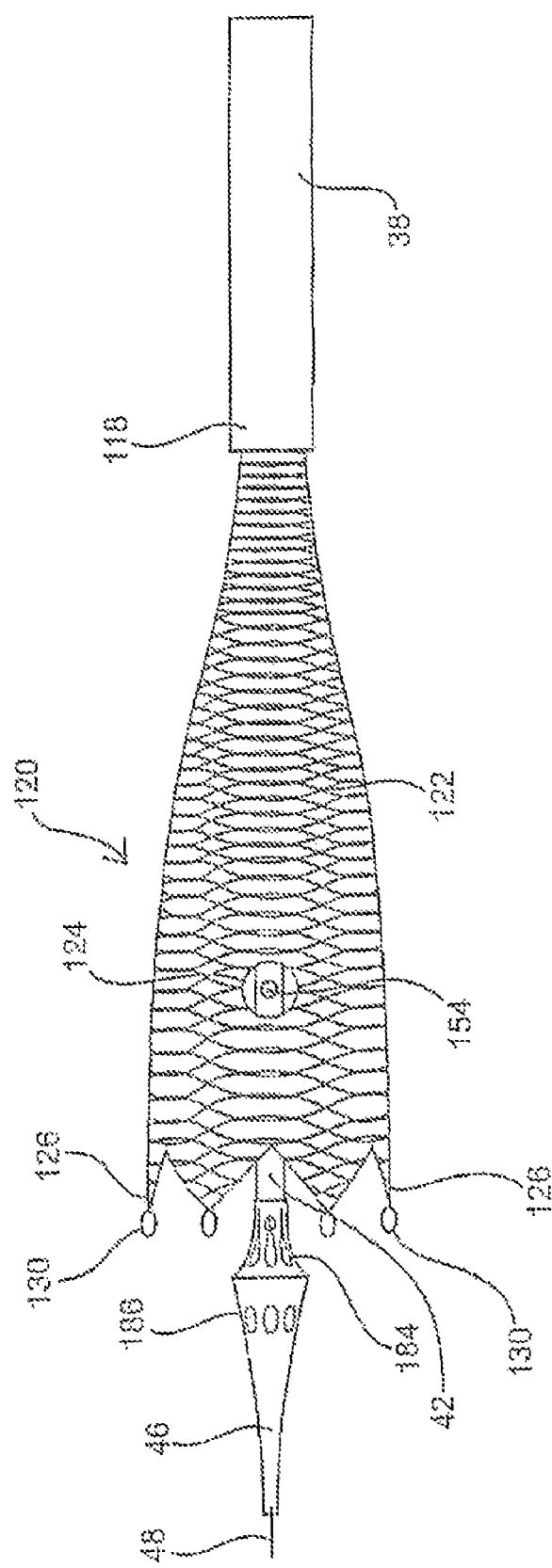
FIG. 5B shows a top view of the system and implantable device of FIG. 5A.
Figure 5C:
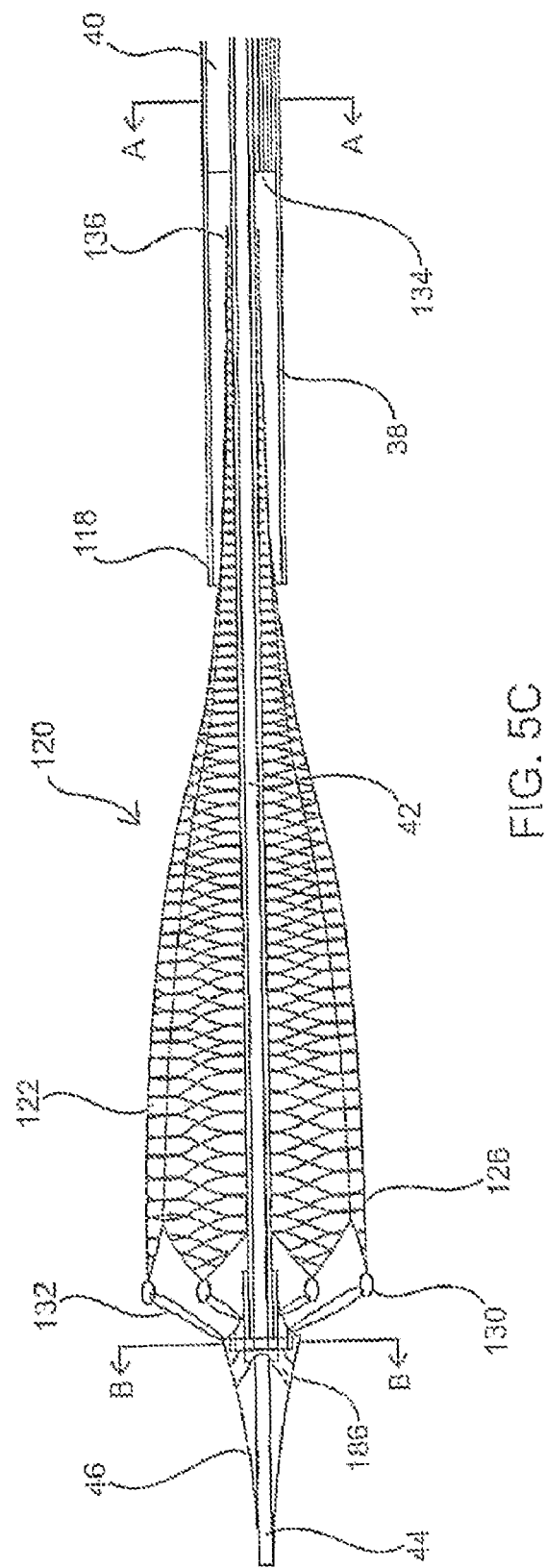
FIG. 5C shows a longitudinal cross-sectional view of FIG. 5B.

The relative positioning and interfacing of the implantable device with the various catheters, lumens, guidewires, ports and pull-wires of the subject implantation system will now be described with respect to FIGS. 5A-6C, 6A and 6B. FIGS. 5A-5C illustrate an implantable device 120 partially deployed from the distal end 118 of outer sheath 38. Implantable device 120 includes a main tubular body 122 and may include one or more lateral tubular branches 124. At the distal tips of crowns or apexes 126 of main body 122 and crowns or apexes 128 of side branch 124 may be eyelet loops 130 for receiving attachment strings 132 (shown only in FIG. 5C). As is illustrated in FIG. 5C, when operatively loaded within system 30 of FIG. 2A, the main lumen 122 of device 120 is longitudinally disposed between outer sheath 38 and inner member 42 and is positioned distally of the distal end 134 of intermediate member 40.

To load the implant device into outer sheath 38, the handle controls are set to stretch the stent by extension of the distal tip 46 of the inner member 42 relative to the distal end of the intermediate member. When proximal and distal handle portions 36a and 36b are extended from each other, shown in FIG. 8D, the main lumen of the stent is in a stretched or tensioned condition. Conversely, when proximal and distal handle portions 36a and 36b are unextended, as shown in FIG. 8E, the main lumen of the stent is in an unstretched or untensioned condition. The distal lumenal ends of inner member 42 and intermediate member 40 are connection points for the string or strings which are releasably attached to the distal and proximal stent main lumen openings 122. As discussed above, the side branch stent distal lumenal end is releasably attached to the distal end of the side branch catheter.

Figure 6A:
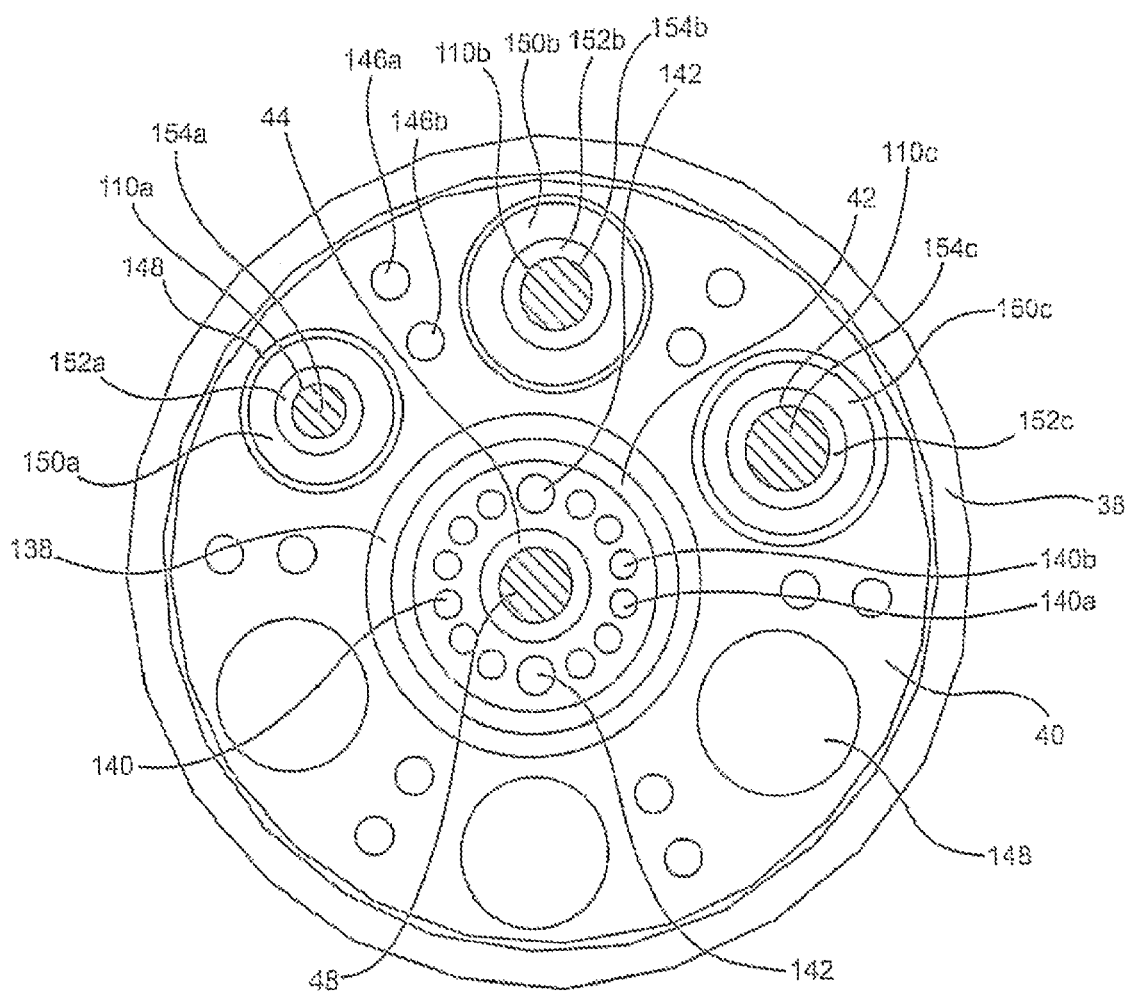
FIG. 6A is a cross-sectional view taken along line A-A of FIG. 5C.

FIG. 6A shows a cross-section of a distal portion of implantation system along the lines A-A of FIG. 5C, specifically, the cross-sectional view is taken. at the distal end of intermediate member 40. This view shows the nested relationship between outer member 38, intermediate member 40, inner member 42 which is positioned within central lumen 138 of intermediate member 40, and main guide wire 48 positioned within a central guide wire lumen 44 of inner member 40 which extends distally through tip 46.

Inner member 42 is a very small diameter catheter, for example, in the range of 3 to 8 French for cardiovascular applications, and has, in addition to central guide wire lumen 44, a plurality of attachment string lumens 140 circumferentially disposed about central guide wire lumen 44 which serve to direct the alignment of the attachment strings to the connection points on the distal end of the main stent lumen. Multiple lumens 140 are located at the distal portion of member 42 and extend along the entire length of the inner member 42. Lumens 140 may be in communication with one or more flush ports at the handle portion of the delivery system whereby saline may be flushed through lumens 140 at a pressure greater than that of the surrounding blood flow to prevent blood flow through the device lumens. Lumens 140 may also be used to deliver radiopaque contrast dye used during fluoroscopically visualized placement of the device. Lumens 140 and the exit ports 186, described below, allow for visualization of the dye flowing through the implant at various stages of deployment in order to verify that placement of the stent yields a satisfactory flow pattern and therapeutic result.

In other embodiments, such as that illustrated in FIGS. 10A, 10B and 10C, attachment string lumens 140 may extend along only a portion of the length of inner member 40, e.g., only a few millimeters distally to proximally. This embodiment is particularly suitable in the case where only one attachment string is employed with multiple stent connection points. Here, the single string element exits one of the distal lumens, is passed through the stent connection point, is passed distally to proximally through another of the lumens, exits proximally from that lumen and is passed through another of the lumens distally to proximally and passed through another stent connection point. The interlacing pattern continues until all stent connection points are laced with the singular string which passes through the multiple circumferential lumens. This configuration of attachment string lumens which extend only a portion of the length of the inner member, may also be employed with the intermediate member 40 and with the side branch catheters 94a, 94b, 94c. With respect to an intermediate member employing such a string lumen configuration, the proximal portion of intermediate member 40 would be a single lumen containing the inner member 42 and the shorter circumferential lumens would contain the side branch catheters as well as the attachment wires for the proximal end of the main stent lumen. As will be seen from this embodiment and those discussed below, any combination of lacing patterns may be used to attach an individual stent end to the respective catheter to which it is attached.

Referring again to the embodiment FIG. 6A, the number of distal attachment strings lumens 140 is double the number of attachment strings 132 where one pair of adjacent attachment strings lumens 140a, 140b is provided for each distal attachment string 132. As such, where device 120 is fully loaded within the deployment system, the first portion of a distal attachment string 132 resides within lumen 140a and a second or return portion of the distal attachment string resides within lumen 140b.

In addition to attachment/deployment string lumens 140 are one or more steering pull-wire lumens 142, the function of which is as described above with respect to FIG. 4. Typically, one or two pairs of diametrically opposed (180° apart) steering pull-wires are employed to provide opposing orthogonal deflections of the distal end of the delivery system. The greater the number of steering pull-wire pairs employed, the greater the directions of steering in articulating the delivery system.

In addition to central lumen 138 through which inner member 42 is translated, intermediate member 40 includes a plurality of proximal attachment string lumen pairs 146a, 146b where lumen 146a is shown situated radially outward from lumen 146b. The attachment strings attached to or threaded through the proximal crowns (not shown) of main lumen 122 of device 120 utilize lumens 146. The number of proximal attachment string lumens 146 is double the number of proximal attachment strings where one pair of attachment string lumens 146a, 146b is provided for each proximal attachment string, i.e., where device 120 is fully loaded within the delivery and deployment system, the fixed-end portion of a proximal attachment string resides within lumen 146a and the distal or return portion of the proximal attachment string resides within lumen 146b.

In addition to attachment string lumens 146, intermediate member 40 also provides a plurality of lumens 148, also circumferentially disposed about central lumen 138 and preferably interposed between pairs of proximal attachment lumens 146, where one or more of the lumens 148 may be employed to translate and deliver a side branch catheter 150 (shown in FIG. 6A without detail). Side branch catheter 150 provides a central side branch guide wire lumen 152 for delivering and translating a side branch guide wire 154. Additional lumens 148 extending from a handle flush port (not shown) may be provided for evacuating air from the delivery system 30. The additional lumens 148 may also allow for the rehydration of tissue graft coverings or other coverings which need to be prepared with solutions and potential therapeutic agents such as pharmacologics, stem cells, or other agents. This allows the stent graft or other device to be constrained in the delivery catheter in a dried dehydrated state subsequently packaged, sterilized, and rehydrated by the flushing and preparing the catheter at the time of use. Any unused lumens 148 provide enhanced flexibility of the intermediate member, particularly where the distal end of the device is deflectable at multiple articulation points.

Figure 7B:
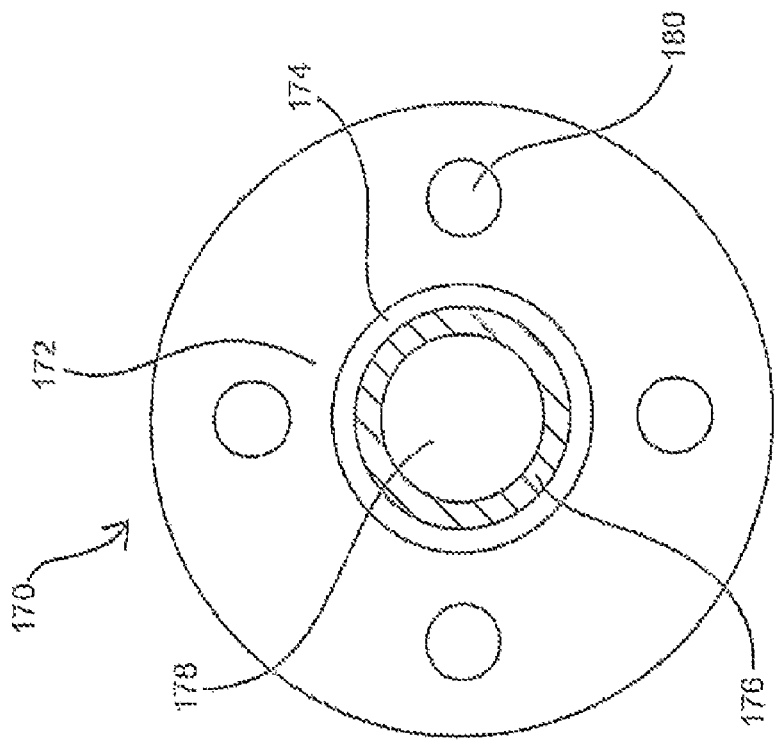
FIGS. 7A, 7B and 7C are cross-sectional views of possible embodiments of side branch catheters of the present invention.
Figure 7A:
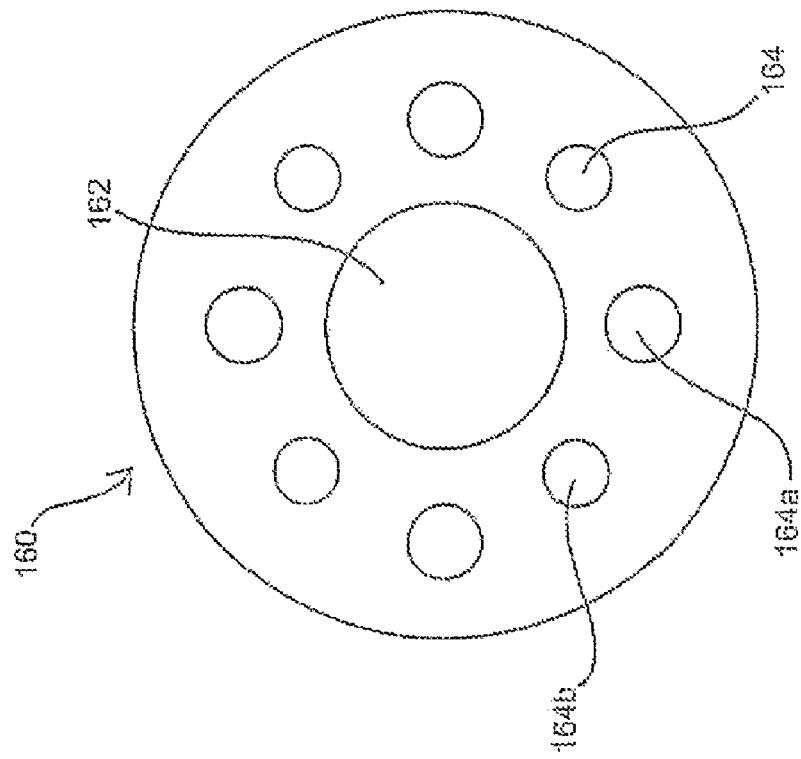
Figure 7C:
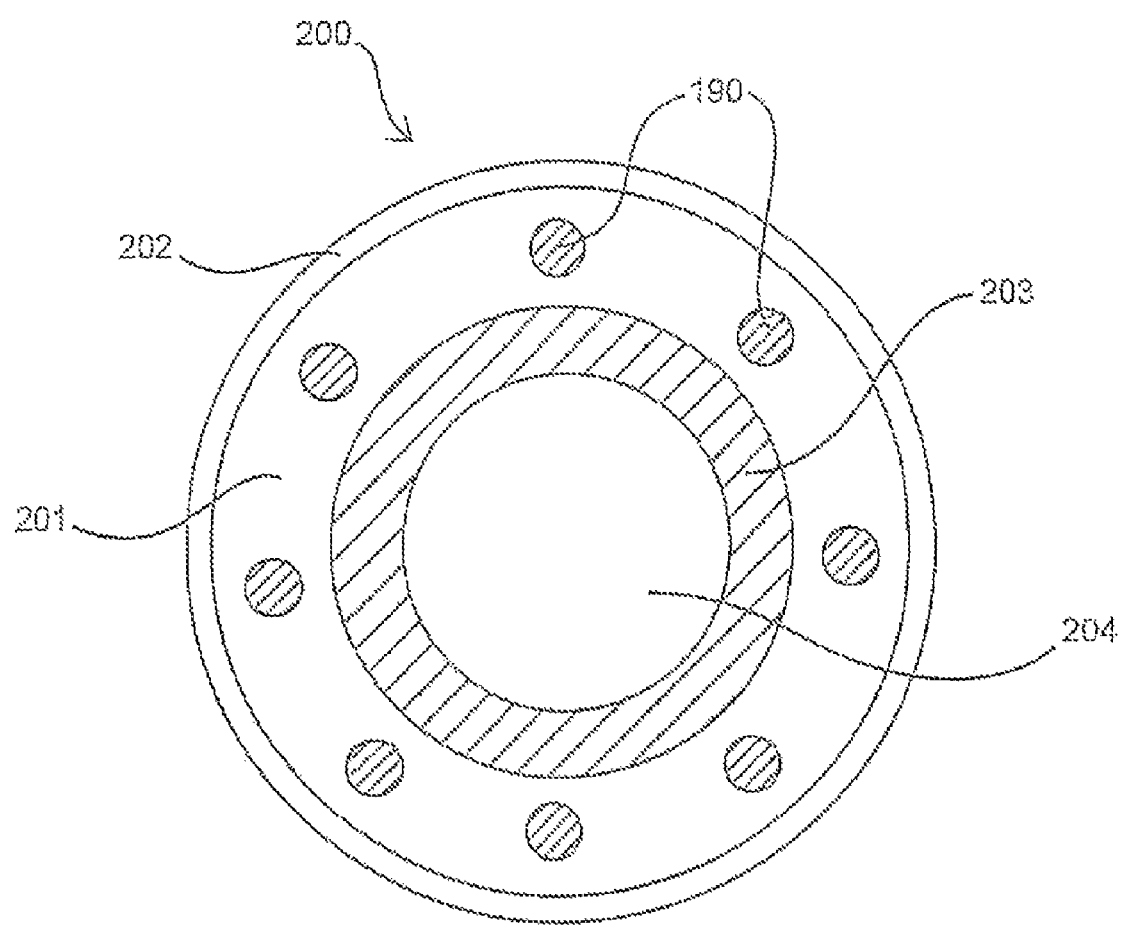

FIGS. 7A, 7B and 7C illustrate various possible embodiments of side branch catheters suitable for use with the delivery system of the present invention. Side branch catheter 160 of FIG. 7A provides a central guide wire lumen 162 and plurality of attachment string lumens 164 arranged circumferentially about central lumen 162. Lumens 164 are utilized or occupied by the attachment strings (not shown) which are looped or threaded through the distal crowns 128 of side branch lumen 124 of device 120 (see FIG. 5A). The number of side branch attachment string lumens 164 is double the number of side branch attachment strings where one pair of attachment string lumens 146a, 146b is provided for each side branch attachment string, i.e., where device 120 is fully loaded within the implantation system, the proximal portion of a side branch attachment string resides within lumen 164a and the distal or return portion of the side branch attachment string resides within lumen 164b.

Side branch catheter 170 of FIG. 7B provides an outer member 172 having a central lumen 174 and an inner member 176 positioned concentrically therein. Inner member 176 also has a central lumen 178 for translating and delivering a side branch guide wire (not shown). Outer member 172 further provides a plurality of side branch attachment string lumens 180 where there is a one-to-one correspondence between the number of side branch attachment string lumens 180 and the number of side branch attachment strings (not shown). In this embodiment, the proximal portion of side branch attachment strings reside within the space between the internal diameter of outer member 172 and the external diameter of inner member 176 and after being looped through the distal attachment eyelets, crowns or cells, the distal or return portion of the strings pass through lumens 180 of outer member 172.

In another embodiment of side branch catheter 200, shown in FIG. 7C the side branch catheter can be composed of two concentric single lumens. One single lumen tubing 202 defining an internal diameter and another single lumen tubing 203 defining an outer diameter provides for the side branch attachment strings to be contained within the space 201 between the internal diameter of the outer tubing 202 and the outer diameter of the inner tubing 203. The internal diameter of the inner tubing is used to translate a guidewire (not shown) through side branch guidewire lumen 204 which is isolated from the attachment strings as shown in FIG. 7C. This lumen configuration may also be employed with the intermediate and inner members.

Figure 6B:
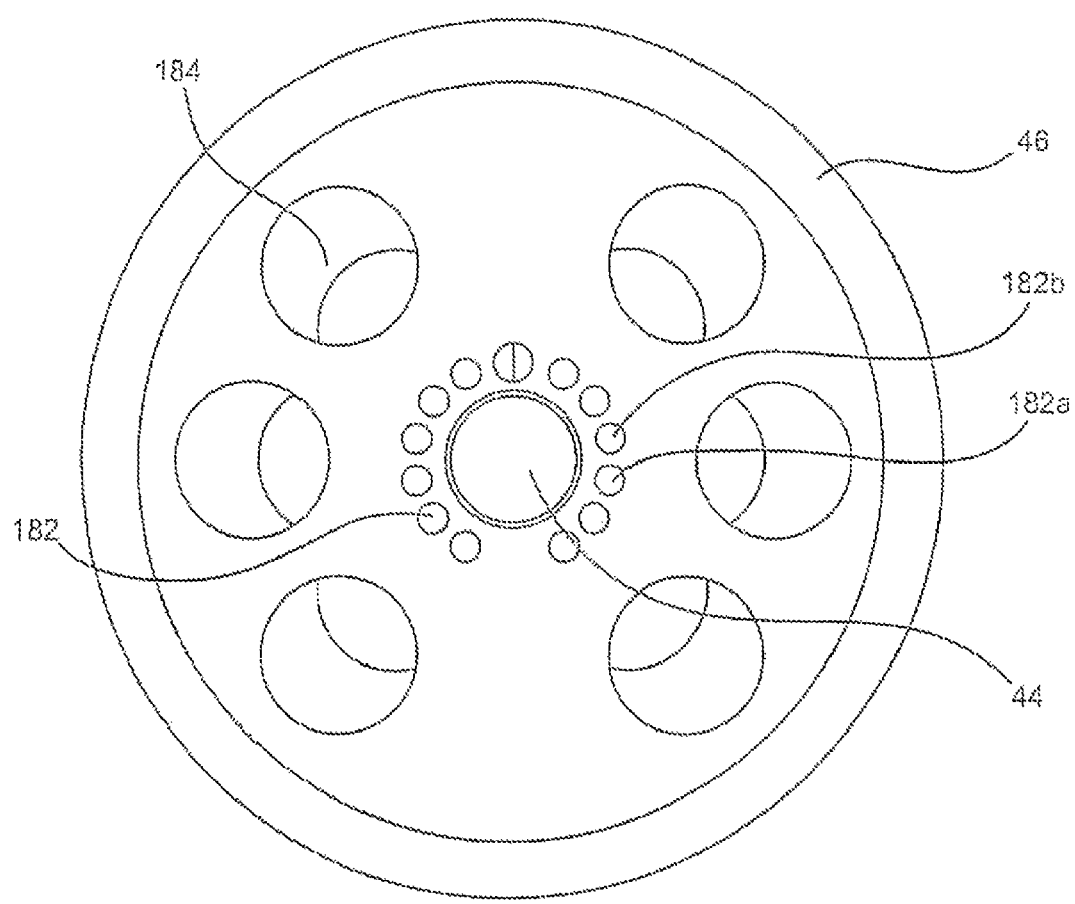
FIG. 6B is a cross-sectional view taken along line B-B of FIG. 5C.
Figure 6C:
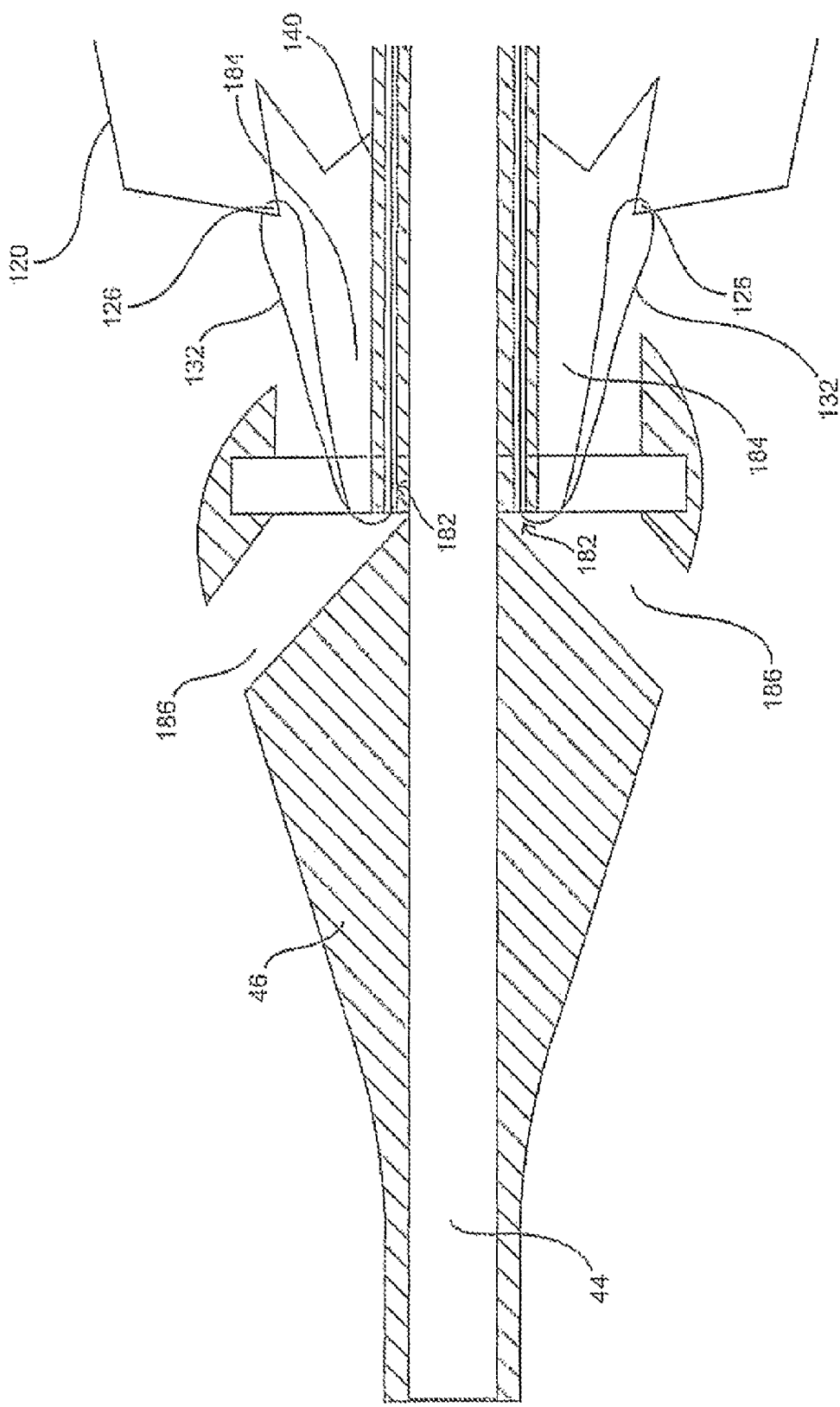
FIG. 6C is longitudinal cross-sectional view of the catheter tip portion of the delivery and deployment system of FIG. 5C.

Referring to FIG. 6B, there is shown a cross-sectional view taken along lines B-B of FIG. 5C, specifically through a proximal end of distal tip 46 where inner member 42 terminates. Distal tip 46 provides the distal portion of guide wire lumen 44 as well as the distal lumen portions 182 of distal attachment string lumens 140 of inner member 42 where the plurality of distal lumen portions 182 are axially aligned and have a one-to-one correspondence with inner member attachment string lumens 140. As such, the same pairing of adjacent attachment string lumens 182a, 182b is provided for each distal attachment string 132, i.e., where the fixed-end portion of a distal attachment string 132 resides within lumen portion 182a and the releasable or return portion of the distal attachment string resides within lumen portion 182b. As is best illustrated in FIG. 6C, after passing within lumen portions 182a, the attachment strings 132 are passed radially out of distal tip 46 through designated proximal side ports 184. The attachment strings are then looped or threaded around eyelets 130 or crowns or apices 126 or through the very distal cells of main lumen 122, and threaded back through the designated side port 184 of distal tip 46 whereby they re-enter respective lumen portions 182 and respective attachment string lumens 140. As such, for every pair of attachment string lumens, there are half as many side ports 184, i.e., there is a one-to-one correspondence between the number of attachment strings 132 and the number of distal tip side ports 184. Distal tip 46 also provides for distal side ports 186 to facilitate the loading of strings during assembly of the implant to the deliver system.

Figure 16:
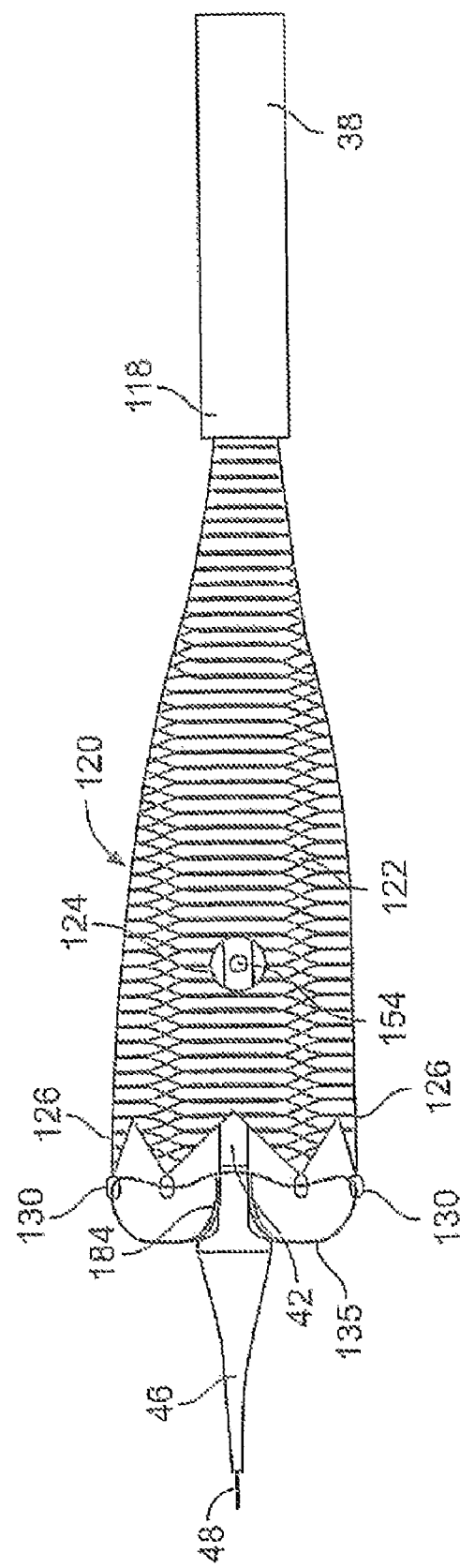
FIG. 16 illustrates a longitudinal cross-sectional view of the distal end of another delivery and deployment system of the present invention with an implantable device of the present invention shown partially deployed from the implantation system.

FIG. 16 illustrates a deployment system of the present invention in which only a single string 135 is used to retain and deploy the distal end (forward facing end) of implantable device 120. The basic components of the system are comparable to those identified and described with respect to FIGS. 5A-5C where like reference numbers refer to similar components. Similar to the manner described with respect to FIGS. 10A-10C above, the singular attachment/deployment string 135 is passed through a designated lumen (not shown) within guide wire catheter 42 and passed radially out of distal tip 46 through a designated proximal side port 184. The attachment/deployment string 135 is then looped or threaded through each of eyelets 130 (or through crowns or apices 126 or through the very distal cells of main lumen 122), and threaded back through another designated side port 184 of distal tip 46 whereby it re-enters the string lumen. The string extends through the system to the proximal end and is able to be fixed, released, tensioned, pulled, tightened, etc. by a control mechanism as described above. In similar fashion, additional strings may be used for attachment and deployment of the other lumenal ends of the implantable device, where each lumenal end is controlled by a separate string. With fewer strings, the complexity of fabricating and operating the stent delivery system is greatly reduced. Additionally, the necessary cross-sectional profile (i.e., diameter) of the system can be minimized and, thus, applicable in smaller vessel applications.

Figure 17:
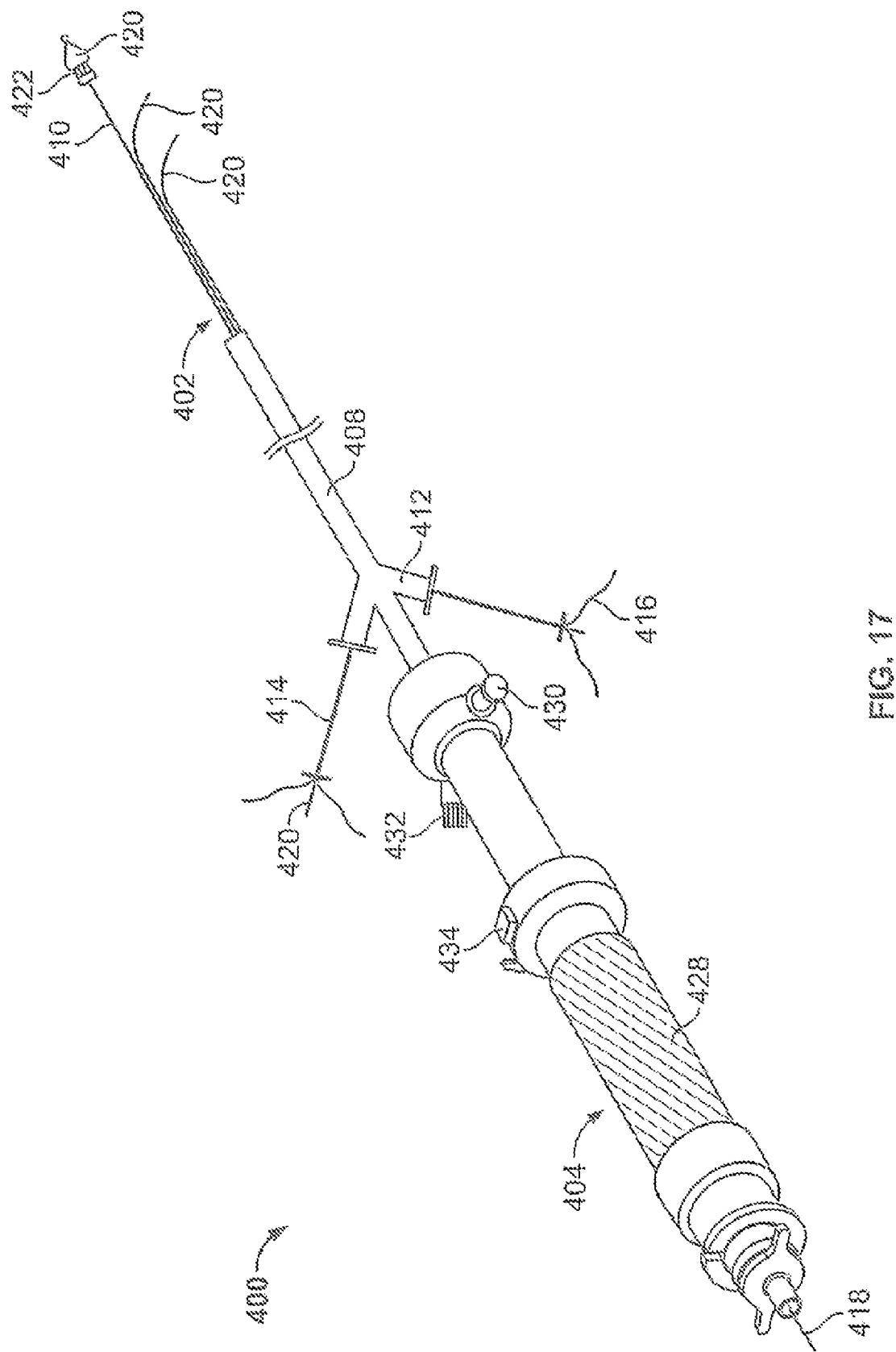
FIG. 17 illustrates a perspective view of another delivering and deploying system of the present invention.

As mentioned above, the deployment/attachment means of the subject systems are not limited to strings and other tensionable elements, and may include other means. An example of alternative stent deployment/attachment means is provided with the delivery system 400 of FIG. 17. System 400 includes a distal catheter portion 402 and a proximal or handle portion 404.

Catheter portion 402 includes outer sheath 408 having one or more lumens therein and within which an intermediate member 410 is translatable there through. When operatively loaded within delivery system 400, the main body of a stent 450 (shown in FIG. 18A) is received between the luminal spacing between outer sheath 408 and intermediate member 410. Intermediate member 410 defines a lumen through which an inner member 416 (see FIG. 18A) is translated and which, in turn, defines a lumen 424 through which the system guidewire 418 is deliverable. Inner member 416 terminates at a conical distal tip 420 which facilitates forward translation of the device through tortuous vasculature. Extending from a proximal facing surface of conical tip 420 are extensions members 422, such as pins or hooks, which extend parallel to the longitudinal axis of the system. The distal end 426 of intermediate member 410 may define a receptacle or cup for receiving pins 422 so as to capture the apices 428 of the distal end of the main stent lumen 450 when operatively loaded within thereon (see FIG. 18A). The proximal end 412 of outer sheath 408 provides branched luminal ports 412 to receive side branch guidewires 420 as well as respective deployment members (e.g., strings) 416 for directing and deploying the side branch lumens of a branched stent (not shown). The strings 416 may be controlled and tensioned by mechanism as described above. Here, two ports 412 are provided for a stent having two side branches, however, more or fewer ports may be provided to accommodate stent's having any number of side branches. As with the embodiments described above, internal valve mechanisms may be provided to fluidly seal the luminal ports 412, thereby preventing leakage of blood therefrom.

The proximal portion 404 of delivery and deployment system 400 includes handle 428 portion which may have proximal and distal portions which are axially translatable axially with respect to each other, as described above, to control the amount of extension and foreshortening undergone by the main body of a stent operatively loaded within the delivery system. Handle 428 provides a pair of controls including a knob 430 to which one end of the deployment/attachment member(s) (e.g., strings) for controlling the deployment of the proximal end of a stent device is permanently anchored but which itself is removable from the handle to manually pull the strings there through. A hemostatic valve may be incorporated into the handle for preventing the back flow of fluid, e.g., blood, out of the handle when the knob is removed therefrom. The counter control is provided by dial or drive screw 432, which is used to releasably anchor the free ends of the string or string set to the handle. As described above with respect to the delivery system of FIGS. 2A and 2B, these control members are used in tandem to maintain a constant tension on the attachment strings and keeping the implant restrained at its proximal end within the delivery system while the delivery system is being articulated through the vasculature.

Figure 18A:
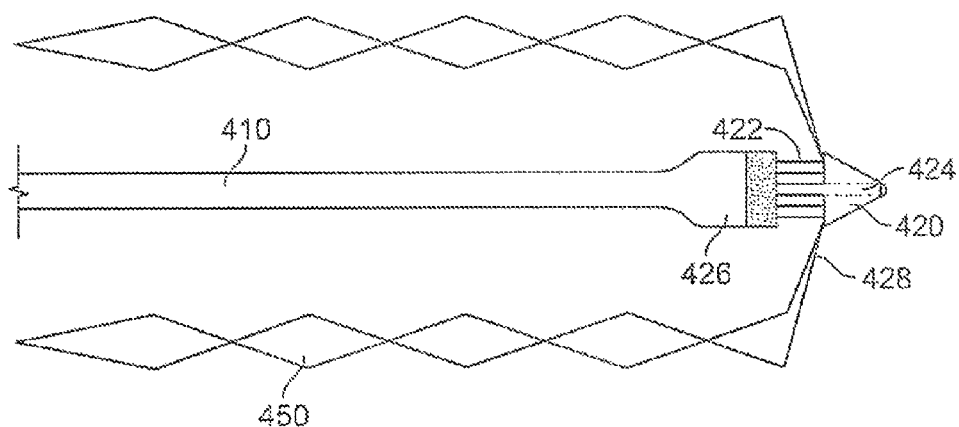
FIGS. 18A and 18B are cross-sectional side views of a deployment/attachment mechanism of the system of FIG. 17 having a stent operably attached and deployed, respectively.
Figure 18B:
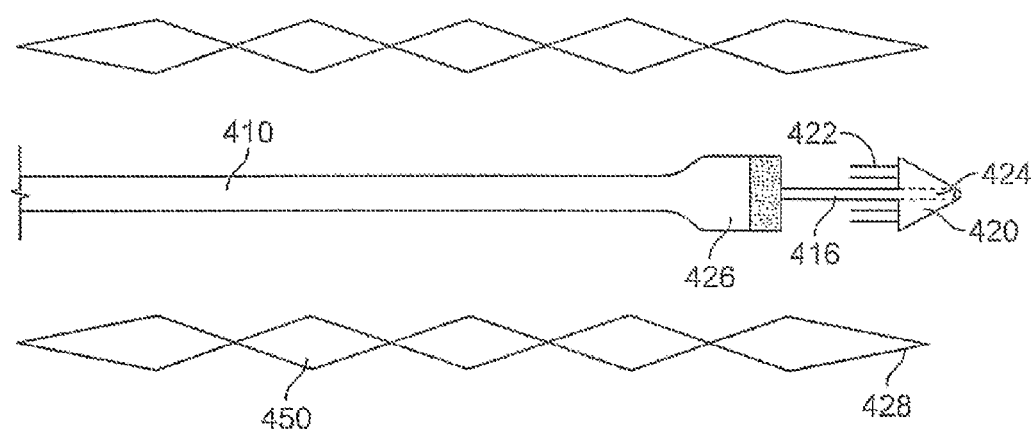

FIGS. 18A and 18B illustrate the retention and deployment, respectively, of a distal end of a main stent lumen 450 from system 400. As mentioned previously, the apices 428 or the like of the stent cells at the distal most end of the stent, when loaded, are synched or held radially inward and are captured by the engagement of pins 422 of inner member 416 and receptacle 426 of intermediate member 410, as illustrated in FIG. 18A. The engagement of the pins within the receptacle may be biased or spring-loaded such that, by operating a release mechanism, such as by the depression of a button 434 on handle 428, inner member 428 is caused to advance or spring forward so as to retract the pins from the receptacle and free the stent apices 428, as illustrated in FIG. 18B. Alternatively, the system may be configured such that intermediate member 410 may be retracted to release the pins from the receptacle.

Any type and combination of deployment/attachment members and mechanisms may be used with the subject stent delivery systems, where each end of the stent lumens is controlled by the same type of mechanism, or one or more ends of the stent lumens may be retained and released by one type of mechanism and one or more of the other stent ends may be retained and released by another type of mechanism.

The catheters and/or guidewires employed with the systems of the present invention may include intravascular ultrasound (IVUS) imaging capabilities where one or more miniaturized transducers are mounted on the tip of a catheter or guidewire to provide electronic signals to an external imaging system. Such a transducer array may rotate to produce an image of the lumen of the artery showing the precise location of the take offs for the connected branch vessels that will receive the connected branch stents or other cavities into which the catheter is inserted, the tissue of the vessel, and/or the tissue surrounding the vessel. In addition to facilitating visualization during stent delivery and deployment, such systems enhance the effectiveness of diagnosis and treatment by providing important diagnostic (i.e., pre-stenting) information, e.g., the location and size of an aneurysm, that is not available from conventional x-ray angiography. Intravascular ultrasound (IVUS) imaging catheters are commonly used as a preliminary step in the procedure of selecting the appropriately sized stent graft before placing a non-branched stent for several reasons which include to ensure that coverage of a side branch vessel is not mistakenly done. Combining the imaging ability into the tip of the stent delivery catheter has the advantages of saving time by avoiding a catheter exchange. A second technique which is commonly done to avoid the exchanging of the stent delivery catheter and the IVUS catheter through the access site is to gain another access point to introduce the separate IVUS catheter. By integrating the IVUS transducers on the tip of the stent delivery catheter, one eliminates the need for a second vascular access wound should the imaging catheter have been delivered through a bilateral groin access location. Also, when placing a stent inside another stent, an IVUS catheter is used to ensure that the second stent will be deployed within the lumen of the first stent in an overlapping fashion to extend the coverage length of the treated region. In those cases, a first stent has been placed and the downstream portion is free floating within a large aneurysm sac and, as such, care must be taken to ensure that the second stent to be placed within the first stent is not outside the lumen of the first stent. To do otherwise, may result in unintentionally occluding the vessel requiring the procedure to be converted to a surgery to remove the misplaced second stent.

Methods of Device Implantation

Figure 8B:
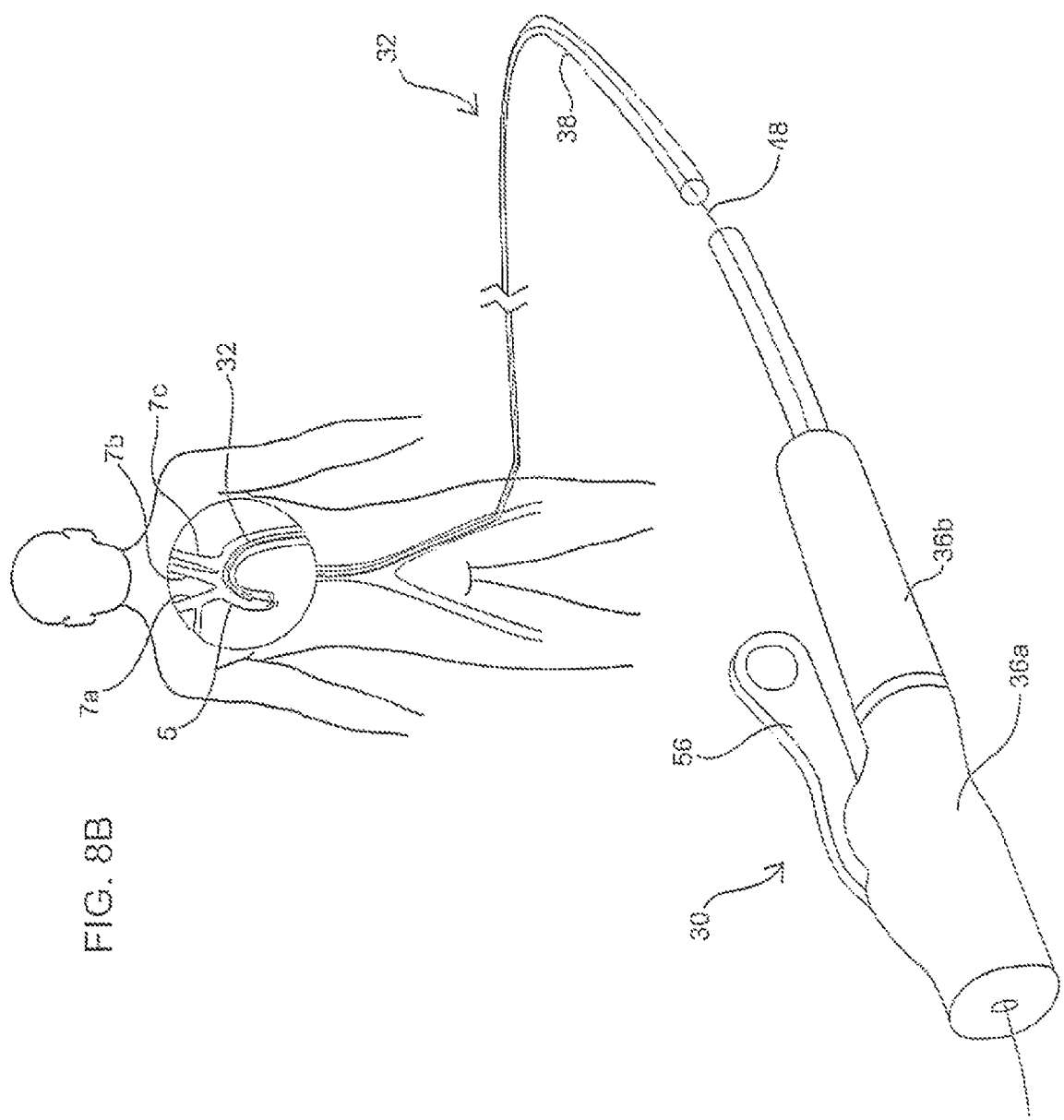
Figure 8C:
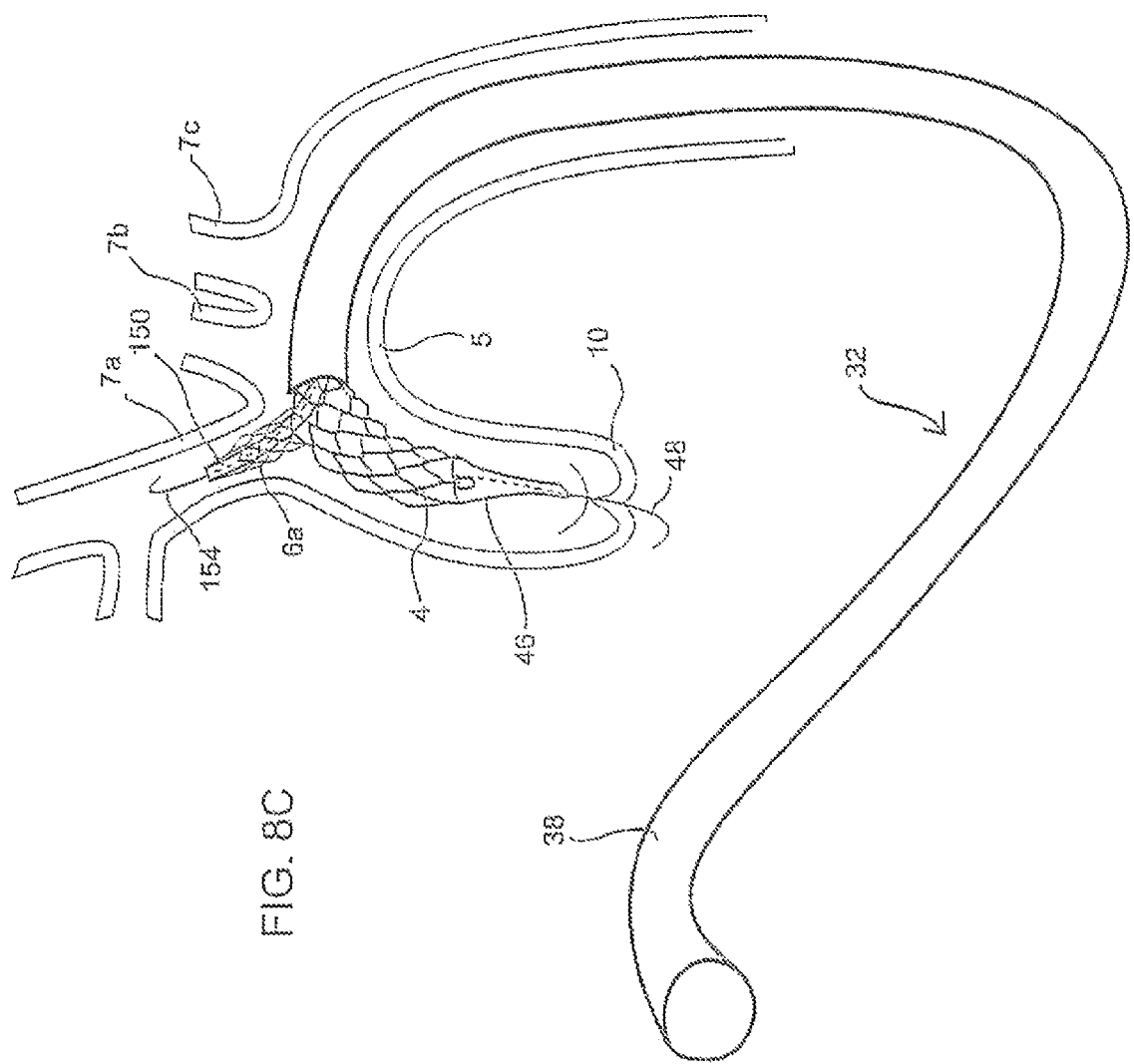
Figure 8D:
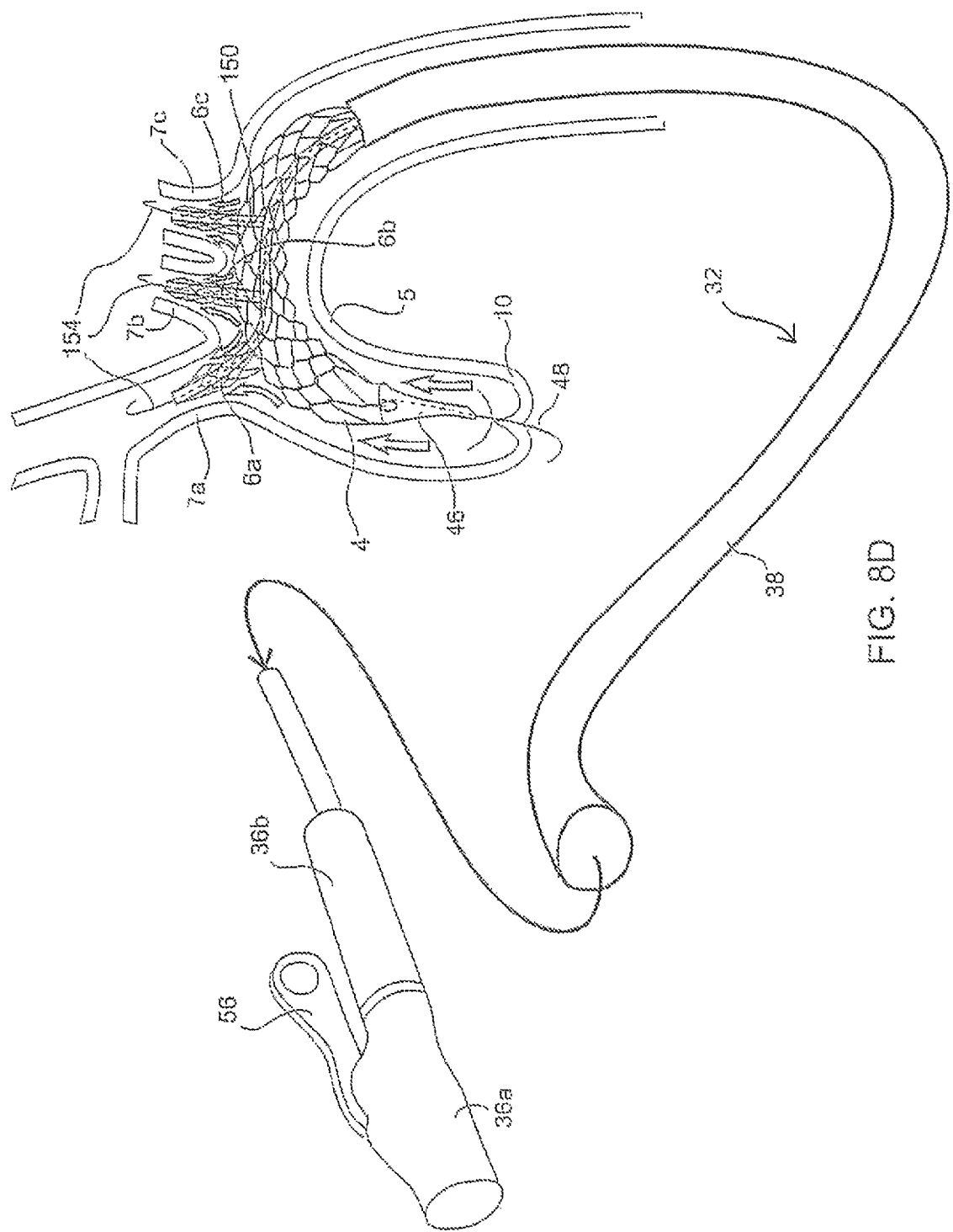
Figure 8E:
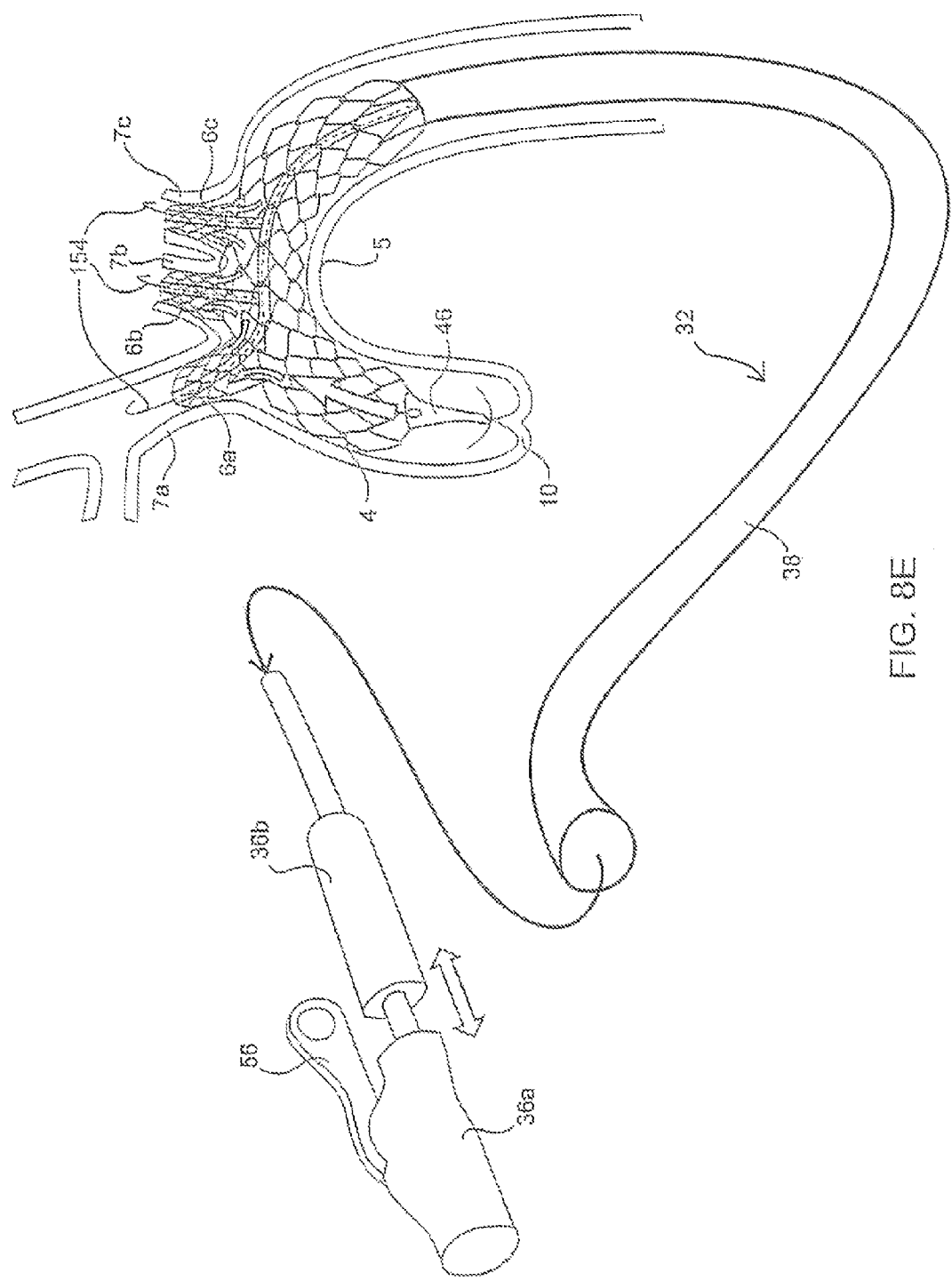
Figure 8F:
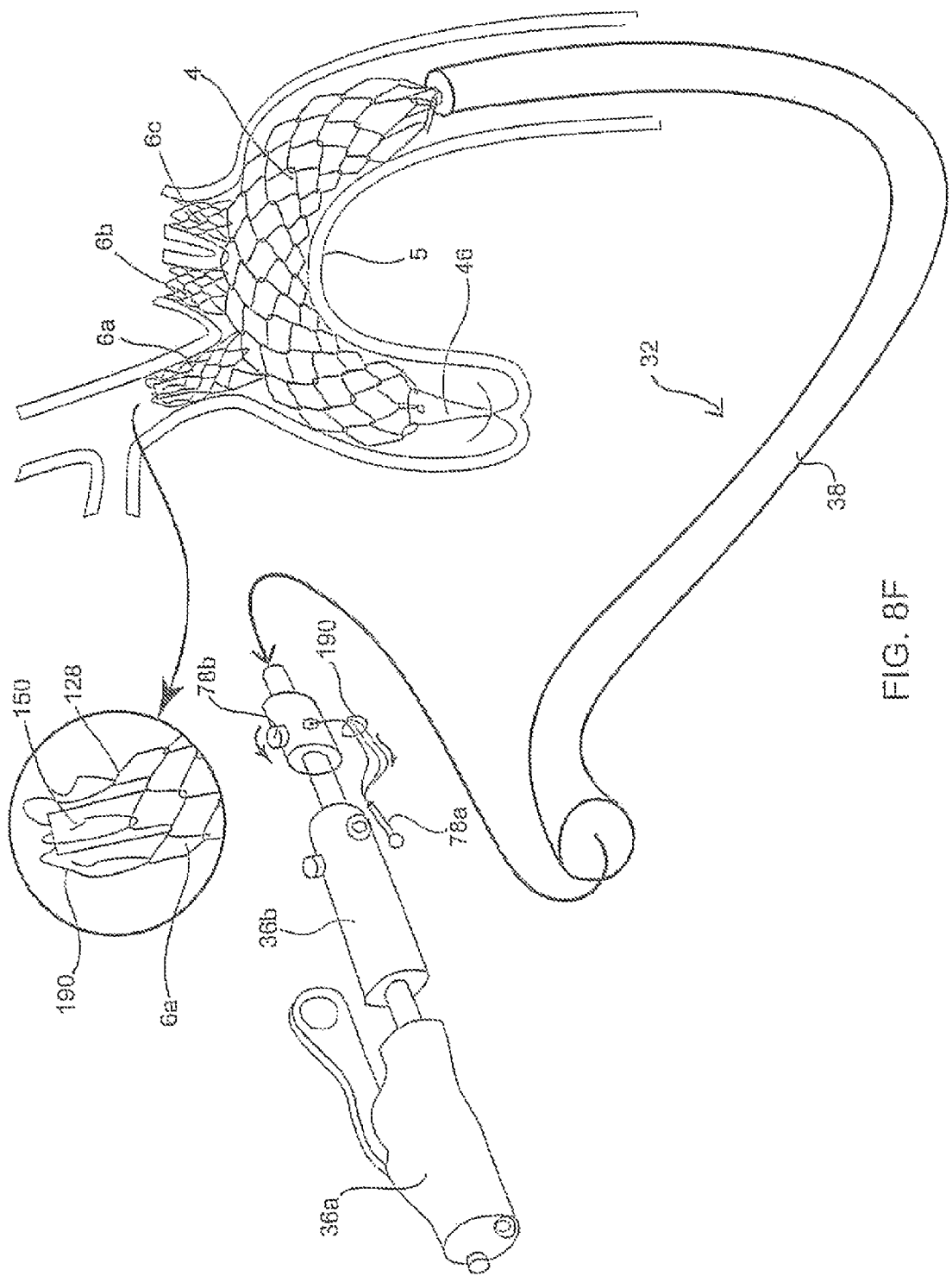
Figure 8G:
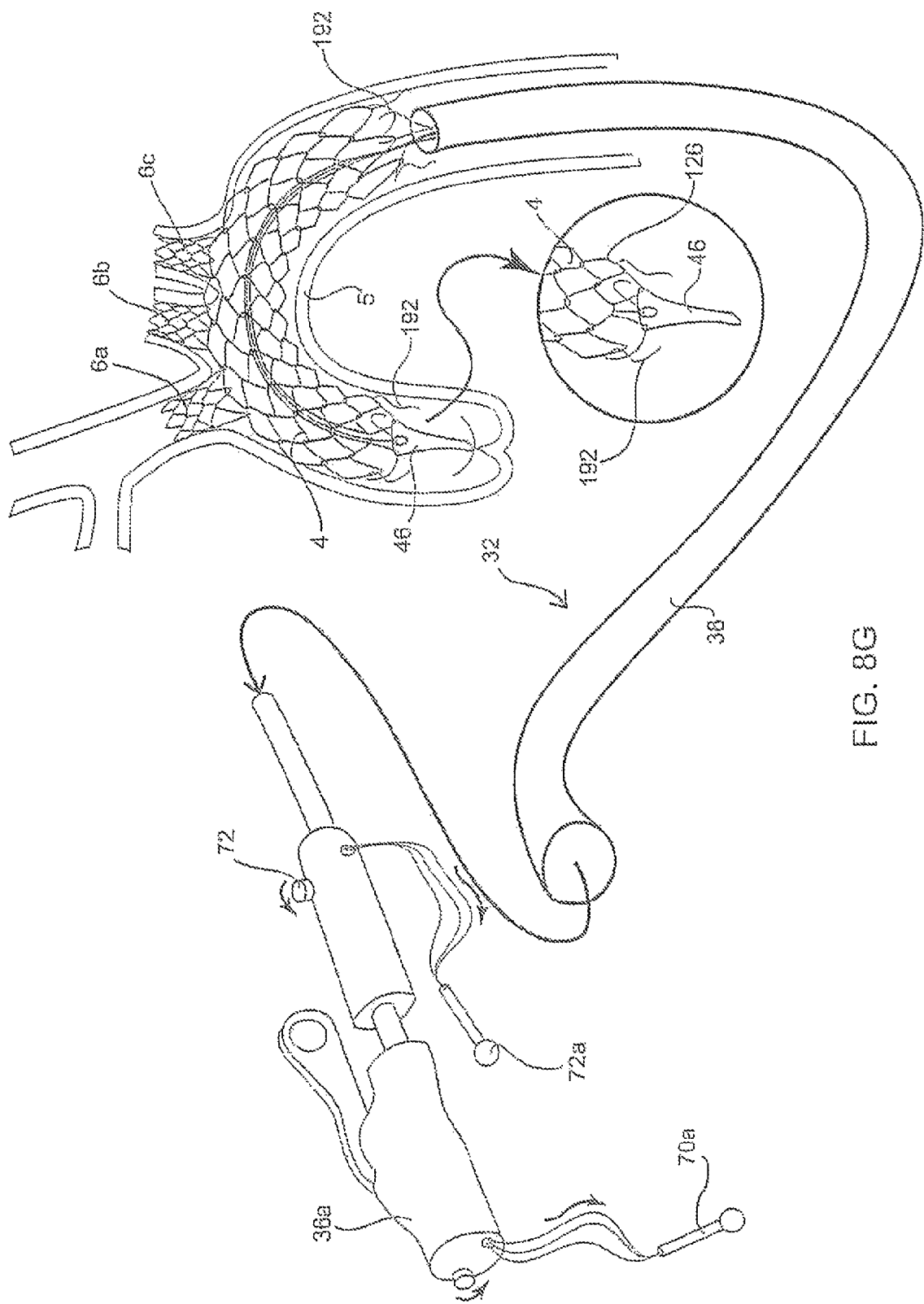
Figure 8H:
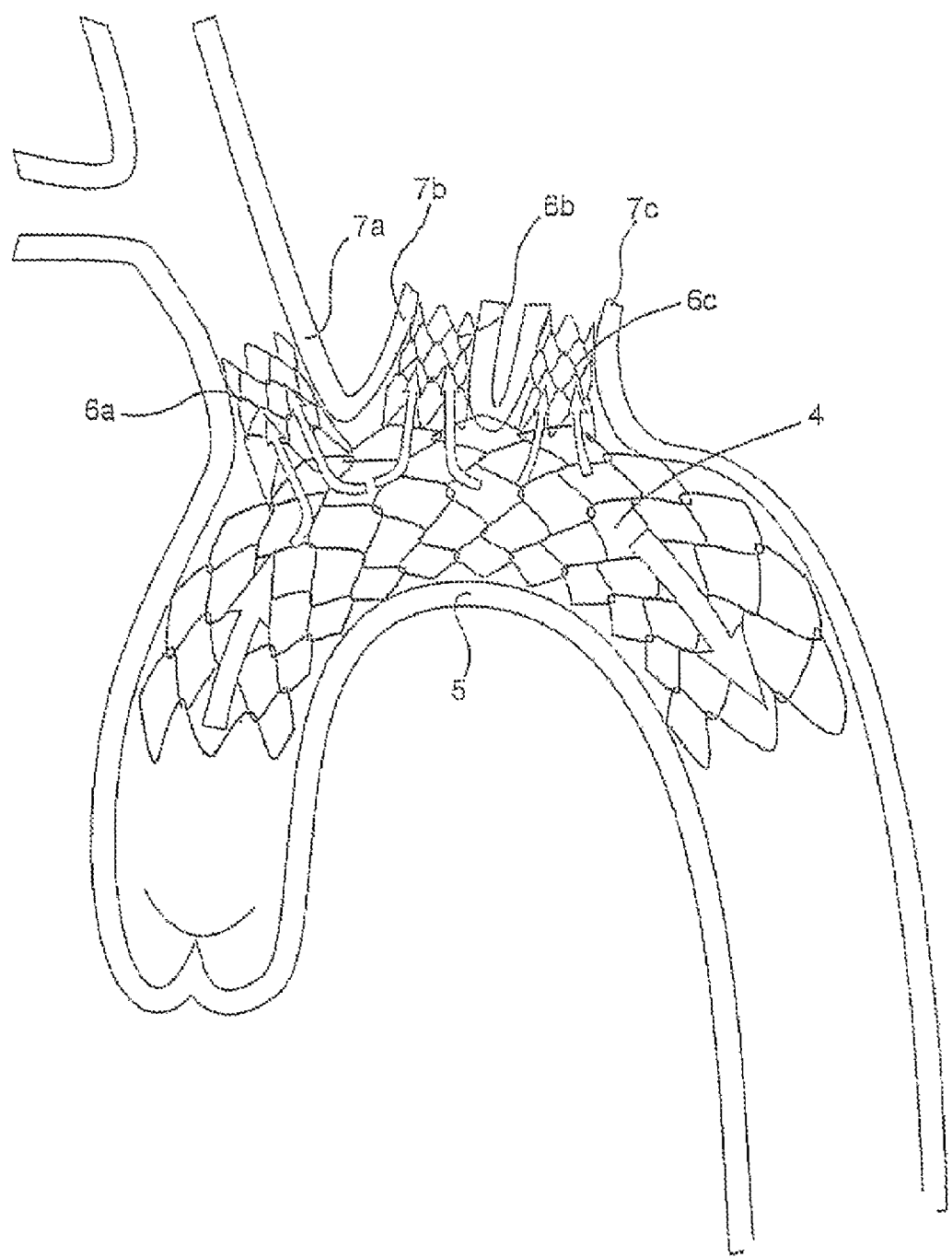

The implantation procedure for the subject devices will now be described with respect to FIGS. 8A-8H and in the context of an aortic arch application in which a stent-graft 2 of the present invention, such as that illustrated in FIG. 1A, having a main body lumen 4 and three side branch lumens 6a, 6b and 6c, is percutaneously implanted within the aortic arch 5, where, upon implantation, main body lumen 4 will reside within the aortic arch 5 and the three side branch lumens 6a, 6b and 6c will reside in the innominate artery 7a, the left common carotid artery 7b and the left subclavian artery 7c, respectively, as illustrated in FIG. 8H.

By means of a Seldinger technique via the left femoral artery 8, or abdominal aortatomy, a main or aortic guide wire 48 is advanced through the vasculature to the aortic arch 5 up to or until distal tip 48a is caused to cross the aortic valve 10, as illustrated in FIG. 8A. Catheter portion 32 of the implantation system 30 of the present invention, provided with stent-graft 2 operatively loaded therein, is then percutaneously introduced into the patient's body over guide wire 48.

It is noted that stent-grafts or stents otherwise covered with a material, e.g., an ECM, may require reconstitution or hydration of the graft or covering prior to commencing the implantation procedure. This may be accomplished by flushing the guide wire lumen of delivery system catheter with saline prior to inserting the catheter into the body. Alternatively this could be done by rinsing in open air prior to sheathing.

While stent graft 2 is in a loaded, undeployed state within catheter portion 32, the delivery system's handle is in the retracted position, i.e., proximal handle portion 34a and distal handle portion 34b are engaged with each other. With the handle in the retracted position (shown in FIGS. 8B and 8D), inner member 42 is held in a distally advanced position and intermediate member 40 is held in a proximally retracted position. This relative axial relationship between the intermediate and inner members, maintains stent graft 2, or at least its main lumen 4, in a stretched or tensioned condition. This is so as the distal crowns of main lumen 4 are attached to the distal end of inner member 42, which in turn is fixed to proximal handle portion 34a, and the proximal crowns of main lumen 4 are attached to the distal end of intermediate member 40, which in turn is fixed to the distal handle portion 36b.

Catheter portion 32 is then steered as necessary by means of manipulating lever 56, thereby deflecting the distal tip of catheter 32, as described above with respect to FIG. 4, and advanced into the descending aorta and then into aortic arch 5. It is important that catheter portion be properly rotationally positioned so that side branch lumens 6a, 6b and 6c of stent graft 2 are substantially aligned with arteries 7a, 7b and 7c, respectively, into which they are to be delivered. To this end catheter 32 is torquable and fluoroscopic guidance may be employed to further facilitate delivery of catheter portion 32. In particular, fluoroscopic markers (not shown) on the crowns of the stent graft lumens may be tracked and accurately positioned for optimal placement within the respective arteries. The stent itself may be radiopaque. The tip of the catheter will be radiopaque as well. A steerable guidewire may be used to direct the main catheter 32 and the side branch catheters as the stretched main stent body and side branch stent bodies are steered by deflectable tipped guidewires placed into the target implant site.

Throughout the delivery and deployment procedure, the various lumens of catheter portion 32 may be continuously flushed with a fluid, e.g., saline or contrast agent, in a retrograde direction (relative to the blood flow) at a pressure that is greater than or substantially equal to the pressure of the arterial blood. This prevents possible leakage of blood from the system as well as prevents any interference with the functioning of the delivery process, particularly keeping the stent strings lumens free and clear of blood, thereby eliminating clotting within the lumens. Additionally, because each lumenal end of the stent graft (i.e., the proximal and distal ends of main lumen 4 as well as the distal ends of the side branch lumens) is individually controlled (however, some or all may be collectively controlled) by the delivery and deployment system 30 of the present invention, the interconnected cells of the stent may be selectively elongated in an axially direction, permitting the continual flow of blood around the device during deployment within the anatomy. This axial elongation feature also permits the implantation of larger diameter side branch stents within a vessel having a smaller diameter.

Once the distal end of catheter portion 32 is operatively positioned within the aortic arch 5, outer sheath 38 is retracted by manually pulling on fitting 50 (see FIG. 3A) to expose the proximal end of nose cone 46 of inner member 42 and to partially deploy the distal portion of the main or aortic lumen 4 of stent graft 2 within the ascending aorta, as shown in FIG. 8C. With partial deployment of stent graft 2, i.e., main aortic lumen 4 is maintained in a stretched or tensioned state, arterial blood flow exiting from aortic valve 10 flows through and around main lumen 4. It is important to note that with main lumen 4 in this partially deployed state, stent graft 2 can be easily repositioned within the vasculature as it is not yet engaged with the vessel walls and, thus, is not subject to the frictional resistance that contact with the walls would cause, not to mention the avoidance of the resulting endothelial damage and/or plaque embolization which is likely to occur.

While the various side branch lumens 6a, 6b and 6c of stent graft 4 may be deployed serially (one at a time) in any order or parallely (simultaneously) together, it may be easiest to deploy the side branch stent lumens one at a time in order from the most distally positioned stent lumen (6a) to the most proximally positioned stent lumen (6a). This deployment order eliminates unnecessary or repetitious translation of outer sheath 38 over the stent graft, i.e., only gradual, unidirectional (proximal) translation is necessary. This is advantageous in that abrasions to the graft material are minimized, which is particularly important when coated with a material, e.g., extra cellular matrix, or a drug. This deployment order further reduces the necessary deployment steps and, thus, the total time necessary for the implantation procedure.

To deploy a side branch stent lumen, such as stent lumen 6a, a side branch guide wire 154 is inserted into (or may be preloaded within) side branch port 110 of the respective control hub in its full distally advanced position and into a lumen 152 of side branch catheter 150 positioned within lumen 148 of intermediate member 40 (see FIG. 6A). At the same time, outer sheath 38 is incrementally and gradually retracted proximally to allow the distal end of guide wire 154 to be translated through side branch catheter 150, out its distal end and into innominate artery 7a, as shown in FIG. 8C. The respective control hub 74 is then distally translated along intermediate member 40 and may be fully engaged with the associated catheter hub 84, thereby exerting maximum tension being applied to the side branch stent cells by the attached attachment strings and partially deploying side branch stent 6a as shown in 8D. Note that the main body stent cells are being held stretched distal to proximal through the relative positions of the inner member and intermediate member as controlled by the handle in the close configuration while the side branch stent is likewise maintained in a stretched position by the distally advanced side branch catheter. This procedure is repeated as necessary for the remaining number of side branch stents, in this case, side branch stents 6b and 6c which are delivered into the left common carotid artery 7b and the left subclavian artery 7c, respectively, as illustrated in FIG. 8D. Note that at this partially deployed state the blood flow is around the device as well as through the implant depending on how tight and over what extension length the attachment strings are pulled to the inner member exit ports 184. It may be desirable to have just flow around the device and not through the lumen of the device and that can be accomplished by cinching down on the attachment strings on the distal end of main lumen to allow the most minimal length of attachment thereby bringing the main lumen of stentgraft to be held closed against distal tip 46 or inner member 42. It is important to note that the distance between the distal main stent end and its connection to the inner member is controllable by the length of distal attachment strings which are controlled by the string clamp 70b by adjusting and selecting the location of where the clamp locks onto the distal attachment strings. This adjustment can be made in situ while the stent is being delivered. Likewise the distance between the proximal main stent end and its connection to the intermediate member is controllable by the length of proximal attachment strings which are controlled by the string clamp 72b by adjusting and selecting the location of where the clamp locks onto the proximal attachment strings. This adjustment can be made in situ while the stent is being delivered.

After placement within the branch arteries of all of the side branch stents in their partially deployed states, the stent graft is ready for full deployment. This is accomplished by moving the system handle to the extended position, i.e., proximal handle portion 34a and distal handle portion 34b are axially separated from each other, as illustrated in FIG. 8E. This action causes inner member 42 to translate proximally relative to the fixed intermediate member 40 and in turn relaxes the tension applied to the cells of main lumen 4, thereby bringing the lumen ends closer together. As such, the stent foreshortens and there is a corresponding increase in the-diameter of main lumen 4, thereby securing main lumen 4 against the walls of the aorta.

The side branch catheters are likewise translated proximally by moving the respective control hub 74, 76, 78 a distance further from its corresponding catheter hub 84, 86, 88 thereby relaxing the tension applied to the cells of the side branch stent. As such there is a corresponding increase in the diameter of side branch lumens 6a, 6b, 6c as the lumenal ends foreshorten. It is important to note that the distance between the stent ends and the catheter end is controllable by adjusting the length of the strings traversing between the fixed-end knob 70a, 72a, 74a, 76a, 78a and the releasable end clamp 70b, 72b, 74b, 76b, 78b.

Once the stent cells have been released of their tension by the translation of the catheter handle and side branch catheters, and as the stent opens to a diameter which is expanded against the surrounding artery wall, the entire blood flow enters through the distal end of the device and exits all of its other lumens. Preferably, blood flow is sealed from around the outside of the stentgraft once the stent has been fully deployed.

While the stent itself may be fully deployed as shown in FIG. 8E, it is still attached by attachment string sets to each of the distal ends of inner member 42, intermediate member 40 and each side branch catheter 150a, 150b, 150c. The lumenal ends of the stent graft can now be detached from their respective catheters. The stent graft's lumenal ends may be released serially (one at a time) in any order or parallely (simultaneously) together. As shown in FIG. 8F, the lumenal ends of the side branch lumens 6b and 6c have been released, with the respective attachment strings 190, side branch catheters 150a, 150b, 150c and side branch guide wires 154 having been retracted. For each side branch lumenal end, such as illustrated for side branch lumen 6a, catheter detachment is accomplished by actuating the designated control clamp 74b, 76b and 78b on its respective catheter hub 74, 76, 78 to release the free ends of strings 190 from the screw clamp of catheter hub and, at the same time, by removing control knob 74a, 76a, 78a from the handle and pulling strings 190 to the extent that the free ends unloop or detach from the respective stent's crowns 128 of FIG. 8F. The strings 190 need only be pulled until their free ends release the crowns but may be withdrawn within the distal end of catheter portion 32.

As illustrated in FIG. 8G, a similar procedure is performed with respect to deployment of the distal and proximal ends of main lumen 4, where either end may be deployed first or both ends may be deployed simultaneously The designated control clamp 70b, 72b is actuated to release the free ends of strings 192 and, at the same time, control knobs 70a, 72a is removed from the handle thereby pulling strings 192 to the extent that the free ends unloop or detach from the respective stent's crowns 126. Strings 192 need only be pulled until their free ends release the crowns but may be withdrawn within the distal end of catheter portion 32. The entirety of catheter portion 32 may then be removed from the vasculature with stent graft 2 in a fully deployed state within the aortic arch 5, as shown in FIG. 8H.

Figure 11:
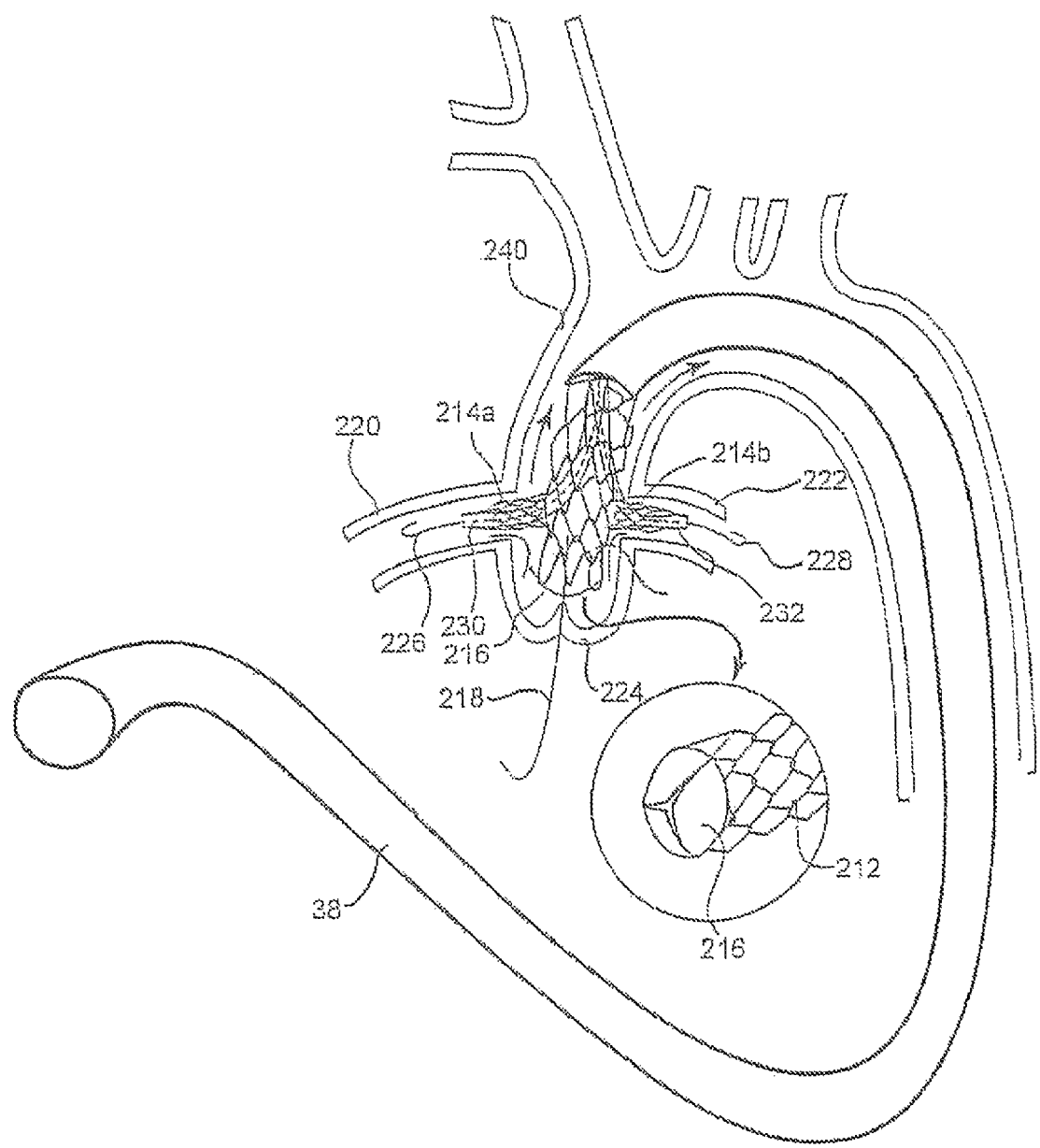
FIG. 11 illustrates the partial deployment of the implant of FIG. 1E within the aortic root.

Referring now to FIG. 11, the partial deployment step of the above described procedure is illustrated with respect to the delivery and deployment of the implant 210 of FIG. 1E. Specifically, catheter portion 38 of the delivery system is positioned within the aorta with the distal portion of main stent lumen 122 partially deployed within the aortic root and ascending aorta 240, and side branch lumens 214a and 214b partially deployed within the right and left coronary ostia 220 and 222, respectively. A main guidewire 218 extends from catheter 38 and crosses the former location of the natural aortic valve 224, while side branch guidewires 226 and 228 extend within the coronary ostia 220, 222 from side branch catheters 230 and 232, respectively. Upon release of the attachment strings for the main lumen of the implant, prosthetic aortic valve 216 will reside within the natural annulus 224. The side branch lumens 214a, 214b may be deployed simultaneously with each other and with main lumen 212, or serially in any order.

In any surgical or endovascular procedure, such as the one just described, the fewer incisions made within the patient, the better. Of course, this often requires highly specialized instrumentation and tools used by a highly skilled surgeon or physician. In consideration of this, the above-described single-incision device implantation procedure may be modified to include the creation and use of one or more secondary incisions to facilitate the initial delivery of the catheter portion 38 of the delivery system 32 at the implantation site and to further ensure proper orientation of the stent graft upon its deployment at the site.

The two-incision (or multiple-incision) procedure of the present invention involves a primary incision, e.g., a cutdown in the femoral artery as described above, through which the above-described delivery and deployment system is introduced into a first vessel within the body, e.g., into the aortic arch, and a second incision (or more) at a location(s) that provides access to at least one vessel which intersects the first vessel, e.g., one of the side branches of the aortic arch. This procedure is now described with reference to FIGS. 12A-12F and in the context of implanting the stent graft 2 of the present invention in the aortic arch by use of a primary incision made in the left femoral artery 8 to access the aortic arch 5 and a single secondary incision made in the brachialcephalic or radial artery 15 to access one or more arteries of the aortic tree.

First and second access incisions are made—in the left femoral artery 8 and the left brachycephalic artery 15, respectively. By means of a Seldinger technique, a secondary or "tether" guide wire 300 is advanced through the left brachycephalic artery 15 into the innominate artery 7. Guide wire 300 is then further advanced into the aortic arch 5, the descending aorta 11, the abdominal aorta 13 and the left femoral artery 8 where it exits the body through the femoral incision, as illustrated in FIG. 12A. A secondary or "tether" catheter 302 is then tracked over the femoral end 300a of guide wire 300 and along the length of the guide wire until catheter 302 is advanced out of the brachial incision, as illustrated in FIG. 12B. Any suitable off-the-shelf system for cardiovascular applications may be employed for use as the secondary or tether guide wire and catheter. A dual lumen rapid-exchange (RX) catheter, such as the one illustrated, having a second lumen positioned at the proximal end of catheter 302. An advantage of an RX catheter is that it only requires the string(s) (or a guidewire) to be pushed a relatively short distance (requiring little "pushability") before it exits the lumen rather than a greater distance in which the string would be difficult to push due to its limp nature. Alternatively, the very end of catheter 302 may be provided with a thru-hole or a cross-hole in the catheter wall, as illustrated in FIG. 12C'.

The above described implantation system 30 is then provided with stent-graft 2 operatively loaded therein. For this procedure, as illustrated in FIG. 12C, side branch attachment strings 190, or at least one string thereof, for deploying the most distally located side branch stent lumen 6a (i.e., the one intended for implantation into the innominate artery 7a) and attached thereto (to one or more stent crowns) are extended from side branch catheter 150a of primary or stent delivery system catheter 38 and then threaded through a side branch tether tubing 35. The strings are then knotted 37a to prevent proximal withdrawal back into catheter 150a and tubing 35. The remaining distal length of strings 190 are then threaded through the exchange lumen 304 of tether catheter 302. The ends of the strings are then knotted a second time 37b to prevent proximal withdrawal of the strings from exchange lumen 304. With the secondary catheter embodiment of FIG. 12C, the strings are threaded into the main lumen 302 and out the side hole 305. The distal string ends are then knotted 37b.

Figure 12D:
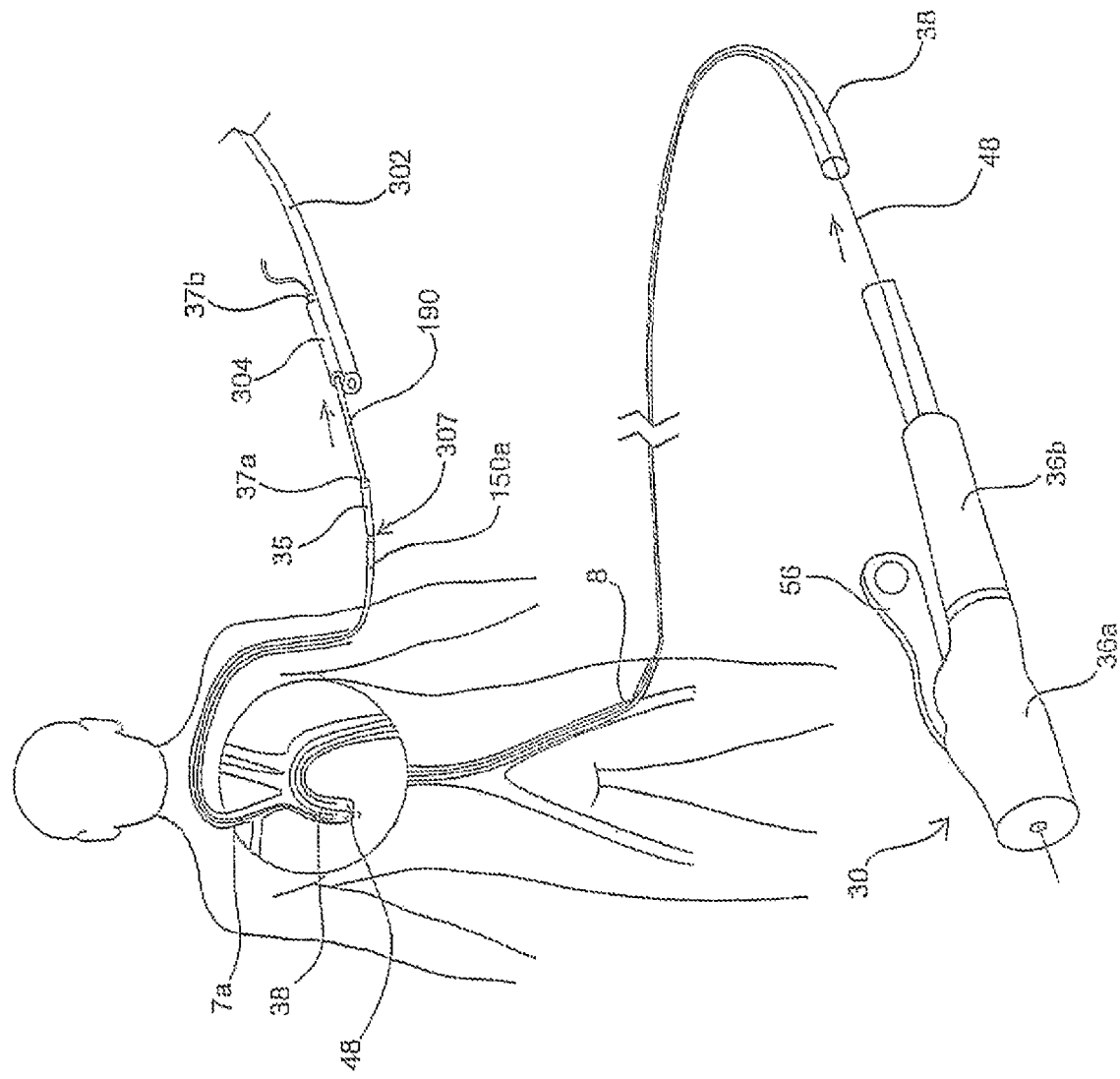

Secondary catheter 302, with side branch catheter 150a in tow as well as the entirety of stent catheter 38 including primary or main guide wire 48, is then advanced back through the femoral incision over secondary guide wire 300 until catheter 302 is fully withdrawn from the brachial incision, as illustrated in FIG. 12D, and until the distal end of side branch catheter 150a is also extended from the brachial incision. Tether guide wire 300 can now be removed from the body. At this point, strings 190 are cut at a location 307 between the distal end of side branch catheter 150a and the opposing end of secondary catheter 302 to release the tether catheter 302 from the stent deployment system.

Figure 12E:
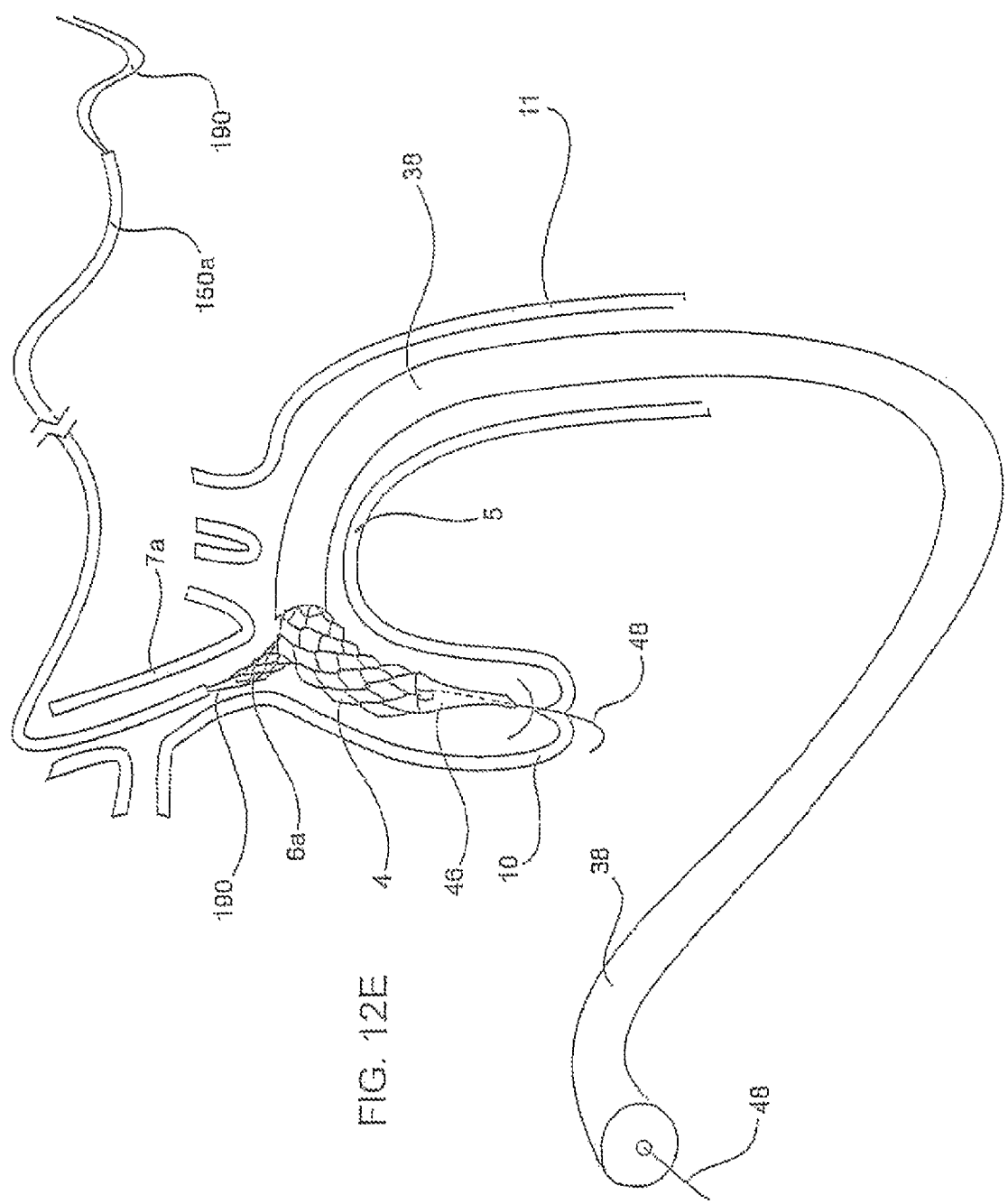

By the tension applied to strings 190 and the translation thereof, side branch 6a of stent graft 4 has been drawn into the innominate artery 7a, as illustrated in FIG. 12E, in a partially deployed state (i.e., exposed but stretched). Concurrently, stent guide wire 48 is advanced over the aortic arch 5 and across the aortic valve 10, thereby advancing nose cone 46 and thus the distal end of the partially deployed (i.e., exposed but stretched or tensioned) main stent lumen 4 into the ascending aorta. Meanwhile, stent catheter 38 has been tracked over stent guide wire 48 into the aortic arch 5. Continued forward advancement of stent catheter 38 is blocked by the partially deployed side branch lumen 6a. As discussed above, with main lumen 4 maintained in a stretched or tensioned state (as well as side branch lumen 6a), various advantages are provided: arterial blood flow exiting from aortic valve 10 is allowed to flow to the brain and body; repositioning of the stent graft 2 is possible, and the likelihood of endothelial damage and/or plaque embolization from the aortic wall is greatly minimized.

For stents and stent grafts having two or more side branch lumens 6a, 6b, 6c, as in FIG. 12F, the procedure described above and illustrated in FIGS. 12A-12E with respect to the implantation of a stent having a single side branch lumen is simultaneously performed, with separate designated tether guide wires and catheters 150a, 150b, 150c. As illustrated in FIG. 12F, with at least the distal end of the main stent lumen 4 accurately positioned and partially deployed within the ascending aorta, the respective side branch lumens 6a, 6b, 6c are deployed within the innominate artery 7a, left common carotid artery 7b and the left subclavian artery 7c, respectively. Alternatively, one or more of the side branch lumens may be partially deployed as described with respect to FIGS. 12A-12F, and the remaining side branch lumens, if any, may be deployed in the manner described above with respect to FIGS. 8C and 8D. Finally, with all side branch lumens 6a, 6b, 6c partially deployed within their respective arteries, the procedural steps described with respect to FIGS. 8E-8H may be performed to fully deploy the all lumens of the stent graft and remove the delivery system from the body.

While the implants of the present invention have been described as being deployable by stent restraining members or mechanisms, it is understood that the subject implants may be configured such that they and/or their lumenal ends are configured for deployment by an expandable member or members. For example, each of the ends of the implant (i.e., of the main lumen and of the side branch lumen(s)), in a loaded, undeployed state, may be coupled to one or more of the nested catheters by placement about an expandable balloon affixed to the catheter(s). The balloons, in either a partially or fully expanded state, provide a sufficiently snug fit with the implant ends such that the lumens of the implant may be selectively stretched or tensioned along their lengths when manipulating the catheter components.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

It must be noted that as used herein and in the appended claims, the singular forms "a", "an", and "the" include plural referents unless the context clearly dictates otherwise. Thus, for example, reference to "a string" may include a plurality of such strings and reference to "the tubular member" includes reference to one or more tubular members and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

That which is claimed is:

1. A method of implanting a device at a target site within an aortic arch adjacent at least one side branch vessel in fluid communication with the aortic arch, the device comprising a main lumen and at least one branched lumen extending laterally therefrom, the method comprising:
   providing a catheter system within which the device has been operatively loaded wherein each of a proximal end and distal end of the main lumen and the free end of the at least one branched lumen is releasably attached to the catheter system;
   creating an incision within the vasculature;
   advancing the catheter system through the vasculature from the incision to a target site within the aortic arch;
   advancing the distal end of the main lumen from a distal end of the catheter system wherein the distal end of the main lumen remains releasably attached to the system within the aortic arch;
   advancing the free end of the at least one branched lumen from a distal end of the catheter system into the side branch vessel while the main lumen remains within the aortic arch and wherein the free end remains releasably attached to the catheter system wherein tension applied to the distal end of at least one side branch luminal end elongates the at least one side branch lumen during advancement into the side branch vessel and where controlling the tension allows expanding and maintaining the side branch lumen in a partially deployed state prior to releasing from the catheter system into a fully deployed state;
   detaching at least one of the advanced luminal ends from the system to implant the device.

2. The method of claim 1 wherein the advanced luminal ends are retractable to within the system prior to detachment from the system.

3. The method of claim 1 wherein at least one luminal end of the device is releasably attached to the catheter system by a spring-loaded mechanism.

4. The method of claim 3 wherein the spring-loaded mechanism comprises a plurality of extensions and a receptacle for engaging the extensions, wherein the plurality of extensions are biased to be unengaged with the receptacle.

5. The method of claim 4, wherein the luminal ends comprise apices and the system is configured to releasably capture the apices between the extensions and the receptacle.

6. The method of claim 1, wherein at least one luminal end of the device is releasably attached to the catheter system by at least one string.

7. The method of claim 1, where the side branch vessel is selected from the group consisting of an innominate artery, a common carotid artery, and a subclavian artery.

8. A method of implanting a device at a target site within the body having a main vessel and at least one laterally extending side branch vessel in fluid communication with the main vessel, where the device includes a main lumen and at least one side-branch lumen extending therefrom, the method comprising:
  providing a catheter system within which the device is operatively loaded wherein each of a proximal end and distal end of the main lumen and the free end of the at least one branched lumen is releasably attached to the catheter system;
  creating an incision within the vasculature;
  advancing the catheter system through the vasculature from the incision to a target site within the main vessel;
  advancing the distal end of the main lumen from a distal end of the catheter system wherein the distal end of the main lumen remains releasably attached to the system within the main vessel;
  advancing the free end of the at least one branched lumen from a distal end of the catheter system from the main vessel and adjacent to the main lumen laterally into the side branch vessel while the main lumen remains within the main vessel and wherein the free end remains releasably attached to the system, wherein tension applied to the distal end of at least one side branch luminal end elongates the at least one side branch lumen during advancement into the side branch vessel and where controlling the tension allows expanding and maintaining the side branch lumen in a partially deployed state prior to releasing from the catheter system into a fully deployed state; and
  detaching at least one of the advanced lumenal ends from the system to implant the device.

9. The method of claim 8, wherein the advanced luminal ends are retractable to within the system prior to detachment from the system.

10. The method of claim 8, wherein at least one luminal end of the device is releasably attached to the catheter system by a spring-loaded mechanism.

11. The method of claim 10, wherein the spring-loaded mechanism comprises a plurality of extensions and a receptacle for engaging the extensions, wherein the plurality of extensions are biased to be unengaged with the receptacle.

12. The method of claim 10, wherein the luminal ends comprise apices and the system is configured to releasably capture the apices between the extensions and the receptacle.

13. The method of claim 8, wherein at least one luminal end of the device is releasably attached to the catheter system by at least one string.

14. The method of claim 8, where the main vessel comprises an aortic arch and where the at least one side branch vessels comprise a vessel selected from the group consisting of an innominate artery, a common carotid artery, and a subclavian artery.

15. The method of claim 8, where the main vessel comprises an infrarenal aorta and where the at least one side branch vessels comprise a renal artery.

16. The method of claim 8, where detaching at least one of the advanced lumen ends comprises first expanding the main lumen in the main vessel while the at least one side-branch lumen remains in a stretched state.

17. The method of claim 8, where advancing the free end of the at least one branched lumen comprises first positioning the main lumen of the device in the main vessel while in a stretched condition and subsequently positioning at least one side-branch lumen extending from the main lumen of the device in the at least one side branch vessel while in a stretched or tensioned state.

18. The method of claim 8, wherein the device comprises a wire stent structure where the side branch lumen is adjustable relative to the main lumen until the device expands against the main branch vessel and side vessel.

19. The method of claim 8, wherein the device comprises a wire stent structure where an angular orientation of the side branch lumen is adjustable on the device until the device expands against the main branch vessel and side vessel.

20. The method of claim 8, further comprising maintaining continuous blood flow around the implantable device during placement.

21. The method of claim 8, further comprising repositioning the device before fully detaching at least one of the advanced lumenal ends from the system to implant the device.

22. A method of implanting a device at a target site within the body having a main vessel and at least one laterally extending side branch vessel in fluid communication with the main vessel, where the device includes a main lumen and at least one side-branch lumen laterally extending therefrom, the method comprising:
  providing a catheter system within which the device is operatively loaded wherein each of a proximal end and distal end of the main lumen and the free end of the at least one side-branch lumen is releasably attached to the catheter system;
  creating an incision within the vasculature;
  advancing the catheter system through the vasculature from the incision to a target site within the main vessel;
  advancing the distal end of the main lumen from a distal end of the catheter system wherein the distal end of the main lumen remains releasably attached to the system within the main vessel;
  deflecting the free end of the at least one side-branch lumen from a distal end of the catheter system from the main vessel and adjacent to the main lumen into the side branch vessel while the main lumen remains within the main vessel where the ability of the device to adjust location and position of the main and side branch lumens allows the side branch lumen to accommodate the laterally extending side branch vessel and wherein the free end remains releasably attached to the system;
  controlling tension applied to the distal end of at least one side branch luminal end to elongate the at least one side branch lumen during insertion into the side branch vessel and where controlling the tension allows expanding and maintaining the side branch lumen in a partially deployed state prior to releasing from the catheter system into a fully deployed state; and
  detaching at least one of the advanced lumenal ends from the system to implant the device.

23. The method of claim 22, wherein the advanced luminal ends are retractable to within the system prior to detachment from the system.

24. The method of claim 22, wherein at least one luminal end of the device is releasably attached to the catheter system by a spring-loaded mechanism.

25. The method of claim 24, wherein the spring-loaded mechanism comprises a plurality of extensions and a receptacle for engaging the extensions, wherein the plurality of extensions are biased to be unengaged with the receptacle.

26. The method of claim 24, wherein the luminal ends comprise apices and the system is configured to releasably capture the apices between the extensions and the receptacle.

27. The method of claim 22, wherein at least one luminal end of the device is releasably attached to the catheter system by at least one string.

28. The method of claim 22, where the main vessel comprises an aortic arch and where the at least one side branch vessels comprise a vessel selected from the group consisting of an innominate artery, a common carotid artery, and a subclavian artery.

29. The method of claim 22, where the main vessel comprises an infrarenal aorta and where the at least one side branch vessels comprise a renal artery.

30. The method of claim 22, where detaching at least one of the advanced lumen ends comprises first expanding the main lumen in the main vessel while the at least one side-branch lumen remains in a stretched state.

31. The method of claim 22, where advancing the free end of the at least one branched lumen comprises first positioning the main lumen of the device in the main vessel while in a stretched condition and subsequently positioning at least one side-branch lumen extending from the main lumen of the device in the at least one side branch vessel while in a stretched or tensioned state.

32. The method of claim 22, further comprising maintaining continuous blood flow around the implantable device during placement.

33. The method of claim 22, further comprising repositioning the device before fully detaching at least one of the advanced lumenal ends from the system to implant the device.

* * * * *